US012122830B1

(12) United States Patent
Lee et al.

(10) Patent No.: US 12,122,830 B1
(45) **Date of Patent: *Oct. 22, 2024**

(54) ANTI-ROR1 ANTIBODY AND USE THEREOF

(71) Applicant: ABL Bio Inc., Seongnam-si (KR)

(72) Inventors: Yangsoon Lee, Seongnam-si (KR); Juhee Kim, Seongnam-si (KR); Kyungjin Park, Seongnam-si (KR); Donghoon Yeom, Seongnam-si (KR); Kyeongsu Park, Seongnam-si (KR); Hyejin Chung, Seongnam-si (KR); Yeunju Kim, Seongnam-si (KR); Eunyoung Park, Seongnam-si (KR); Ui-Jung Jung, Seongnam-si (KR); Eunsil Sung, Seongnam-si (KR); Jinhyung Ahn, Seongnam-si (KR); Byungje Sung, Seongnam-si (KR); Daehae Song, Seongnam-si (KR); Youngdon Pak, Seongnam-si (KR)

(73) Assignee: ABL BIO INC., Seongnam-si (KR)

( * ) Notice: Subject to any disclaimer, the term of this patent is extended or adjusted under 35 U.S.C. 154(b) by 719 days.

This patent is subject to a terminal disclaimer.

(21) Appl. No.: 17/057,646

(22) PCT Filed: May 23, 2019

(86) PCT No.: PCT/KR2019/006213
§ 371 (c)(1),
(2) Date: Nov. 21, 2020

(87) PCT Pub. No.: WO2019/225992
PCT Pub. Date: Nov. 28, 2019

(30) Foreign Application Priority Data

May 23, 2018 (KR) ........................ 10-2018-0058336
May 23, 2018 (WO) ................ PCT/KR2018/005854

(51) Int. Cl.

| | |
|---|---|
| ***C07K 16/28*** | (2006.01) |
| ***A61K 39/00*** | (2006.01) |
| ***A61P 35/00*** | (2006.01) |
| ***G01N 33/574*** | (2006.01) |

(52) U.S. Cl.
CPC .......... *C07K 16/2803* (2013.01); *A61P 35/00* (2018.01); *G01N 33/57492* (2013.01); *A61K 2039/505* (2013.01); *C07K 2317/565* (2013.01); *C07K 2317/622* (2013.01); *C07K 2317/73* (2013.01); *C07K 2317/92* (2013.01); *G01N 2333/705* (2013.01); *G01N 2333/912* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 4,816,567 | A | 3/1989 | Cabilly et al. |
| 4,946,778 | A | 8/1990 | Ladner et al. |
| 4,965,185 | A | 10/1990 | Namen et al. |
| 4,968,607 | A | 11/1990 | Dower et al. |
| 5,011,912 | A | 4/1991 | Hopp et al. |
| 5,250,203 | A | 10/1993 | Ladner et al. |
| 5,262,522 | A | 11/1993 | Gearing |
| 5,426,048 | A | 6/1995 | Gearing |
| 5,457,035 | A | 10/1995 | Baum et al. |
| 5,530,101 | A | 6/1996 | Queen et al. |
| 5,545,806 | A | 8/1996 | Lonberg et al. |
| 5,545,807 | A | 8/1996 | Surani et al. |
| 5,585,089 | A | 12/1996 | Queen et al. |
| 5,693,761 | A | 12/1997 | Queen et al. |
| 5,693,762 | A | 12/1997 | Queen et al. |
| 5,874,299 | A | 2/1999 | Lonberg et al. |
| 5,877,397 | A | 3/1999 | Lonberg et al. |
| 6,162,963 | A | 12/2000 | Kucherlapati et al. |
| 6,181,370 | B1 | 1/2001 | Queen et al. |
| 6,255,458 | B1 | 7/2001 | Lonberg et al. |
| 6,270,964 | B1 | 8/2001 | Michnick et al. |
| 6,300,129 | B1 | 10/2001 | Lonberg et al. |
| 6,673,986 | B1 | 1/2004 | Kucherlapati et al. |
| 6,713,610 | B1 | 3/2004 | Kucherapati |
| 9,150,647 | B2 | 10/2015 | Mellstedt et al. |
| 9,228,023 | B2 | 1/2016 | Rohlff et al. |
| 9,266,952 | B2 | 2/2016 | Teige |
| 9,316,646 | B2 | 4/2016 | Rader et al. |
| 2010/0028370 | A1 | 2/2010 | Zankel et al. |
| 2010/0062005 | A1 | 3/2010 | Kipps et al. |
| 2012/0058051 | A1 | 3/2012 | Rader et al. |

(Continued)

FOREIGN PATENT DOCUMENTS

| | | |
|---|---|---|
| CN | 103429618 | 12/2013 |
| EP | 036676 | 9/1981 |

(Continued)

OTHER PUBLICATIONS

J. M. Adama et al., "The c-myc oncogene driven by immunoglobulin enhancers induces lymphoid malignancy in transgenic nice", 1985, Nature 318:533-538.

(Continued)

*Primary Examiner* — Daniel C Gamett
(74) *Attorney, Agent, or Firm* — LEX IP MEISTER, PLLC

(57) ABSTRACT

The present invention discloses an anti-ROR1 antibody specifically recognizing human and mouse ROR1. The monoclonal antibody can be usefully used for cancer targeting treatment including detection of various cancer expressing ROR1 through specific binding, and drug delivery to specific cancer, etc. as well as a cancer therapeutic agent, by inhibiting tumors.

16 Claims, 10 Drawing Sheets

Specification includes a Sequence Listing.

(56) References Cited

U.S. PATENT DOCUMENTS

| | | | |
|---|---|---|---|
| 2013/0251723 | A1 | 9/2013 | Rohlff et al. |
| 2013/0281922 | A1 | 10/2013 | Teige |
| 2014/0004156 | A1 | 1/2014 | Mellstedt et al. |

FOREIGN PATENT DOCUMENTS

| | | |
|---|---|---|
| EP | 133988 | 3/1985 |
| EP | 058481 | 10/1986 |
| EP | 088046 | 12/1987 |
| EP | 143949 | 10/1988 |
| EP | 0367566 | 5/1990 |
| EP | 546073 | 9/1997 |
| EP | 0460846 | 2/2002 |
| WO | 1996-33735 | 10/1896 |
| WO | 1990-04036 | 4/1990 |
| WO | 1991-10741 | 7/1991 |
| WO | 1993-15722 | 8/1993 |
| WO | 1994-02602 | 2/1994 |
| WO | 1994-20069 | 9/1994 |
| WO | 1999-10494 | 3/1999 |
| WO | 2005-012359 | 2/2005 |
| WO | 2008-076868 | 6/2008 |
| WO | 2010-124188 | 10/2010 |
| WO | 2012-097313 | 7/2012 |
| WO | 2016-187220 | 11/2016 |
| WO | 2017-127499 | 7/2017 |
| WO | 2017-142928 | 8/2017 |
| WO | 2017-156479 | 9/2017 |

OTHER PUBLICATIONS

Warren S. Alexander et al., "Expression of the c-myc oncogene under control of an immunoglobulin enhancer in: E mu-myc transgenic mice", Mol Cell Biol. Apr. 1987; 7(4): 1436-1444.

Ashkenazi et al., "Protection against endotoxic shock by a tumor necrosis factor receptor immunoadhesin", 1991, Proc. Natl. Acad. Sci. USA 88:10535.

Ausubel et al., Current Protocols in Molecular Biology, Greene Publishing Associates, Dec. 4, 2003, ISBN: 047150338X.

Baum et al., "Molecular characterization of murine and human OX40/OX40 ligand systems: identification of a human OX40 sgand as the HTLV-1-regulated protein gp34", 1994, EMBO J. 13:3992-4001.

Benist and Chambon, "In vivo sequence requirements of the SV40 eany promoter region", 1981, Nature 290:304-310.

Allison A. Bianchi, et al., "High-Level Expression of Full-Length Antibodies Using Trans-Complementing Expression Vectors", 2003, Biotech. Biotechnol. Bioeng. 84:439-44.

Robert E. Bird et al., "Single-Chain Antigen-Binding Proteins", 1988, Science 242:423.

James W. Bloom et al., "Intrachain disulfide bond in the core hinge region of human IgG4", 1997, Protein Science 6:407-415.

James U. Bowie et al., "A Method to Identify Protein Sequences That Fold into a Known Three-Dimensional Structure", 1991, Science 253:164-170.

Byrn et al., "Biological properties of a CD4 immunoadhesin", 1990, Nature 344:677.

Carillo et al., "The Multiple Sequence Alignment Problem in Biology", 1988, SIAM J. Applied Math. 48:1073.

Chaltie el al., "Green Fluorescent Protein as a Marker for Gene Expression", 1994, Science 263:802-805.

Chothia and Lesk, "Canonical Structure for the Hypervariable Regions of Immunoglobuline", J. Mol. Biol. 196.901-917 (1987).

Computer Analysis of Sequence Data, Part I, (Griffin, A. M., and Griffin, H. G., eds.), 1994, New Jersey: Humans Press.

Cosman et al., "Cloning, sequence and expression of human interleukin-2 receptor", 1984, Nature 312:768.

Dayhoff et al., "A Model of Evolutionary Change in Proteins", 1978, Atlas of Protein Sequence and Structure 5:345-352.

Michelle de Graaf et al., "Expression of scFvs and scFv Fusion Proteins in Eukaryotic Cells", 2002, Methods Mol Biol. 178:379-387.

Deboer et al., "The tac promoter: A functional hybrid derived from the trp and lac promoters", 1983, Proc. Natl. Acad. Sci. U.S.A. 80:21-25.

Devereux et al., "A comprehensive set of sequence analysis programs for the VAX", 1984, Nucl. Acid Res. 12:387.

Eppstein et al., "Biological activity of liposome-encapsulated murine interferon y is medisted by a cell membrane receptor", 1985, Proc. Natl. Acad. Sci. U.S.A. 82:3688-3692.

Evans et al., "Design of Nonpeptidal Ligands for a Peptide Receptor Cholecystokinin Antagonists", 1987, J. Med. Chem. 30:1229.

William E., Md. Paul, Fundamental Immunology 5th edition (Aug. 2003).

Gribskov et al., "Profile analysis: Defection of distantly related proteins", 1987, Proc. Nat. Acad. Sci. 84:4355-4358.

Grosschedi et al., "Introduction of a p Immunoglobulin Gene into the Mouse Germ Line: Specific Expression in Lymphoid Cells and Synthesis of Functional Antibody", 1984, Cell 38:647-658.

Hammer et al., "Diversity of Alpha-Fetoprotein Gene Expression in Mice Is Generated by a Combination of Separate Enhancer Elements",1987, Science 253:53-58.

Hanshan, "Heritable formation of pancreatic β-cell tumours in transgenic mice expressing recombinant insulin/simian viruss 40 oncogenes", 1985, Nature 315:115-122.

Heim et al., "Engineering green fluorescent protein for improved brightness, longer wavelengths and fluorescence resonance energy transfer", 1996, Curr. Biol. 6:178-182.

Henikoff et al., "Amino acid substitution matrices from protein blocks", 1992, Proc. Natl. Acad. Scl. U.S.A. 89:10915-10919.

Hollenbaugh et al., "Construction of Immunoglobulin Fusion Proteins", in Current Protocols in Immunology, Suppl. 4, pp. 10.19.1-10.19.11.

Holm et al., "Protein folds and families: sequence and structure alignments", 1999, Nucl. Acid. Res. 27:244-247.

Hoogenboom et al., "By passing immunisation: Human antibodies from synthetic repertoires of germline VH gene segments rearranged in vitro", J. Mol. Biol. 227:381.

Hopp et al., "A Short Polypeptide Marker Sequence Useful for Recombinant Protein Identification and Purification", 1988, Bio/Technology 6:1204.

Huston et al., "Protein engineering of antibody binding sites: Recovery of specific activity in an anti-digoxin single-chain Fv analogue produced in *Escherichia coli*", 1968, Proc. Natl. Acad. Sci. U.S.A. 85:5879.

Hye Young Yang et al., "Construction of a Large Synthetic Human scFv Library with Six Diversified CDRs and High Functional Diversity", Mol. Cells OT, 225-235, Feb. 28, 2009. DOI/10.1007/s10059-009-0028-9.

Ichiki et al., "cells in IL-4-induced human IgE production B cells in IL-4-induced human IgE production", 1993, J. Immunol. 150:5408-5417.

Weng Tao et al., "Encapsulated Cell-Based Delivery of CNTF Reduces Photoreceptor Degeneration in Animal Models of Retinitis Pigmentosa", Invest. Ophthalmol Vis Sci 43:3292-3293, 2002.

Jakobovits et al., "Germ-line transmission and expression of a human-derived yeast artificial chromosome", 1993, Nature 362:255-258.

Jakobovits et al., "Analysis of homozygous mutant chimeric mice: Deletion of the immunoglobulin heavy chain joining region blocks B-cell development and antibody production", 1993, Proc. Natl. Acad. Sci. USA 90:2551-2555.

Jakanen et al., "Intracellular Transport of Phosphatidylcholine to the Plasma Membrane", 1985, J. Cell. Biol. 101:976-985.

Jaikanen et al., "Cell Surface Proteoglycan of Mouse Mammary Epithelial Cells Is Shed by Cleavage of Its Matrix-binding Ectodomain from Its Membrane-associated Domain", 1987, J. Cell Biol. 105:3087-3096.

Jones, "Progress in protein structure prediction", Curr. Opin. Struct. Biol. 1997, 7:377-387.

(56) References Cited

OTHER PUBLICATIONS

Kelsey et al., "Species-and tissue-specific expression of human alpha 1-antitrypsin in transgenic mice.", 1987, Genes and Devel. 1:161-171.
Kohler and Milstein, "Continuous cultures of fused cells secreting antibody of predefined specificity", 1975, Nature 256:495.
Kollias et al., "Regulated expression of human Aγ-, β-, and hybrid γβ-globin genes in transgenic mice: Manipulation of the developmental expression patterns", 1986, Cell 46:89-94.
Kortt et al., "Single-chain Fv fragments of anti-neuraminidase antibody NC10 containing five- and ten-residue linkers form dimers and with zero-residue linker a trimer", 1997, Prot. Eng. 10:423.
Kortt et al., "Dimeric and trimeric antibodies: high avidity scFvs for cancer targeting", 2001, Biomol. Eng. 18:95-108.
Kostelny et al., "Formation of a Bispecific Antibody by the Use of Leucine Zippers", 1992, J. Immunol. 148:1547-1553.
Kriangkum et al., "Bispecific and bifunctional single chain recombinant antibodies", 2001, Biomol. Eng. 18:31-40.
Krumlauf et al., "Developmental regulation of alpha-fetoprotein genes in transgenic mice", 1985, Mol. Cell. Biol. 5:1639-1648.
Choi, Michael Y., et al. "Pre-clinical specificity and safety of UC-961, a first-in-class monoclonal antibody targeting ROR1." Clinical Lymphoma Myeloma and Leukemia 15 (Epub: Feb. 26, 2015): S167-S169.
Med Sci "Clin Cancer Res: Human tumor and normal organizations of ROR1 protein expression" (Jul. 3, 2017) from Balakrishnan, Ashwini, et al. "Analysis of ROR1 Protein Expression in Human Cancer and Normal Tissues." Clinical Cancer Research (Jun. 2017) dol:10.1158/1078-0432.CCR-16-2083.
AH Daneshmanesh et al., "Monoclonal antibodies against ROR1 induce apoptosis of chronic lymphocytic leukemia (CLL) cells", Leukemia (2012) 26, 1348-1355, Jan. 6, 2012; doi:10.1038/leu.2011.362.
JPO, Office Action of JP 2020-564899 dated Jan. 18, 2022.
Gohil Satyen Harish, "Pre-clinical development of novel ROR1 chimeric antigen receptor T cells and bispecific T cell engagers", Oct. 1, 2017 (Oct. 1, 2017), XP055791027.
EPO, Search Report of EP 19806701.9 dated Feb. 17, 2022.
Kyte et al., "A Simple Method for Displaying the Hydropathic Character of a Protein", 1982, J. Mol. Biol. 157:105-131.
Langer et al., 1981, "Biocompatibility of polymeric delivery systems for macromolecules", J. Biomed. Mater. Res. 15:167-277.
Lantto et al., "Chain Shuffling to Modify Properties of Recombinant Inmunoglobulins", 2002, Methods Mol. Biol. 178:303-316.
Leder et al., "Consequences of Widespread Deregulation the c-myc Gene in Transgenic Mice: Multiple Neoplasms and Nommal Development", 1986, Cell 45:485-495.
MacDonald, "Expression of the Pancreatic Elastase I Gene in Transgenic Mice", 1987, Hepatology 7:425-515.
Maniatis et al., "Regulation of Inducible and Tissue-Specific Gene Expression", 1987, Science 236:1237.
Marks et al., "By-passing Immunization Human Antibodies from V-gene Libraries Displayed on Phage", 1991, J.Mol. Bio. 222:581-597.
Marks et al., "By-Passing Immunization: Building High Afffinity Human Antibodies by Chain Shuffling", 1992, BioTechnology 10:779-783.
Mason et al., "The Hypogonadal Mouse: Reproductive Functions Restored by Gene Therapy", 1986, Science 234:1372-1378.
Magram et al., "Developmental regulation of a cloned adult β-globin gene in transgenic mice", 1985, Nature 315:338-340.
Morrison et al., "Chimeric human antibody molecules: Mouse antigen-binding domains with human constant region domains", 1985, Proc. Natl. Acad. Sci. USA 81:6851-8855.
Needleman et al., "A General Method Applicable to the Search for Similarities in the Amino Acid Sequence of Two Proteins", 1970, J. Mol. Biol. 48:443-453.
Nolan et al., "Fluorescence-activated cell analysis and sorting of viable mammalian cells based on beta-D-galactosidase activity after transduction of *Escherichia coli* lacZ.", 1988, Proc. Natl. Acad. Sel. U.S.A. 85:2603-2607.
Pikert et al., "An albumin enhancer located 10 kb upstream functions along with its promoter to direct efficient, liver-specific expression in transgenic mice", 1987, Genes and Devel. 1:268-276.
Prinster et al., "Regulation of metalothionein thymidine kinase fusion plasmids injected into mouse eggs", 1982, Nature 296:39-42.
Paul A. Sieving et al., "Ciliary neurotrophic factor (CNTF) for human retinal degeneration: Phase I trial of CNTF delivered by encapsulated cell intraocular implants", Proc. Natl. Acad. Sciences 103:3896-3901, 2006.
TE Creighton, "Proteins, Structures and Molecular Principles", 1984, W. H. New York: Freeman and Company.
Redhead et al., "Expression of a Myelin Basic Protein Gene in Transgenic Shiverer Mice: Correction of the Dysmyelinating Phenotype", 1987, Cell 48:703-712.
Rizo and Gierasch, "Constrained Peptides: Models of Bioactive Peptides and Protein Substructures", 1992, Ann. Rev. Biochem. 61:387.
Russell et al., "Structural Features can be Unconserved in Proteins with Similar Folds", J. Mol Biol., 244: 332-350 (1994).
Sambrook et al., Molecular Cloning: A Laboratory Manual, 4th ed., Cold Spring Harbor Laboratory Press, Cold Spring Harbor, N.Y. (2012).
Shani, "Tissue-specific expression of rat myosin light-chain 2 gene in transgenic mice", 1985, Nature 314:283-286.
Gribskov, M. and Devereux, J., Sequence Analysis Primer, 1991, New York: M. Stockton Press.
Sidman et al., "Controlled Release of Macromolecules and Pharmaceuticals from Synthetic Polypeptides Based on Glutamic Acid", 1983, Biopolymers 2:547-556.
Sippl et al., "Threading thrills and threats", 1998, Structure 4:15-19.
Songsivillai and Lachmann, "Bispecific antibody: a tool for diagnosis and treatment of disease", 1990, Clin. Exp. Immunol. 79:315-321.
Stauber, "Development and Applications of Enhanced Green Fluorescent Protein Mutants", 1998 Biotechniques 24:462-471.
Swift et al., "Tissue-Specific Expression of the Rat Pancreatic Elastase I Gene in Transgenic Mice", 1984, Cell 38:639-646.
Thomsen et al., "Promoter-regulstory region of the major immediate early gene of human cytomegatovirus", 1984, Proc. Natl. Acad. U.S.A. 81:659-663.
Thornton et al., "Prediction of progress at last", 1991, Nature 354:105.
Veber and Freidinger, "The design of metalbolically-stable peptide analogs", 1985, TINS p. 392.
Villa-Kamaroff et al., "A bacterial clone synthesizing proinsulin", 1978, Proc. Natl. Acad. Sci. U.S.A. 75:3727-3731.
Voss et al., "The role of enhancers in the regulation of cell-type-specific transcriptional control", 1986, Trends Biochem. Sci. 11:287.
Wagner et al., "Nucleotide sequence of the thymidine kinase gene of herpes simplex virus type 1", 1981, Proc. Natl Acad. Sci. U.S.A. 78:1444-1445.
Ward et al., "Binding activities of a repertoire of single immunoglobulin variable domains secreted from *Escherichia coli*", 1989, Nature 334:544.
Yamamoto et al., "Identification of a Functional Promoter in the Long Terminal Repeat of Rous Sarcoma Virus", 1980, Cell 22:787-797.
Aghebati et al., "Receptor tyrosine kinase-like orphan receptor 1 (ROR-1): An emerging target for diagnosis and therapy of chronic lymphocytic leukemia", 2017, Biomedicine & Pharmacotherapy 88: 814-822.
Balskrishnan, A. et al., "Analysis of ROR1 Protein Expression in Human Cancer and Normal Tissues", 2016, Clinical Cancer Research 23(12); 3061-71.
Baskar el al., "Targeting malignant B cells with an immunotoxin against ROR1", 2012, mAbs 4:349-361.
Bicocca et al., "Crosstalk between ROR1 and the pre-B-Cell Receptor Promotes Survival of t(1;19) Acute Lymphobiastic Leukemia", 2012, Cancer Cell 27:656-667.

(56) References Cited

OTHER PUBLICATIONS

Borcherding et al., "ROR1, an embryonic protein with an emerging role in cancer biology", 2014, Protein Cell, 5:496.
Cui et al., "Targeting ROR1 Inhibits Epithelial-Mesenchymal Transition and Metastasis", 2013, Cancer Res. 73:3649.
Daneshmanesh et al., "Ror1, a cell surface receptor tyrosine kinase is expressed in chronic lymphocytic leukemia and may serve as & putative target for therapy", 2008, Int. J. Cancer 123:1190.
Dave et al., "Restricted Cell Surface Expression of Receptor Tyrosine Kinase ROR1 in Pediatric B-Lineage Acute Lymphoblastic Leukemia Suggests Targetability with Therapeutic Monoclonal Antibodies", 2012, Plos One 7: e52655.
Fukuda et al., "Antisera induced by infusions of autologous Ad-CD154-leukemia B cells identify ROR1 as an oncofetal antigen and receptor for Wnt5a", Proc. Natl. Acad. Sci. 105:3047, Feb. 26, 2008.
Gentile et al., "The ROR1 pseudokinase diversifies signaling outputs in MET-addicted cancer cells", Int J Cancer. Nov. 15, 2014;135(10):2305-16.
Hudacek et al., "The B-call tumor-associated antigen ROR1 can be targeted with T cells modified to express a ROR1-specific chimeric antigen receptor", 2010, Blood 116:4532.
Branden and Tooze, "Introduction to Protein Structure", 1991, New York: Garland Publishing.
Klein et al., "Gene Expression Profiling of B Cell Chronic Lymphocytic Leukemia Reveals & Homogeneous Phenotype Related to Memory B Cells", 2001, J. Exp. Med 194:1625.
Li et al., "PKM2 methylation by CARM1 activates aerobic glycolysis to promote tumorigenesis", 2017, Nature Cell Biology.
EPO, Office Action of EP 19806701.9 dated Feb. 7, 2024.
Michael Y. Choi et al., "Pre-clinical Specificity and Safety of UC-961, a First-In-Class Monoclonal Antibody Targeting ROR1", Clinical Lymphoma Myeloma and Leukemia, vol. 15, Supplement, Jun. 2015, pp. S167-S169.
Matsuda et al., "Expression of the receptor tyrosine kinase genes, Ror1 and Ror2, during mouse development", 2001, Mech. Dev. 105:153-156.
Rebagay et al., "ROR1andROR2inhunanmalignancies:potentialsfortargetedtherapy", 2012, Prontiers in oncology, 2:1.
Rosenwald et al., "Relation of Gene Expression Phenotype to Imunoglobulin Mutation Genotype in B Cell Chronic Lymphocytic Leukemia", 2001, J. Exp. Med 194:1639.
Yamaguchi et al., "NKX2-1/TITF1/TTF-1-Induced ROR1 Is Required to Sustain EGFR Survival Signaling in Lung Adenocarcinoma", Cancer Cell 21, 348-361, Mar. 20, 2012.
Zhang et al., "The Onco-Embryonic Antigen ROR1 Is Expressed by a Variety of Human Cancers", 2012 Am J Pathol 181:1903-1910.
Zhang et al., "ROR1 Is Expressed in Human Breast Cancer and Associated with Enhanced Tumor-Cell Growth", PLoS ONE, vol. 7, Issue 3, Mar. 2012, 7:e31127.
KIPO, PCT Search Report & Written Opinion of PCT/KR2019/006213 dated Aug. 23, 2019.
KIPO, PCT Search Report & Written Opinion of PCT/KR2018/005854 dated Feb. 20, 2019.

FIG. 8

| Cancer Cell Line | | Mean Fold Ratio | Cancer Cell Line | | Mean Fold Ratio |
|---|---|---|---|---|---|
| Gastric cancer | AGS | 12.3 | Lung cancer | H460 | 10.9 |
| | NCI-N87 | 11.8 | | A549 | 6.0 |
| | MKN-28 | 4.9 | | NCI-H1975 | 4.2 |
| | SNU-1750 | 3.9 | | H1437 | 4.1 |
| | SNU-16 | 2.4 | | Calu-6 | 3.3 |
| Breast cancer | HCC1187 | 9.3 | Colon cancer | HCT116 | 18.0 |
| | MDA-MB-231 | 3.8 | | DLD-1 | 17.8 |
| | MDA-MB-468 | 6.4 | | HT29 | 3.9 |
| | HCC70 | 3.9 | ALL | 697 | 12.0 |
| | HCC1143 | 3.2 | | Kasumi-2 | 11.5 |
| | BT20 | 3.0 | MCL | Mino | 7.2 |
| | HCC1806 | 2.3 | | JeKo-1 | 4.0 |
| | HCC1937 | 2.7 | T cell leukemia | Jurkat | 1.7 |
| | BT474 | 1.7 | | | |
| | MCF7 | 1.1 | | | |

* Mean Fold Ratio : MFI of anti-ROR1 / MFI of $2^{nd}$ Ab

ANTI-ROR1 ANTIBODY AND USE THEREOF

BACKGROUND OF THE INVENTION

1. Field

Provided is an anti-ROR1 antibody or an antigen-binding fragment thereof, and its use.

2. Description of the Related Art

ROR (Receptor Tyrosine Kinase-Like Orphan Receptor) is a transmembrane protein of RTK (Receptor Tyrosine Kinase) family, and there are ROR1 and ROR2. ROR1 and ROR2 have 58% amino acid sequence identity and the theoretical molecular weight of two proteins is about 104 kDa, but the molecular weight of ROR1 is about 103 kDa, due to many N-glycosylated sites. The extracellular fdomain of ROR family consists of Ig, cysteine-rich, and kringle domain, and the intracellular domain consists of tyrosine kinase, Ser/Thr rich, proline rich domain (Borcherding et al., 2014, Protein Cell, 5:496, Rebagay et al., 2012, Prontiers in oncology, 2:1). In an aspect of biological properties, the ligand of ROR2 is Wnt5a, but the ligand of ROR1 has not been discovered yet. In addition, it is presumed that ROR2 has the kinase activity, but on the other hand, ROR1 is pseudokinase. It has been known that phosphorylation of ROR1 itself is closely related to the activity of Met (Gentile et al., 2014. Int J Cancer 15:2305).

ROR1 is expressed in the process of embryo and fetal development, and F controls cell polarity, cell migration and neurite growth, etc. The expression is gradually reduced according to progress of development, and it is hardly expressed in adults, and it is temporarily expressed in the process of development of B cell, and only little expression has been reported in adipocytes (Hudecek et al., 2010, Blood 116:4532, Matsuda et al., 2001, Mech. Dev. 105:153).

However, as the overexpression of ROR1 is observed in various cancer cells, it is classified as an oncofetal gene. In particular, ROR1 has received attention as an anti-cancer antibody target, as it is discovered that ROR1 is overexpressed in chronic lymphocytic leukemia (CLL) (Klein et al., 2001, J. Exp. Med 194:1625, Rosenwald et al., 2001, J. Exp. Med 194:1639). It has been reported as overexpressed in not only hematologic malignancy such as B-cell leukemia, lymphoma, acute myeloid leukemia (AML), Burkitt lymphoma, mantle cell lymphoma (MCL), acute lymphoblastic leukemia (ALL), Diffuse large B-cell lymphoma (DLBCL), follicular lymphoma (FL) and marginal zone lymphoma (MZL), etc. in addition to chronic lymphocytic leukemia (CLL) but also solid cancer including breast cancer, renal cancer, ovarian cancer, gastric cancer, liver cancer, lung cancer, colorectal cancer, pancreatic cancer, skin cancer, bladder cancer, testicular cancer, uterine cancer, prostate cancer, non-small cell lung cancer (NSCLC), neuroblastoma, brain cancer, colon cancer, squamous cell carcinoma, melanoma, myeloma, cervical cancer, thyroid cancer, head and neck cancer and adrenal cancer, etc. It has been known that the expression of ROR1 in such cancers is related to poor prognosis in cancer patients and affects cancer metastasis. It has been shown that the survival time is increased and the degree of metastasis is also reduced, when a cancer cell in which the expression of ROR1 is inhibited is injected to a mouse (Zhang et al., 2012 Am J Pathol. 181:1903, Zhang et al., 2015, PLOS ONE 7:e31127, Cui et al., 2013, Cancer Res. 73:3649, Baskar et al., 2013, mAbs 4:349, Yamaguchi et al., 2012, Cancer Cell 21:348, Aghebati et al., 2017, Biomedicine Et Pharmacotherapy, Balakrishnan, A. et al., 2016, Clinical Cancer Research, Li et al., 2017, Nature Cell Biology, Bicocca et al., 2012, Cancer Cell 22:656, Daneshmanesh et al., 2008, Int. J. Cancer 123:1190, Dave et al., 2012, Plos One 7: e52655, Fukuda et al., Proc. Natl. Acad. Sci. 105:3047).

Such a cancer cell-specific expression of ROR1 shows that ROR1 can be an effective cancer target, and therefore the development of an antibody specifically recognizing it is required.

U.S. Pat. No. 9,316,646 relates to an anti-ROR1 antibody, and discloses a monoclonal antibody specifically recognizing a human extracellular domain ROR1.

U.S. Pat. No. 9,266,952 relates to an antibody to ROR1 and its use, and discloses an antibody inducing CLL death, by specifically binding to a CLL cell.

Since antibodies against the same ROR1 antigen can be developed to various anti-cancer antibodies depending on properties or uses of each antibody, considering cancer-specific expression of ROR1, and its expression in various cancers, it is necessary to develop various antibodies that can replace or complement existing antibodies.

SUMMARY OF THE INVENTION

The present invention is to provide a protein, for example, an antibody or its antigen-binding fragment, which is capable of specifically recognizing ROR1.

In one aspect, the present invention provides an isolated antibody specifically recognizing an extracellular domain of ROR1 and its antigen-binding fragment and its use. In particular, the antibody may specifically recognize human ROR1, and shows cross reactivity to monkey and mouse ROR1.

In one embodiment, the antibody or antigen-binding fragment may comprise (i) heavy chain complementarity determining regions of CDRH1, CDRH2 and CDRH3, and/or (ii) light chain complementarity determining regions of CDRL1, CDRL2 and CDRL3, wherein the CDRH1 may comprise or consist essentially of any one selected from SEQ ID NOs: 1 to 5; the CDRH2 may comprise or consist essentially of any one selected from SEQ ID NOs: 6 to 13, and 96; the CDRH3 may comprise or consist essentially of any one selected from SEQ ID NOs: 14 to 21, and 97; the CDRL1 may comprise or consist essentially of any one selected from SEQ ID NOs: 22 to 29; the CDRL2 may comprise or consist essentially of any one selected from SEQ ID NOs: 30 to 37; and the CDRL3 may comprise or consist essentially of any one selected from SEQ ID NOs: 38 to 42. The term "CDRH" represents a CDR comprised in a heavy chain variable region, and the term "CDRL" represents a CDR comprised in a light chain variable region.

In this point of view, in other embodiment, the antibody or antigen-binding fragment may comprise (i) a heavy chain variable region comprising heavy chain complementarity determining regions of CDRH1, CDRH2 and CDRH3, and/or (ii) a light chain variable region comprising light chain complementarity determining regions of CDRL1, CDRL2 and CDRL3, wherein the CDRH1 may comprise or consist essentially of any one selected from SEQ ID NOs: 1 to 5; the CDRH2 may comprise or consist essentially of any one selected from SEQ ID NOs: 6 to 13, and 96; the CDRH3 may comprise or consist essentially of any one selected from SEQ ID NOs: 14 to 21, and 97; the CDRL1 may comprise or consist essentially of any one selected from SEQ ID NOs: 22 to 29; the CDRL2 may comprise or consist essentially of any one selected from SEQ ID NOs: 30 to 37; and the CDRL3 may comprise or consist essentially of any one selected from SEQ ID NOs: 38 to 42.

In other embodiment, the CDRH1, CDRH2 and CDRH3 may be a combination selected form the followings: SEQ ID NOs: 1, 6, and 14, respectively; SEQ ID NOs: 2, 7, and 15, respectively; SEQ ID NOs: 1, 8, and 16, respectively; SEQ ID NOs: 3, 9, and 17, respectively; SEQ ID NOs: 1, 10, and 18, respectively; SEQ ID NOs: 4, 11, and 19, respectively; SEQ ID NOs: 5, 12, and 20, respectively, SEQ ID NOs: 3, 13, and 21, respectively; SEQ ID NOs: 2, 96, and 15; or SEQ ID NOs: 3, 9, and 97.

In other embodiment, the CDRL1, CDRL2 and CDRL3 may be a combination selected form the followings: SEQ ID NOs: 22, 30 and 38, respectively; SEQ ID NOs: 23, 31 and 39, respectively; SEQ ID NOs: 24, 32 and 40, respectively; SEQ ID NOs: 25, 33 and 41, respectively; SEQ ID NOs: 26, 34 and 41, respectively; SEQ ID NOs: 27, 35 and 42, respectively; SEQ ID NOs: 28, 36 and 41, respectively; or SEQ ID NOs: 29, 37 and 41, respectively.

In other embodiment, the sequence of the CDRH1, CDRH2 and CDRH3; and the CDRL1, CDRL2 and CDRL3 is any one of the following combinations:

(a) CDRH1, CDRH2 and CDRH3 are SEQ ID NOs: 1, 6, and 14, respectively, and the CDRL1, CDRL2, and CDRL3 are SEQ ID NOs: 22, 30 and 38, respectively;

(b) CDRH1, CDRH2 and CDRH3 are SEQ ID NOs: 2, 7, and 15, respectively, and the CDRL1, CDRL2, and CDRL3 are SEQ ID NOs: 23, 31 and 39, respectively;

(c) CDRH1, CDRH2 and CDRH3 are SEQ ID NOs: 1, 8, and 16, respectively, and the CDRL1, CDRL2, and CDRL3 are SEQ ID NOs: 24, 32 and 40, respectively;

(d) CDRH1, CDRH2 and CDRH3 are SEQ ID NOs: 3, 9, and 17, respectively, and the CDRL1, CDRL2, and CDRL3 are SEQ ID NOs: 25, 33 and 41, respectively;

(e) CDRH1, CDRH2 and CDRH3 are SEQ ID NOs: 1, 10, and 18, respectively, and the CDRL1, CDRL2, and CDRL3 are SEQ ID NOs: 26, 34 and 41, respectively;

(f) CDRH1, CDRH2 and CDRH3 are SEQ ID NOs: 4, 11, and 19, respectively, and the CDRL1, CDRL2, and CDRL3 are SEQ ID NOs: 27, 35 and 42, respectively;

(g) CDRH1, CDRH2 and CDRH3 are SEQ ID NOs: 5, 12, and 20, respectively, and the CDRL1, CDRL2, and CDRL3 are SEQ ID NOs: 28, 36 and 41, respectively;

(h) CDRH1, CDRH2 and CDRH3 are SEQ ID NOs: 3, 13, and 21, respectively, and the CDRL1, CDRL2, and CDRL3 are SEQ ID NOs: 29, 37 and 41, respectively;

(i) CDRH1, CDRH2 and CDRH3 are SEQ ID NOs: 2, 96, and 15, respectively, and the CDRL1, CDRL2, and CDRL3 are SEQ ID NOs: 23, 31 and 39, respectively; or (j) CDRH1, CDRH2 and CDRH3 are SEQ ID NOs: 3, 9, and 97, respectively, and the CDRL1, CDRL2, and CDRL3 are SEQ ID NOs: 25, 33 and 41, respectively.

In other embodiment, the antibody or antigen-binding fragment may comprise a heavy chain variable region represented by any one selected from the group consisting of amino acid sequences of SEQ ID NOs: 43 to 50, 98 and 99.

In other embodiment, the antibody or antigen-binding fragment may comprise a light chain variable region represented by any one selected from the group consisting of amino acid sequences of SEQ ID NOs: 51 to 58.

In other embodiment, the antibody or antigen-binding fragment may comprise a combination of a heavy chain and light chain variable regions represented by the following sequence: SEQ ID NOs: 43 and 51; SEQ ID NOs: 44 and 52; SEQ ID NOs: 45 and 53; SEQ ID NOs: 46 and 54; SEQ ID NOs: 47 and 55; SEQ ID NOs: 48 and 56; SEQ ID NOs: 49 and 57; SEQ ID NOs: 50 and 58; SEQ ID NOs: 98 and 52; or SEQ ID NOs: 99 and 54.

In other embodiment, the antibody or antigen-binding fragment may be a humanized antibody, a human antibody (e.g., a complete human antibody), or antigen-binding fragment, and may have cross reactivity to monkey ROR1 and mouse ROR1. The antibody or antigen-binding fragment may be of non-naturally occurring; for example, it may be synthetic or recombinant, but not be limited thereto.

In other embodiment, the antibody may be a monoclonal antibody, in particular, a human monoclonal antibody, and may have cross reactivity to monkey ROR1 and mouse ROR1.

In other embodiment, the antibody or antigen-binding fragment may specifically recognize human ROR1, monkey ROR1 and, and/or mouse ROR1.

In other embodiment, the antibody may be in an IgG1, IgG2, IgG3 or IgG4 type. In other embodiment, the antibody or antigen-binding fragment may include Fab, Fab', $F(ab')_2$, scFab, Fv, dsFv, scFV, scFV-Fc, minibody, diabody, scAb, dAb, bivalent antibody or multivalent antibody, but not limited thereto.

In other embodiment, the present invention provides an isolated polynucleotide encoding the antibody or antigen-binding fragment.

In other embodiment, the polynucleotide may be a polynucleotide encoding at least one selected from the group consisting of heavy chain CDRs and light chain CDRs, for example, heavy chain CDRs comprising CDRH1, CDRH2, and CDRH3, and/or light chain CDRs comprising CDRL1, CDRL2, and CDRL3, as disclosed herein.

In other embodiment, the polynucleotide may be a polynucleotide encoding a heavy chain and/or light chain variable region, as disclosed herein.

In other embodiment, the polynucleotide may be a polynucleotide encoding a heavy chain and/or a light chain disclosed in the present invention.

In other embodiment, a vector comprising the polynucleotide is provided. In one embodiment, the vector comprises an expression vector for antibody production or a vector for CAR-T cell (Chimeric Antigen receptor redirected T cells) or CAR-NK (Natural killer) cell.

In other embodiment, a cell line transformed by the vector is provided.

Another embodiment provides a method of preparation of an isolated antibody specifically binding to ROR1 or its antigen-binding fragment, comprising a step of isolating an antibody or its antigen-binding fragment from the cell line.

In other embodiment, a pharmaceutical composition comprising the antibody or its antigen-binding fragment and a pharmaceutically acceptable excipient is provided.

In one embodiment, the composition is a composition for treatment and/or prevention of a disease, for example, cancer.

Another embodiment provides a method of detection of ROR1 in a biological sample, comprising a step of contacting an antibody or antigen-binding fragment thereof as described herein with a biological sample requiring detection of ROR1 expression. The method may further comprise, after the step of contacting, a step of measuring an antigen-antibody response in the biological sample treated (contacted) with the antibody or antigen-binding fragment thereof. In one embodiment, the method may be performed in vitro or in vivo.

In other embodiment, a kit comprising the antibody or its antigen-binding fragment or the composition comprising the antibody or its antigen-binding fragment is provided. As a kit, according to specific purposes that the kit is used, it can be provided as a kit for ROR1 detection or a kit for treatment of cancer, and may comprise an additional component according to its specific purpose. For example, in a kit for detection, a component for immunological analysis, for example, a buffer, or in a kit for treatment of a disease related to overexpression of ROR1, for example, cancer, an apparatus for administration and an instruction manual may be further included.

The antibody or its antigen-binding fragment may (1) specifically recognize or bind to a ROR1 which is expressed on a cell surface derived from human, mouse, or monkey or (2) specifically recognize or bind to an extracellular domain of ROR1 which is not present on a cell surface.

This antibody or its antigen-binding fragment shows an efficacy of inhibiting a cancer. In one example, when the antibody or its antigen-binding fragment is administered to a mouse tumor xenograft model, the growth of tumor is significantly inhibited. This property means that the antibodies can be usefully used for treatment of cancer. In addition, when treated to a cell line, apoptosis of an ROR1 overexpressing cancer cell line can be induced, and this also means that it can be usefully used for treatment of a cancer. This result suggests that the monoclonal antibodies show an efficacy of cancer inhibition.

In addition, the antibody can be usefully used for development of drug, etc. by having interspecific cross-binding capacity showing binding capacity to mouse ROR1. For example, the monoclonal antibody or various forms of therapeutic agents using the antibody can progress the development of drugs more economically and effectively by obtaining the initial result in a low cost of mouse model, before progressing a high cost of monkey-based experiment. Although the binding capacity to mouse ROR1 of the conventional antibody is also reported, it is observed that the degree of binding is significantly decreased, as compared to the monoclonal antibody of the present invention.

BRIEF DESCRIPTION OF THE SEVERAL VIEWS OF THE DRAWINGS

In FIG. 1, BCMA-Fc is a negative control group, and it shows that each anti-ROR1 monoclonal antibody specifically binds to the ROR1 antigen only and does not bind to BCMA protein or Fc used as a tag.

FIG. 8 is the result of measuring the binding capacity to the cell expression ROR1 antigen of the anti-ROR1 antibody prepared according to one embodiment of the present invention in various cancer cell lines (FACS). Gastric cancer cell lines (AGS, NCI-N87, MKN-28, SNU-1750, SNU-16), breast cancer cell lines (HCC1187, MDA-MB-231, MDA-MB-468, HCC70, HCC1143, BT20, HCC1806, HCC1937, BT474, MCF7), lung cancer cell lines (H460, A549, NCI-H1975, H1437, Calu-6), colorectal cancer cell lines (HCT116, DLD-1, HT29), acute lymphoblastic leukemia cell lines (697, Kasumi-2), and mantle cell lymphoma cell lines (Mino, JeKo-1), which were known as cancer forms in which ROR1 was overexpressed, was used. As the result of measurement, it was confirmed that the anti-ROR1 antibody of the present invention bound to various cancer cell lines derived from cancer forms known to be that ROR1 was overexpressed.

In FIG. 10, apoptosis was analyzed as a possible mechanism, and it was shown that the apoptosis could be induced as the antibody formed polymers as the result of treating the anti-ROR1 antibody in the cell line expressing ROR1, and the 2A2 antibody could not induce the apoptosis even despite of forming polymers.

DETAILED DESCRIPTION OF THE INVENTION

Figure 1:
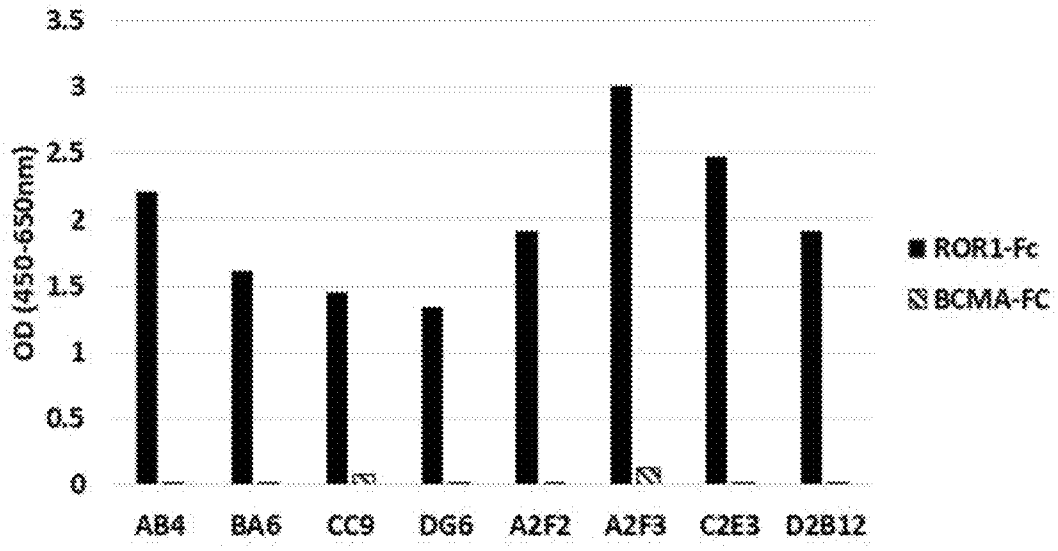
FIG. 1 is the result of analysis (ELISA) of the binding capacity to the ROR1 antigen of the anti-ROR1 monoclonal phage antibody prepared according to one embodiment of the present invention. It shows that each anti-ROR1 monoclonal antibody specifically binds to the extracellular domain ROR1 antigen.

The present invention is based on the development of an antibody which can specifically bind to ROR1.

The titles used in the present section are for convenience of specification only, and do not limit the present invention.

Unless otherwise defined herein, the scientific and technical terms used herein have the same meaning as commonly understood by those skilled in the art. Further, unless the context specifically requires, the singular includes the plural, and the plural includes the singular.

All the amino acid sequences and nucleotide sequences described herein, that are represented by specific SEQ ID NOs, may comprise, consist essentially of, or consist of not only the sequences of the specific SEQ ID NOs, but also the sequences having at least 90%, at least 92%, at least 94%, at least 95%, at least 96%, at least 97%, at least 98%, or at least 99% identity with the sequences of the specific SEQ ID NOs, so long as they maintain their activities as anti-ROR1 antibodies.

Definition

Herein, "polynucleotide" or "nucleic acid" includes a single or double strand nucleotide polymer. The nucleotide comprising such a polynucleotide may be a ribonucleotide or deoxyribonucleotide or their modified forms.

Unless otherwise stated herein, the left end of the polynucleotide stated herein is 5' end and its right end represents 3' end.

Herein, "isolated nucleic acid molecule" means DNA or RNA of genomic origin or mRNA, cDNA of synthetic origin or their combinations, which is linked to the polynucleotide that all or a portion of it is not associated with a polynucleotide present in nature, or it is not observed in nature. On the purpose of the present invention, the nucleic acid molecule comprising a specific nucleic acid sequence does not comprise an intact chromosome. Instead, the isolated nucleic acid molecule comprising a specific nucleic acid sequence may comprise at least several additional protein coding sequences, in addition to its specific sequence, or may further comprise a regulatory sequence and/or vector for expression of the specific nucleic acid sequence.

Herein, the term "regulatory sequence" means a polynucleotide sequence which can affect the expression and processing of a coding sequence by being operably connected thereto. This property of the regulatory sequence may be influenced by kinds of hosts. For example, the regulatory sequence applicable in a prokaryotic cell may include a promoter, occasionally an operator, a ribosome-binding site and a transcription termination sequence. In a eukaryotic cell, the regulatory sequence may comprise a promote comprising multiple recognition sites, a transcription enhancer, a polyadenylation sequence and a transcription termination sequence. The regulatory sequence may further comprise a reader sequence and/or a fusion partner sequence.

Herein, "vector" means any molecule used for delivering a nucleic acid molecule encoding a protein to a host cell, comprising for example, a nucleic acid, a plasmid, a bacteriophage or a virus.

Herein, "expression vector" means a vector which is suitable for transformation of a host cell and comprises a nucleic acid sequence that is operably connected to an expression vector and regulates the expression of heterologous sequences encoding a targeting protein. This expression vector may be also operably connected to the coding sequence, and in case of transcription, translation and that an intron is present, it may comprise a sequence regulating RNA splicing or affecting it.

Herein, "operably connected" means that nucleic acid sequences to be connected are positioned so as to perform a targeting function under an appropriate condition. For example, if the transcription of the coding sequence is affected by the regulatory sequence under an appropriate condition in a vector comprising a coding sequence and a regulatory sequence, it is operably connected.

Herein, "host cell" means a cell which can express a target gene that is transformed or to be transformed by a targeting nucleic acid sequence. The term includes progeny of the host cell, as long as expressing the targeting gene, regardless of identity of host cell and form and genetic makeup.

Herein, "transduction" commonly means movement of a nucleic acid from one bacterium to another bacterium by a bacteriophage. For example, it includes movement of a nucleic acid to a eukaryotic cell using a retrovirus which cannot replicate.

Herein, "transfection" means that a cell takes a foreign or exogenous DNA, and in this case, DNA is introduced in a cell through a cell membrane. This may refer methods known in the art, for example, Sambrook et al., Molecular Cloning: A Laboratory Manual, 4th ed., Cold Spring Harbor Laboratory Press, Cold Spring Harbor, N.Y. (2012), Ausubel et al., Current Protocols in Molecular Biology, Greene Publishing Associates.

Herein, "transformation" means a change of genetic properties of a cell, which are modified so that a cell comprises a new DNA or RNA. For example, a cell may be transformed as its genetic properties are changed, by introducing a new genetic material through transduction, transfection, or other techniques. The DNA transformed by methods including transduction or transfection, etc. may be present by being physically integrated in a chromosome of a cell, or may be temporarily present as an episome form without replication or a replicable plasmid. When the transformed DNA is replicated with division of a host cell, it is considered as stably transformed.

Herein, "amino acid" includes the common meaning understood in the art. Twenty natural-occurring amino acids and their abbreviations are as those commonly used in the art (Immunology-A Synthesis, 2nd Edition, E. S. Golub and D. R. Green, eds., Sinauer Associates: Sunderland, Mass. 1991). The amino acid includes typical amino acids, stereoisomers of typical 20 amino acids (D-amino acids), non-natural amino acids, for example, α-,α-disubstituted amino acids, N-alkyl amino acids, and other non-typical amino acids. As examples of non-typical amino acids, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine and other similar amino acids and imino acids (for example, 4-hydroxyproline). In the mark of polypeptide used herein, as commonly used in the art, the left of a sequence is an amino terminal and the right represents a carboxy terminal.

Herein, "polypeptide" or "protein" means a polymer of an amino acid residue, and it is used interchangeably herein. This also includes not only polymers of naturally occurring amino acid residues but also polymers of their analogues or mimetics. In addition, the polypeptide or protein may comprise modification such as addition of carbohydrates for phosphorylation or glycosylation, etc. Moreover, the polypeptide or protein may be produced in a recombinant or naturally found cell. Furthermore, the polypeptide or protein may include those in which a portion of a wild type sequence or the amino acid sequence is deleted, added and/or substituted. In addition, the polypeptide or protein includes an antibody, for example, an anti-ROR1 antibody (or named as ROR1 antibody), ROR1 binding protein, or an antigen-binding fragment, or a sequence in which one or more amino acids in the sequence are deleted, added and/or substituted. Moreover, "polypeptide fragment" means a polypeptide having an amino terminal deletion, a carboxyl terminal deletion and/or an internal deletion, compared to a full-length protein. This fragment may also include modified amino acids compared to a full-length protein. In one embodiment, the fragment may be about 5 to 500 amino acids in length, for example, at least 5, 6, 8, 10, 14, 20, 50, 70, 100, 110, 150, 200, 250, 300, 350, 400, 450, 500, 550, 600, 650, 700, 750, 800, 850 or more amino acids in length. Considering the purpose of the present invention, the useful polypeptide fragment includes an immunological functional fragment of an antibody comprising an antigen-binding domain. In case of ROR1 binding antibody, such a useful fragment includes a CDR sequence comprising 1, 2, or 3 of heavy chains or light chains, or all or a portion of antibody chain comprising a variable region or constant region of a heavy chain or light chain, but not limited thereto.

Herein, "isolated polypeptide, antibody or protein" is that there is not any other protein to be found together with them commonly and at least about 50% or more of lipids, carbohydrates and polynucleotides naturally connected to them are removed. Typically, the isolated protein, polypeptide or antibody comprises at least about 5%, at least about 10%, at least about 25% or at least about 50%, in a certain composition. This polypeptide may be encoded by genome DNA, cDNA, mRNA or other RNA of synthetic origins or any combinations thereof. In particular, the isolated protein, polypeptide or antibody is substantially free of contaminants of other proteins or other polypeptides, which interfere with its therapeutic, diagnostic and prophylactic researches or application for other uses.

Herein, "variant" of a polypeptide such as for example, an antigen-binding fragment, a protein or an antibody is a polypeptide in which one or more amino acid residues are inserted, deleted, added and/or substituted, as compared to another polypeptide sequence, and includes a fusion polypeptide. In addition, a protein variant includes one modified by protein enzyme cutting, phosphorylation or other post-translational modification, but maintaining biological activity of the antibody disclosed herein, for example, binding to ROR1 and specificity. The variant may be about 99%, 98%, 97%, 96%, 95%, 94%, 93%, 92%, 91%, 90%, 89%, 88%, 87%, 86%, 85%, 84%, 83%, 82%, 81%, or 80% identical to the sequence of the antibody or its antigen-binding fragment disclosed herein. The percent identity (%) or homology may be calculated with reference to the following description.

In one embodiment, the percent homology or identity may be calculated as 100×[(identical position)/min($TG_A$, $TG_B$)], and in the formula, $TG_A$, $TG_B$ are the sum of the number of residues of sequences A and B compared and the internal gap position (Russell et al., J. Mol Biol., 244: 332-350 (1994).

Herein, the conservative amino acid substitution means the substitution which does not substantially affect the activity or antigenicity of a polypeptide. The polypeptide may comprise one or more conservative substitutions. Non-limiting examples are disclosed in the following Table 3.

The "derivative" of the polypeptide herein means a polypeptide chemically modified in one or more residues through conjugation with other chemical moiety, which is different from an insertion, deletion, addition or substitution variant.

Herein, the term "naturally found" used with regard to a polypeptide, nucleic acid, host cell, etc. means a material present naturally.

The ROR1 (Receptor Tyrosine Kinase-Like Orphan Receptor), that is recognized by the antibody or antigen-binding fragment thereof described herein, may refer to a transmembrane protein of an RTK (Receptor Tyrosine Kinase) family. In one embodiment, it particularly recognizes an extracellular domain. The ROR1 which the antibody recognizes may be an extracellular domain which is present in a cell membrane or is not present in a cell membrane. The human protein of ROR1 consists of 937 amino acids, and the amino acid sequence is NCBI Reference Sequence ID: NP_005003.2, and the nucleic acid sequence is NM_005012.3. Unless apparent from the context used herein, the ROR1 refers to a human hROR1, but the antibody has the binding capacity to mouse ROR1 specifically. The mouse ROR1 amino acid sequence is represented by GenBank: BAA75480.1.

Herein "identity" means the sequence similarity of two or more polypeptides or two or more polynucleotides, which are determined by arranging and comparing two or more polypeptides or two or more polynucleotides. This identity between sequences is commonly represented by "identity percent", and this means the ratio of identical amino acids or nucleotides between molecules to be compared, and it is calculated on the basis of the smallest size of molecule, among molecules to be compared. The following documents may be referred for methods to be used for calculating the identity between many molecules by arranging nucleic acids or polypeptides: *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988*, SIAM J. Applied Math.* 48:1073.

When the identity percent is calculated, sequences to be compared are arranged in the way of providing the maximum matching between sequences, and in the arranged sequences, gap, matching and mis-match may be present, and this is treated by a specific mathematical model or a computer algorithm. In one embodiment, this identity percent may be determined using a GCG program package including a GAP program which arranges two sequences in the way of maximizing the match between sequences to be compared and minimizing the number of gaps, using Needleman and Wunsch algorithm (Devereux et al., 1984*, Nucl. Acid Res.* 12:387; Genetics Computer Group, University of Wisconsin, Madison, WI, USA). The computer algorithm GAP determines "matching span" by arranging two sequences in the way of maximizing the match between them and minimizing the number of gaps in two polypeptide or polynucleotide sequences to be compared. The algorithm also uses a gap opening penalty [this is calculated as 3× average diagonal, wherein "average diagonal" is the average of diagonals of comparison matrix to be used; and "diagonal" is a score or number assigned for each complete amino acid match by a specific comparison matrix] and a gap extension penalty (this is commonly 1/10 fold of the gap opening penalty), and a comparison matrix, for example, PAM 250 or BLOSUM 62 together. In a specific embodiment, a standard comparison matrix (refer to Dayhoff et al., 1978*, Atlas of Protein Sequence and Structure* 5:345-352 for PAM 250 comparison matrix; refer to Henikoff et al., 1992*, Proc. Natl. Acad. Sci. U.S.A.* 89:10915-10919 for BLOSUM 62 comparison matrix) is used. In one embodiment, parameters recommended for determining the identity percent of polypeptides or polynucleotides in which the GAP program is used are as follows: algorithm: Needleman et al., 1970*, J. Mol. Biol.* 48:443-453; comparison matrix: BLOSUM 62 (Henikoff et al., 1992, supra); gap penalty: 12 (no penalty for a terminal gap); gap length penalty: 4; similarity threshold: 0.

When two sequences are arranged using specific parameters, although there is no significant relation between two sequences, the result that they are matched with high identity in a short sequence region may be derived. In this case, in order that two sequences are arranged through at least 50 sequential amino acids, parameters of the algorithm used as the GAP program can be corrected.

"Substantially pure" used herein is that a targeting molecule is present as a predominant species. In other words, it means that on the basis of mole, the concentration is higher than any other individual species in the same mixture. In one embodiment, a substantially pure molecule is comprised as at least about 50% (based on mole), at least about 80%, about 85%, at least about 90%, or at least about 99%, among all polymers comprised in a composition. In other embodiment, the targeting molecule is substantially homogeneously purified until any more contaminants are not detected by using a conventional method, and therefore the composition comprises one kind of homogeneous polymer material.

In one aspect, the present invention relates to a recombinant antibody specifically binding to ROR1 protein or its antigen-binding fragment. In this aspect, "recombinant protein" is a protein prepared using a recombination technique, namely, through the expression of the recombinant nucleic acid described in the present invention. The methods and techniques for production of a recombinant protein are widely known in the art.

Herein, "affinity" is the strength of interaction between an antibody or its antigen-binding fragment and an antigen, and it is determined by properties of the antigen such as size, shape and/or charge of antigen, and CDR sequences of the antibody or antigen-binding fragment. The methods for determining the affinity are known in the art, and the followings can be referred.

The antibody or its antigen-binding fragment is called "specifically binding" to its target such as an antigen, when a dissociation constant ($K_D$) is $\leq 10^{-6}$ M. The antibody specifically binds to a target with "high affinity", when $K_D$ is $\leq 1\times10^{-8}$ M.

Herein, "antigen-binding region or site" means a protein or a part of protein specifically binding to a specific antigen. For example, a part of an antibody comprising an amino acid residue providing the antibody with specificity and affinity to an antigen, by interacting with the antigen. This antigen-binding region typically comprises one or more "complementary determining regions (CDR)". A specific antigen-binding region also comprises one or more "framework (FR)" regions. The framework region helps to maintain an appropriate conformation of these CDRs, thereby facilitating binding between the antigen-binding region and an antigen.

Herein, "antibody" means an antigen-binding fragment which can compete to an intact antibody for binding to any isotype of intact immunoglobulin, or a target antigen. For example, it comprises chimeric, humanized, complete human and dual-specific antibodies or their antigen-binding fragments. The antibody is one kind of antigen binding proteins by itself. The intact antibody commonly comprises at least 2 full-length heavy chains and 2 full-length light chains, but in some cases as naturally found in Camelid animals, the antibody may comprise only heavy chains. The antibody or its antigen-binding fragment may be derived from only one source or chimeric. The chimeric antibody comprises a part derived from two kinds of different antibodies, and is described in more detail below. The antibody or its antigen-binding fragment can be produced by hybridoma, recombinant DNA technique or enzymatic or chemical cutting of an intact antibody. Unless otherwise stated, herein, the term, antibody includes an antibody comprising 2 full-length heavy chains and 2 full-length light chains, and its derivatives, variants, fragments, and mutants, and their examples are as described below.

Herein, "light chain" includes a full-length light chain having a variable region sequence enough to provide binding specificity to an antigen or epitope and its fragment. The full-length light chain comprises a variable region domain VL and a constant region domain CL. The variable region domain of light chain is present in an amino terminal of a light chain polypeptide. The kinds of light chains include kappa and lambda chains. Herein, "heavy chain" includes a full-length heavy chain having a variable region sequence enough to provide binding specificity to an antigen or epitope and its fragment. The full-length heavy chain comprises a variable region domain VH and 3 constant region domains CH1, CH2 and CH3. The VH domain is present in an amino terminal of a heavy chain polypeptide and the CH domain is present in a carboxy terminal, and the CH3 is positioned closest to a carboxy terminal. The heavy chain comprises IgG (comprising IgG1, IgG2, IgG3 and IgG4 subtypes), IgA (comprising IgA1 and IgA2 subtypes), and isotypes of IgM and IgE.

Used herein, "antigen-binding fragment" of a chain (heavy chain or light chain) of an antibody or immunoglobulin includes a part of an antibody which lacks some amino acids compared to a full-length chain, but can specifically bind to an antigen. This fragment can be considered as having biological activity, in an aspect that it can specifically bind to a target antigen, or can compete to other antibodies or an antigen-binding fragment to bind a specific epitope. In one aspect, this fragment comprises at least one CDR present in a full-length light chain or heavy chain, and in some embodiments, it comprises a short-chain heavy chain and/or light chain, or its part. This biological active fragment may be produced by a recombinant DNA technique or may be produced for example, by cutting an intact antibody enzymatically or chemically. An immunologically functional immunoglobulin fragment includes Fab, Fab', F(ab')2, scFab, dsFv, Fv, scFV, scFV-Fc, diabody, minibody, scAb, and dAb, but not limited thereto, and may be derived from any mammal including human, mouse, rat, camelid or rabbit, but not limited thereto. The functional part of the antibody such as one or more CDRs described herein may be linked with a secondary protein or small molecular compound by a covalent bond, thereby being used as a target therapeutic agent to a specific target.

Herein, "Fc" region comprises two heavy chain fragments comprising CH2 and CH3 domains of an antibody. These 2 heavy chain fragments are combined each other by hydrophobic interaction of two or more of disulfide bonds and CH3 domain.

Herein, "Fab fragment" consists of 1 light chain and 1 heavy chain comprising a variable region and CH1 only. The heavy chain of Fab molecule cannot form a disulfide bond with other heavy chain molecule. scFab is one that two molecules of Fab is linked by a flexible linker.

Herein, "Fab' fragment" comprises a region between CH1 and CH2 domains of a heavy chain, in addition to Fab fragment, and it can form a disulfide bond between two heavy chains of two molecules of Fab' fragment, to form a $F(ab')_2$ molecule.

Herein, "$F(ab')_2$ fragment" comprises two light chains, and two heavy chains comprising a variable region, CH1 and a part of a constant region between CH1 and CH2 domains, as aforementioned, and thereby an intrachain disulfide bond between 2 heavy chains is formed. Thus, the $F(ab')_2$ fragment consists of two Fab' fragments, and the two Fab' fragments are meeting each other by the disulfide bond between them.

Herein, "Fv region" is a fragment of an antibody which comprises each variable region of a heavy chain and a light chain, but does not comprise a constant region. sdFV is one that a heavy chain and a light chain are linked by a disulfide bond. scFc is one that Fv is linked by a flexible linker. scFv-Fc is one that Fc is linked to scFV. The minibody is one that CH3 is linked to scFV. The diabody comprises two molecules of scFV.

Herein, "short-chain antibody (scAb)" is a single polypeptide chain comprising one variable region of a heavy chain or a light chain constant region in which a heavy chain and light chain variable region is linked by a flexible linker. The short-chain antibody may refer to for example, U.S. Pat. No. 5,260,203, and this is disclosed herein by reference.

Herein, "domain antibody (dAb)" is an immunologically functional immunoglobulin fragment comprising a variable region of heavy chain or a variable region of light chain only. In one embodiment, two or more of VH regions are linked by a covalent bond by a peptide linker, to form a bivalent domain antibody. Two VH regions of this bivalent domain antibody may target the same or different antigen.

Herein, "bivalent antigen-binding protein" or "bivalent antibody" comprises 2 antigen-binding sites. Two antigen-binding sites comprised in this bivalent antibody may have the same antigen specificity or may be a dual-specific antibody binding to different antigens separately.

Herein, "multi-specific antigen-binding protein" or "multi-specific antibody" is targeting two or more of antigens or epitopes.

Herein, "bispecific", "dual-specific" antigen-binding protein or antibody is a hybrid antigen-binding protein or antibody having 2 different antigen-binding sites. This bispecific antibody is one kind of multi-specific antigen-binding protein or multi-specific antibody, and it can be produced by known various methods, for example, methods such as fusion of hybridoma or linking of Fab' fragment. For example, Songsivilai and Lachmann, 1990, *Clin. Exp. Immunol.* 79:315-321; Kostelny et al., 1992, *J. Immunol.* 148:1547-1553, etc. may be referred. The 2 epitopes different each other to which 2 antigen-binding sites of the bispecific antigen-binding protein or antibody bind may be positioned on the same or different protein target.

Herein, the term "antigen" or "immunogen" means a molecule or a part of molecule which for example, an antigen-binding protein (for example, antibody or its immunologically functional antigen-binding fragment) can bind to, and can be used for production of an antibody which can bind to an antigen in an animal. The antigen may comprise one or more of epitopes which can interact with a different antibody or its fragment. In one embodiment, the antigen is an extracellular domain of ROR1 protein.

Herein, "epitope" is a part of molecule which is bound by an antigen-binding protein or antibody or is recognized by them, and comprise any determining factor which can specifically bind to an antigen-binding protein, such as for example, an antibody or a T-cell receptor. The epitope may be sequential or unsequential, and for example, in a polypeptide sequence, it is not sequential each other, but in an aspect of molecule, like a conformational epitope, it may be an amino acid residue that is bound by one antigen-binding protein, but is positioned away each other. In one embodiment, the epitope comprises a three-dimensional structure similar to an epitope used for antibody production, but it may be a mimetic in an aspect that it can comprise no residue found in the epitope or can comprise some residues only. Commonly, the epitope is a protein, but it may be other kinds of materials such as a nucleic acid. The epitope determining factor may be a chemically active group formed on a surface by a molecule such as an amino acid, a sugar side chain, a phosphoryl group or a sulfonyl group, or may have specific three-dimensional structural properties and/or specific charge properties. Commonly, an antibody which is specific to a specific target antigen recognizes an epitope of a target antigen which is present in a complex of a protein and/or a polymer.

Herein, "therapeutic agent" means a molecule to be administered to a subject for a targeting therapeutic effect. The subject includes a non-human mammal, for example, primates, or a human. The example of the therapeutic agent includes a protein comprising a peptide and a polypeptide, a nucleic acid, an antibody or a small molecular compound. In other aspect, the therapeutic agent can be used as a therapeutic agent of related diseases such as cancer, by being bound to the antibody, or the antibody.

Herein, the term "treating" means alleviation or treatment of an injury, disease, or symptom of disease or morbid condition, including any objective or subjective parameters, including reduction, relief, alleviation of an injury, disease, or symptom of disease or condition, or making a patient better able to withstand an injury, disease, or symptom of disease or morbid condition, slowing the deteriorating rate of an injury, disease, or symptom of disease or morbid condition, or improving the quality of life of a patient mentally or physically. This treatment or improvement of an injury, disease, or symptom of disease or morbid condition may be judged on the basis of results of physical examination, examination of various indexes related to a disease and imaging examination.

Herein, "effective dose" commonly means an amount enough to reduce seriousness and/or occurrence frequency of symptoms due to a disease, particularly, a disease related to ROR1, remove symptoms due to a disease, particularly, a disease related to ROR1 and/or a root cause of disease occurrence, or prevent occurrence of symptoms due to a disease, particularly, a disease related to ROR1 and/or a root cause, and/or improve or correct damages due to a disease, particularly, a disease related to ROR1. In some embodiments, the effective dose is a therapeutic effective dose or a prophylactic effective dose. The "therapeutic effective dose" is an amount enough to treat a disease, particularly symptoms or conditions related to ROR1, or prevent, delay a disease, particularly symptoms or conditions related to ROR1, or reverse its progress. The "prophylactic effective dose" is an amount for prevent or delay occurrence or reoccurrence of a disease, particularly, a disease related to ROR1, or symptoms related to a disease, particularly, a disease related to ROR1, and reduce its probability. The complete therapeutic or prophylactic effect can be caused by several times of administration of dose, rather than by a single administration of dose. Therefore, the therapeutic or prophylactic effective dose may be delivered by once or more of administration.

Antibody or Antigen-Binding Fragment

The present invention discloses an antibody specifically binding to an extracellular domain of ROR1 protein, or its antigen-binding fragment. The antibody is a polypeptide comprising one or more of complementary determining regions or sites (CDR), as disclosed herein.

In some embodiments, a CDR is comprised in a "framework" region, and the framework orients a CDR(s) so that this CDR(s) can have appropriate antigen-binding properties.

The antibody specifically binds to a human and mouse-derived ROR1 extracellular domain, and it can specifically bind to an isolated form of extracellular domain or an extracellular domain of ROR1 expressed on a cell surface.

The antibody disclosed herein binds to ROR1, in particular, human ROR1 and mouse ROR1. The antibody disclosed herein can specifically bind to an ROR1 extracellular domain or ROR1 expressed on a cell surface, derived from a human or mouse, and thereby it can be usefully used for target treatment of cancer targeting ROR1. For example, it can be used for treatment of a specific cancer, by combining the antibody and an anti-cancer agent. In addition, an on-target tox can be confirmed through a mouse experiment, since it binds to mouse ROR1, and in vivo efficacy can be confirmed through a syngeneic model using a mouse cancer cell line overexpressing mouse ROR1, and thereby it can be usefully used for development of various drugs related to ROR1.

In one embodiment, the antibody includes a monoclonal antibody, dual-specific antibody, double antibody, multi-specific antibody, multiple antibody, minibody, domain antibody, antibody mimetic (or synthetic antibody), chimeric antibody or antibody fusion (or antibody conjugate) and fragment thereof, but not limited thereto, and includes various forms of antibodies disclosed herein.

In one embodiment, the antibody fragment of the antibody disclosed herein may be Fab, Fab', F(ab')2, scFab, Fv, dsFv, scFV, scFV-Fc, minibody, diabody, scAb or dAb.

In other embodiment, the antibody disclosed herein may consist of a polypeptide of only light chains or only heavy chains comprising variable regions disclosed in Table 2a and Table 2b.

One antibody disclosed herein shares a specific region or sequence with another antibody disclosed herein. In one embodiment, it may share a constant region of the antibody or antigen-binding fragment. In another embodiment, it may share an Fc region. In another embodiment, it may share a frame of variable region.

In one embodiment, the antibody has a typical structure of an antibody found in nature. Camelid animals produces an antibody consisting of a single heavy chain, but the structural unit of this antibody commonly comprises a tetrameric polypeptide, and the tetramer comprises two of one pair of polypeptide chain bodies consisting of different 2 polypeptide chains. In a typical antibody, the one pair of polypeptide chain body comprises one full-length light chain (about 25 kDa) and one full-length heavy chain (about 50 to 70 kDa). Each chain shows a characteristic folding pattern, and consists of several immunoglobulin domains, consisting of about 90 to 110 amino acids. These domains are basic units consisting of an antibody polypeptide. The amino-terminal part of each chain typically comprises a part called a variable region or V region that is a part recognizing an antigen. The carboxy-terminal part is conserved evolutionarily more than the amino-terminal, and it comprises a part called a constant region or C region. The human light chain is commonly classified as kappa (κ) and lambda (λ) light chains, and these comprise one variable region and one constant region, respectively. The heavy chain is typically classified as mu (μ), delta (δ), gamma (γ), alpha (α) or epsilon (ε) chain, and these are defined as IgM, IgD, IgG, IgA and IgE isotypes, respectively. IgG includes IgG1, IgG2, IgG3 and IgG4, but has unlimited numerous subtypes. IgM subtype includes IgM and IgM2. IgA subtype includes IgA1 and IgA2. In human, IgA and IgD isotypes comprise 4 heavy chains and 4 light chains; IgG and IgE isotypes comprise 2 heavy chains and 2 light chains, and IgM isotype comprises 5 heavy chains and 5 light chains. The heavy chain constant region typically shows an effector function, but comprises one or more domains. The number of heavy chain constant region domains becomes different depending of isotypes. IgG heavy chain, for example, comprises 3 C region domains known as $C_H1$, $C_H2$ and $C_H3$, respectively. The antibody disclosed herein may be any one of these isotypes and subtypes. In one embodiment, the antibody is an IgG1, IgG2a, IgG2b, IgG3 or IgG4 subtype. In a further embodiment, the antibody of the present invention is an IgG1- or IgG2-type. In a further embodiment, the antibody of the present invention is an IgG1-type.

The heavy chain variable region and light chain variable region may be linked to at least a part of a human constant region. The selection of a constant region may be determined by whether the antibody-dependent cell-mediated cytotoxicity, antibody-dependent cell phagocytosis, and/or complement-dependent cytotoxicity is required partially.

For example, human isotype IgG1 and IgG3 have complement-dependent cytotoxicity and human isotype IgG2 and IgG4 do not have this cytotoxicity. In addition, human IgG1 and IgG3 induce a cell-mediated effector function stronger than human IgG2 and IgG4. The light chain constant region may be lambda or kappa.

In one embodiment, the antibody may be a humanized or human antibody, and the heavy chain constant region may be an IgG1-, IgG2- IgG3- or IgG4-type. In a further embodiment, the antibody of the present invention is an IgG1- or IgG2-type.

In other embodiment, the antibody is a humanized or human antibody, and recognizes mouse ROR1 specifically.

In full-length light chain and heavy chain, a variable region and a constant region are linked by "J" region that is about 12 or more of amino acids in length, and the heavy chain also comprises "D" region of about 10 or more of amino acids. For example, Fundamental Immunology, 2nd ed., Ch. 7 (Paul, W., ed.) 1989, New York: Raven Press may be referred. Typically, a variable region of light chain/heavy chain pair of an antibody forms an antigen-binding site.

A variable region of an immunoglobulin chain has the same overall structure commonly, and comprises a comparatively conserved framework region (FR) connected by 3 hypervariable regions called "complementary determining site or region or domain" or CDR (Complementary Determining Region). The CDR of a variable region derived from each chain consisting of heavy chain/light chain pair is arranged by a framework region typically, thereby forming a structure specifically binding to a specific epitope of a target protein (ROR1). These factors of naturally occurring light chain and heavy chain regions are typically comprised from the N-terminal to the C-terminal in the following order: FR1, CDR1, FR2, CDR2, FR3, CDR3 and FR4. The position of amino acid sequences corresponding to each of them in the variable region may be determined by Kabat (Kabat et al., (1983) U.S. Dept. of Health and Human Services, "Sequences of Proteins of Immunological Interest"), Chothia (Chothia and Lesk, J. Mol. Biol. 196:901-917 (1987)) or a method related to OPAL library (Hye Young Yang et. al., 2009 Mol. Cells 27: 225). The CDRs determined by each definition may be a subset which is overlapped or that one comprises the other, when comparing each other. However, herein, all CDRs to be defined by each method are included in the scope of the present invention. Those skilled in the art will easily select a CDR sequence by each definition among them, when the sequence of variable region of an antibody is provided.

CDR sequences to be comprised in heavy chain and light chain variable regions of the antibody or antigen-binding fragment according to one embodiment of the present invention are disclosed in Table 1a to Table 1f, respectively.

TABLE 1a

| Heavy Chain CDR1 | |
|---|---|
| Sequence | SEQ ID NO |
| SYDMS | 1 |
| DYYMS | 2 |
| NYDMS | 3 |
| NYAMS | 4 |
| DYDMS | 5 |

TABLE 1b

| Heavy Chain CDR2 | |
|---|---|
| Sequence | SEQ ID NO |
| WISPDSGSIYYADSVKG | 6 |
| SISPDGSNTYYADSVKG | 7 |
| WISPGGGSKYYADSVKG | 8 |
| AIYHSGSSKYYADSVKG | 9 |
| GISHGSGNKYYADSVKG | 10 |
| SISHNSGSTYYADSVKG | 11 |
| VISPDGGSIYYADSVKG | 12 |
| SISPSSGSSIYYADSVKG | 13 |
| SISPDASNTYYADSVKG | 96 |

TABLE 1c

| Heavy Chain CDR3 | |
|---|---|
| Sequence | SEQ ID NO |
| PTGRFDY | 14 |
| NLRAFDY | 15 |
| VNGRFDY | 16 |
| GGNGAWDTGFDY | 17 |
| RLSLRRRPSYYSDNAMDV | 18 |
| FISARKSLGRSYSNGMDV | 19 |
| DVVECNMNPCSYDNAMDV | 20 |
| APGWCQAPSCYYDNAMDV | 21 |
| GGNAAWDTGFDY | 97 |

TABLE 1d

| Light Chain CDR1 | |
|---|---|
| Sequence | SEQ ID NO |
| SGSSSNIGNNNVN | 22 |
| SGSSSNIGSNTVY | 23 |
| SGSSSNIGNNNVS | 24 |
| SGSSSNIGSNDVS | 25 |
| TGSSSNIGNNAVN | 26 |
| TGSSSNIGSNDVT | 27 |
| SGSSSNIGSNYVS | 28 |
| SGSSSNIGNNDVS | 29 |

TABLE 1e

| Light Chain CDR2 | |
|---|---|
| Sequence | SEQ ID NO |
| YDNKRPS | 30 |
| ANSQRPS | 31 |
| ADSHRPS | 32 |
| YDNNRPS | 33 |
| YDSNRPS | 34 |
| ADSKRPS | 35 |
| DDSHRPS | 36 |
| DDSQRPS | 37 |

TABLE 1f

| Light Chain CDR3 | |
|---|---|
| Sequence | SEQ ID NO |
| GTWDASLSGYV | 38 |
| GSWDYSLSGYV | 39 |
| ATWDYSLSGYV | 40 |
| GAWDDSLSGYV | 41 |
| GAWDDSLSGYV | 41 |
| GTWDYSLSGYV | 42 |

In one embodiment of the present invention, heavy chain and light chain variable regions of the antibody or antigen-binding fragment comprising the light chain and heavy chain CDR sequences are disclosed in the following Table 2a and Table 2b, respectively.

TABLE 2a

| Heavy Chain Variable Region (VH) Sequence | SEQ ID NO |
|---|---|
| EVQLLESGGGLVQPGGSLRLSCAASGFTFSSYDMSWVRQAPGKGLEWVS WISPDSGSIYYADSVKGRFTISRDNSKNTLYLQMNSLRAEDTAVYYCARP TGRFDYWGQGTLVTVSS | 43 |
| EVQLLESGGGLVQPGGSLRLSCAASGFTFSDYYMSWVRQAPGKGLEWVS SISPDGSNTYYADSVKGRFTISRDNSKNTLYLQMNSLRAEDTAVYYCAKN LRAFDYWGQGTLVTVSS | 44 |
| EVQLLESGGGLVQPGGSLRLSCAASGFTFSSYDMSWVRQAPGKGLEWVS WISPGGGSKYYADSVKGRFTISRDNSKNTLYLQMNSLRAEDTAVYYCAR VNGRFDYWGQGTLVTVSS | 45 |
| EVQLLESGGGLVQPGGSLRLSCAASGFTFSNYDMSWVRQAPGKGLEWVS AIYHSGSSKYYADSVKGRFTISRDNSKNTLYLQMNSLRAEDTAVYYCAR GGNGAWDTGFDYWGQGTLVTVSS | 46 |
| EVQLLESGGGLVQPGGSLRLSCAASGFTFSSYDMSWVRQAPGKGLEWVS GISHGSGNKYYADSVKGRFTISRDNSKNTLYLQMNSLRAEDTAVYYCAK RLSLRRRPSYYSDNAMDVWGQGTLVTVSS | 47 |
| EVQLLESGGGLVQPGGSLRLSCAASGFTFSNYAMSWVRQAPGKGLEWVS SISHNSGSTYYADSVKGRFTISRDNSKNTLYLQMNSLRAEDTAVYYCAKFI SARKSLGRSYSNGMDVWGQGTLVTVSS | 48 |
| EVQLLESGGGLVQPGGSLRLSCAASGFTFSDYDMSWVRQAPGKGLEWVS VISPDGGSIYYADSVKGRFTISRDNSKNTLYLQMNSLRAEDTAVYYCARD VVECNMNPCSYDNAMDVWGQGTLVTVSS | 49 |
| EVQLLESGGGLVQPGGSLRLSCAASGFTFSNYDMSWVRQAPGKGLEWVS SISPSSGSSIYYADSVKGRFTISRDNSKNTLYLQMNSLRAEDTAVYYCAKA PGWCQAPSCYYDNAMDVWGQGTLVTVSS | 50 |
| EVQLLESGGGLVQPGGSLRLSCAASGFTFSDYYMSWVRQAPGKGLEWVS SISPDASNTYYADSVKGRFTISRDNSKNTLYLQMNSLRAEDTAVYYCAKN LRAFDYWGQGTLVTVSS | 98 |
| EVQLLESGGGLVQPGGSLRLSCAASGFTFSNYDMSWVRQAPGKGLEWVS AIYHSGSSKYYADSVKGRFTISRDNSKNTLYLQMNSLRAEDTAVYYCAR GGNAAWDTGFDYWGQGTLVTVSS | 99 |

TABLE 2b

| Light Chain Variable Region (VL) Sequence | SEQ ID NO |
|---|---|
| QSVLTQPPSASGTPGQRVTISCSGSSSNIGNNNVNWYQQLPGTAPKLLIYY DNKRPSGVPDRFSGSKSGTSASLAISGLRSEDEADYYCGTWDASLSGYVF GGGTKLTVLG | 51 |

TABLE 2b-continued

| Light Chain Variable Region (VL) Sequence | SEQ ID NO |
|---|---|
| QSVLTQPPPASGTPGQRVTISCSGSSSNIGSNTVYWYQQLPGTAPKLLIYA NSQRPSGVPDRFSGSKSGTSASLAISGLRSEDEADYYCGSWDYSLSGYVF GGGTKLTVLG | 52 |
| QSVLTQPPSASGTPGQRVTISCSGSSSNIGNNNVSWYQQLPGTAPKLLIYA DSHRPSGVPDRFSGSKSGTSASLAISGLRSEDEADYYCATWDYSLSGYVF GGGTKLTVLG | 53 |
| QSVLTQPPSASGTPGQRVTISCSGSSSNIGSNDVSWYQQLPGTAPKLLIYY DNNRPSGVPDRFSGSKSGTSASLAISGLRSEDEADYYCGAWDDSLSGYVF GGGTKLTVLG | 54 |
| QSVLTQPPSASGTPGQRVTISCTGSSSNIGNNAVNWYQQLPGTAPKLLIYY DSNRPSGVPDRFSGSKSGTSASLAISGLRSEDEADYYCGAWDDSLSGYVF GGGTKLTVLG | 55 |
| QSVLTQPPSASGTPGQRVTISCTGSSSNIGSNDVTWYQQLPGTAPKLLIYA DSKRPSGVPDRFSGSKSGTSASLAISGLRSEDEADYYCGTWDYSLSGYVF GGGTKLTVLG | 56 |
| QSVLTQPPSASGTPGQRVTISCSGSSSNIGSNYVSWYQQLPGTAPKLLIYD DSHRPSGVPDRFSGSKSGTSASLAISGLRSEDEADYYCGAWDDSLSGYVF GGGTKLTVLG | 57 |
| QSVLTQPPSASGTPGQRVTISCSGSSSNIGNNDVSWYQQLPGTAPKLLIYD DSQRPSGVPDRFSGSKSGTSASLAISGLRSEDEADYYCGAWDDSLSGYVF GGGTKLTVLG | 58 |

In one embodiment, CDRs of each variable region of light chain and CDRs of each variable region of heavy chain disclosed in Table 1a to Table 1f can be combined freely.

In other embodiment, the variable regions of heavy chain and light chain disclosed in Table 2a and Table 2b can be combined freely for preparation of various forms of antibodies, and for example, a single antibody such as ScFV, or domain antibody or full-length antibody can be formed.

Each of heavy chain and light chain variable regions disclosed herein may bind to targeting various heavy chain and light chain constant regions to form heavy chain and light chain of an intact antibody, respectively. In addition, each of heavy chain and light chain sequences bound to constant regions like this may be also combined to form an intact antibody structure.

Any variable region of heavy chain and light chain of the antibody may be linked to at least a part of constant regions. The constant regions may be selected according to whether antibody-dependent cell-mediated cytotoxicity, antibody-dependent cell phagocytosis and/or complement-dependent cytotoxicity, etc. is required. For example, Human isotype IgG1 and IgG3 have complement-dependent cytotoxicity, and human isotype IgG2 and IgG4 do not have the cytotoxicity. Human IgG1 and IgG3 also induce a cell-mediated effector function stronger than human IgG2 and IgG4. For example, the heavy chain variable region may bind to a constant region of IgG, such as IgG1, IgG2, IgG2a, IgG2b, IgG3 and IgG4, and the light chain variable region may bind to a kappa or lambda constant region. For the constant region, one appropriate as desired can be used, and for example, a human or mouse-derived one can be used. In one embodiment, a human heavy chain constant region IgG1 is used, and this may be represented by the sequence of SEQ ID NO: 91. In other embodiment, as the light chain constant region, a human lambda region is used, and this may be represented by SEQ ID NO: 93.

Any variable region disclosed herein may be bound to a constant region, thereby forming heavy chain and light chain sequences. In one embodiment, the heavy chain variable region disclosed herein may be bound to a human IgG1 constant region, to form a heavy chain (full-length) comprising or consisting essentially of an amino acid sequence selected from SEQ ID NOs: 59 to 66, 100 and 101. In other embodiment, the light chain variable region disclosed herein may be bound to a human lambda constant region, to form a light chain (full-length) comprising or consisting essentially of an amino acid sequence selected from SEQ ID NOs: 67 to 74, respectively. The light chain and heavy chain can be combined as various combinations, thereby forming an intact antibody consisting of two light chains and two heavy chains.

However, such constant region sequences to be combined with the variable regions disclosed herein are exemplary, and it is clear to those skilled in the art that any other constant region selected from IgG1, IgG3, and IgG4 heavy chain constant regions, and/or any kappa or lambda light chain constant region, which are modified for stability, expression, manufacturability or other targeting properties, etc., may be also used.

The present invention comprises one or more amino acid sequences having substantial sequence identity with one or more amino acid sequences disclosed herein. The substantial identity means maintaining the effect disclosed herein in which the sequence variation is present. In one embodiment, it has about 90%, 95%, or 99% identity to the heavy chain variable regions disclosed in Table 2a. In other embodiment, it has about 90%, 95%, or 99% identity to the light chain variable regions disclosed in Table 2b. For example, in case of variant showing 90%, 95%, or 99% identity to the antibody or antigen-binding fragment disclosed herein, any variation is occurred in a frame of variable regions than CDRs.

Herein, a nucleic acid encoding the antibody or its part disclosed herein is disclosed. The nucleic acid includes a PCR or sequence analysis primer used for amplification, investigation, analysis or mutant induction of a polynucleotide encoding each chain of antibody, or fragment of the antibody, its mutant, derivative, or variant, a polynucleotide encoding a light chain or heavy chain variable region or only CDR, a polynucleotide enough to be used as a hybridization probe, and a polynucleotide encoding a polypeptide. The nucleic acids can be of any length. These may be for example, 5, 10, 15, 20, 25, 30, 35, 40, 45, 50, 75, 100, 125, 150, 175, 200, 250, 300, 350, 400, 450, 500, 750, 1,000, 1,500, 2000, or 2500 or more of polynucleotides in length and/or may comprise one or more of additional sequences, for example, regulatory sequences, and/or may be a bigger nucleic acid, for example, a part of vector. The nucleic acid may be a single strand or double strand, and may comprise RNA and/or DNA polynucleotide, and its artificial variant (e.g. peptide nucleic acid).

In one embodiment, the nucleic acid encoding the antibody or its fragment disclosed herein is a nucleic acid encoding a CDR disclosed herein, a variable region comprising the CDR, a full-length antibody comprising the variable region and constant region. When the amino acid sequence is determined, the nucleic acid sequence may be usefully determined, considering a known reverse transcription program and codon usage, etc. The exemplary nucleic acid sequence of the heavy chain constant region encoding human IgG1 may be represented by SEQ ID NO: 92. The exemplary nucleic acid sequence of the light chain constant region encoding human lambda may be represented by SEQ ID NO: 94 or 95. The exemplary nucleic acid sequence of the full-length heavy chain comprising the nucleic acid sequence of the constant regions may be selected from SEQ ID NOs: 75 to 82, 102 and 103 (heavy chain comprising a human IgG1 constant region), and the exemplary nucleic acid sequence may be selected from SEQ ID NOs: 83 to 90 (light chain comprising a human lambda constant region).

In addition, a nucleic acid sequence encoding CDR sequences of Table 1a to Table 1f, and variable regions of Table 2a and Table 2b is comprised. Since this nucleic acid sequence is included the aforementioned nucleic acid sequence encoding the full-length antibody, it is not disclosed separately, and those skilled in the art will easily confirm the nucleic acid sequence from SEQ ID NOs: 75 to 90, based on the protein sequence of CDRs and variable regions disclosed herein.

The present invention also includes one or more nucleic acid sequences having the substantial sequence identity to one or more nucleic acid sequences disclosed herein. The substantial identity means that the antibody or antigen-binding fragment encoded by the nucleic acid maintains the effect disclosed herein, even in case of causing conservative substitution or amino acid variation in which the variation of nucleic acid does not accompany amino acid substitution.

Specificity and Affinity to Antigen of Antibody

The antibody or antigen-binding fragment particularly has specificity to ECD of ROR1 antigen and appropriate affinity to be used as an antibody therapeutic agent/diagnostic agent. In one embodiment, according to Table 6, the affinity to an aggregate is $K_D<1.0\times10^{-9}$ M; in another embodiment, it is $K_D\leq1.0\times10^{-10}$ M. The antibody or antigen-binding fragment having the affinity has an advantage in that it can be administered in a lower amount of administration, compared to an antibody having low affinity, for example, $10^{-8}$ M or $10^{-9}$ M of affinity. This does not limit the antibody, for example, it, but since the enough efficacy can be obtained, despite of administration by simpler way such as subcutaneous injection, there is a big advantage clinically.

Variable Region of Antibody

The present invention relates to the antibody light chain variable region or antibody heavy chain variable region shown in Table 2a and Table 2b, and an antibody (and corresponding nucleic acid sequence) including an immunological functional fragment, a derivative, a mutant protein and a variant of the light chain and heavy chain variable regions. The antibody in which the variable regions of heavy chain and light chain are combined variously may be represented by "VHx/VLy", wherein "x" corresponds to the heavy chain variable region SEQ ID NO, and "y" corresponds to the light chain variable region SEQ ID NO. In one embodiment, the variable region may comprise the following combinations, but not limited thereto: VH43/VL51, VH43/VL52, VH43/VL53, VH43/VL54, VH43/VL55, VH43/VL56, VH43/VL57, VH43/VL58, VH44/VL51, VH44/VL52, VH44/VL53, VH44/VL54, VH44/VL55, VH44/VL56, VH44/VL57, VH44/VL58, VH45/VL51, VH45/VL52, VH45/VL53, VH45/VL54, VH45/VL55, VH45/VL56, VH45/VL57, VH45/VL58, VH46/VL51, VH46/VL52, VH46/VL53, VH46/VL54, VH46/VL55, VH46/VL56, VH46/VL57, VH46/VL58, VH47/VL51, VH47/VL52, VH47/VL53, VH47/VL54, VH47/VL55, VH47/VL56, VH47/VL57, VH47/VL58, VH48/VL51, VH48/VL52, VH48/VL53, VH48/VL54, VH48/VL55, VH48/VL56, VH48/VL57, VH48/VL58, VH49/VL51, VH49/VL52, VH49/VL53, VH49/VL54, VH49/VL55, VH49/VL56, VH49/VL57, VH49/VL58, VH50/VL51, VH50/VL52, VH50/VL53, VH50/VL54, VH50/VL55, VH50/VL56, VH50/VL57, VH50/VL58, VH98/VL51, VH98/VL52, VH98/VL53, VH98/VL54, VH98/VL55, VH98/VL56, VH98/VL57, VH98/VL58, VH99/VL51, VH99/VL52, VH99/VL53, VH99/VL54, VH99/VL55, VH99/VL56, VH99/VL57, or VH99/VL58.

The various combinations of variable regions as aforementioned may be used as an intact antibody and various forms of antibodies comprising scFV, etc.

CDR

The antibody disclosed herein is a polypeptide in which one or more CDRs are grafted, inserted and/or linked. In one embodiment, the antibody may have 1, 2, 3, 4, 5 or 6 CDRs. Thus, the antibody may have for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3").

The position of amino acid sequences corresponding a complementary determining region (CDR) and a frame region (FR) of an antibody in a variable region may be determined by Kabat (Kabat et al., (1983) U.S. Dept. of Health and Human Services, "Sequences of Proteins of Immunological Interest"), Chothia (Chothia and Lesk, J. Mol. Biol. 196:901-917 (1987)) or a method related to OPAL library (Hye Young Yang et. al., 2009 Mol. Cells 27: 225). The CDRs determined by each definition may be a subset which is overlapped or that one comprises the other, when comparing each other. However, herein, all CDRs to be defined by each method are included in the scope of the present invention. Those skilled in the art will easily select a CDR sequence by each definition among them, when the sequence of variable region of an antibody is provided.

CDRs to be comprised in the heavy chain and light chain of the antibody are disclosed in Table 1a to 1f (or heavy chain CDR1 is represented by any one selected from SEQ ID NOs: 1 to 5, and heavy chain CDR2 is represented by any one selected from SEQ ID NOs: 6 to 13 and 96, and heavy chain CDR3 is represented by any one selected from SEQ ID NOs: 14 to 21 and 97, and light chain CDR1 is represented by any one selected from SEQ ID NOs: 22 to 29, and light chain CDR2 is represented by any one selected from SEQ ID NOs: 30 to 37, and light chain CDR3 is represented by any one selected from SEQ ID NOs: 38 to 42).

An embodiment also comprises one or more amino acid sequences having substantial sequence identity with amino acid sequences of one or more CDRs disclosed in Table 1a to 1f. The substantial identity means maintaining the effect disclosed herein in which the sequence variation is present.

The structure and properties of CDR of a naturally or non-naturally occurring antibody are as aforementioned. Simply, in a typical antibody, the CDR is comprised in a framework of heavy chain and light chain variable regions consisting of a region which is involved in antigen binding and recognition. The variable region comprises 3 heavy chain CDRs and/or 3 light chain CDRs in a framework region. The CDRs may be determined and the amino acid residues may be numbered, in heavy chain and light chain, or their variable regions, according to Kabat definition (Kabat et al., (1983) U.S. Dept. of Health and Human Services, "Sequences of Proteins of Immunological Interest"), Chothia (Chothia and Lesk, J. Mol. Biol. 196:901-917 (1987)) or a method related to OPAL library (Hye Young Yang et. al., 2009 Mol. Cells 27: 225). However, the CDR disclosed herein is used for defining a typical antibody structure of antigen-binding domain, and in addition, as disclosed herein, it can be used as comprised in other various polypeptide structures.

Those skilled in the art will understand that disclosed each CDR can be selected and combined independently each other, when an antibody comprises one or more of CDRs disclosed herein. Thus, an antibody having 1, 2, 3, 4, 5 or 6 of independently selected CDRs. In addition, those skilled in the art may know that when the CDR is selected for combination, the same kind of CDR is not repeatedly used, and for example, the antibody is commonly not prepared as comprising two CDRH2 regions.

Monoclonal Antibody

The antibody disclosed herein may comprise a monoclonal antibody binding to ROR1. In particular, it comprises a human monoclonal antibody specifically recognizing ROR1, and shows cross-reactivity to human and mouse ROR1.

The monoclonal antibody may be prepared by using any technique known in the art. For example, in addition, a technique to prepare an antibody having different properties such as an antibody having various affinity to an antigen is also known. This technique is for example, chain shuffling performed by displaying an immunoglobulin variable domain gene repertory on a surface of filament bacteriophage called a phage display. For example, what is disclosed in examples herein is referred, or as an additional technique, what is disclosed in Marks et al. 1991, J. Mol. Bio. 222: 581-597; Marks et al., 1992, BioTechnology 10:779-783 may be referred.

In addition, the monoclonal antibody may be prepared by using any technique known in the art. For example, it may be produced by immortalizing splenocytes collected from an immunized transformed animal. The splenocytes may be immortalized by using any technique known in the art, for example, by fusing them with myeloma cells to produce hybridoma. The myeloma cells to be used for the hybridoma-production fusion process are preferably non-antibody-productive, have high fusion efficiency, and make them unable to grow in a specific selective medium that lacks certain enzymes and supports the growth of only the targeting fusion cells (hybridoma). The examples of appropriate cell lines to be used for mouse fusion include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul, and the examples of cell lines used for rat fusion include R210.RCY3, Y3-Ag 1.2.3, IR983F and 4B210. Other cell lines useful for cell fusion may be U-266, GM1500-GRG2, LICR-LON-HMy2 and UC729-6. In some cases, hybridoma cell lines are produced by collecting splenocytes from an animal (for example, transformed animal having a human immunoglobulin sequence, animal immunized by ROR1 immunogen); fusing collected splenocytes to myeloma cells to produce hybridoma cells; establishing hybridoma cell lines from hybridoma cells, and identifying hybridoma cell lines producing an antibody binding to ROR1. The monoclonal antibody secreted by hybridoma cell lines may be purified by using a technique known in the art.

Chimeric Antibody

The antibody can be also modified by various methods for various purposes. A chimeric antibody is an antibody forming an immunologically functional light chain, heavy chain or fragment thereof, by that polypeptide fragments derived from different antibodies are linked by covalent bonds. Commonly, a part of light chain and/or heavy chain of the chimeric antibody is a sequence belongs to a certain species or certain class or subtype, and the rest sequence belongs to other species or other class or subtype. For a method of preparation of a chimeric antibody, for example, U.S. Pat. No. 4,816,567; and Morrison et al., 1985, *Proc. Natl. Acad. Sci. USA* 81:6851-6855 may be referred. For CDR grafting, for example, U.S. Pat. Nos. 6,180,370, 5,693,762, 5,693,761, 5,585,089 and 5,530,101 may be referred.

Commonly, a purpose for preparing a chimeric antibody is to maximize the number of amino acids found in an organism in which an antibody is used. One example is a "CDR-grafted" antibody, wherein the antibody comprises one or more of CDRs derived from a certain species, or certain class or subtype, and the rest part is derived from other species, or other class or subtype antibody. For example, to use it to human, a naturally appearing variable region or CDR of human antibody by that a variable region or selected CDR of rodent antibody is grafted in the human antibody may be replaced or vice versa.

In addition, in one embodiment, for a constant region derived from species other than human, a hybrid antibody combined with a variable region derived from human may be used.

Complete Human Antibody

Herein, a complete human antibody is also disclosed. A complete human antibody specific to certain antigen can be prepared without exposing human to an antigen.

The complete human antibody may be also derived from a phage-display library (Hoogenboom et al., 1991, *J. Mol. Biol.* 227:381; and Marks et al., 1991, *J. Mol. Biol.* 222:581). The phage display technique is a method mimicking a kind of immune selection which displays an antibody repertory on a surface of filamentous bacteriophage and therefrom, sorts a phage binding to a targeting antigen. This one technique may refer to examples herein or PCT laid-open publication No. WO 99/10494. In one embodiment, the complete human ROR1 antibody of the present invention is sorted through the phage display method. This technique may refer to for example, examples herein or PCT laid-open publication No. WO 2005/012359.

Other method producing a complete human antibody is "humanizing" a mouse humoral immune system. An endogenous Ig gene may introduce human immunoglobulin (Ig) genetic loci to a non-activated mouse, thereby producing a complete human monoclonal antibody (mAb) in the mouse.

If using the complete human antibody, an immunogenic reaction and allergic reaction which may be caused by administering a mouse or mouse-derived mAb into human may be minimized. This complete human antibody may be produced by immunizing a transformed animal (commonly, mouse) which can produce a human antibody by lacking production of an endogenous immunoglobulin. An antigen for this purpose typically has 6 or more of sequential amino acids, and randomly, is conjugated to a carrier, for example, hapten. For example, the followings may be referred: Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. As one example, in this method, the transformed animal is produced by incapacitating endogenous mouse immunoglobulin gene loci encoding mouse heavy and light chain immunoglobulin chains and inserting a loci fragment comprising a human genome DNA encoding human heavy chain and light chain proteins. By cross-mating a partially modified mouse partially comprising human immunoglobulin genetic loci, a mouse in which the complete human immunoglobulin gene loci are introduced is produced. When an immunogen is administered to the animal, an antibody which is immunospecific to the immunogen, but comprises a variable region has a human amino acid sequence not murine. This method refers to for example, WO96/33735 and WO94/02602. A method related to a transformed mouse to prepare a human antibody may refer to U.S. Pat. Nos. 5,545,807; 6,713,610; 6,673,986; 6,162,963; 5,545,807; 6,300,129; 6,255,458; 5,877,397; 5,874,299 and 5,545,806; WO91/10741, No. WO90/04036, and EP No. 546073B1.

Various Forms of Antibodies

The antibody disclosed herein is also a variant of the antibody disclosed herein. For example, a part of antigen comprises conservative amino acid substitution in one or more of residues of the heavy chain or light chain, variable region or CDR sequence disclosed above. The conservative amino acid substitution means substitution which does not substantially affect the activity of a polypeptide or antigenicity. In one embodiment, the conservative amino acid substitution refers to substitution to other residues which belongs to the same classification among the following amino acid classification. Naturally-occurring amino acids may be classified on the basis of common properties of side chain properties as follows: 1) hydrophobic: norleucine, Met, Ala, Val, Leu, Ile; 2) neutral, hydrophilic: Cys, Ser, Thr, Asn, Gln; 3) acidic: Asp, Glu; 4) basic: His, Lys, Arg; 5) residue affecting a chain direction: Gly, Pro; and 6) aromatic: Trp, Tyr, Phe. The conservative amino acid substitution may also comprise a non-naturally-occurring amino acid residue such as a peptide mimetic, and this residue is typically introduced by chemical synthesis, not a cell.

Unlimited exemplary examples of conservative amino acid substitution are shown in Table 3, but not limited thereto.

TABLE 3

| Conservative amino acid substitution | |
|---|---|
| original residue | Exemplary subsititution |
| Ala | Ser |
| Arg | Lys |
| Asn | Gln, His |
| Asp | Glu |
| Cys | Ser |
| Gln | Asn |

TABLE 3-continued

| Conservative amino acid substitution | |
|---|---|
| original residue | Exemplary subsititution |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Non-conservative substitution includes substitution to a residue which belongs to other classification among the above classification. This substitution may be introduced in a region of an antibody which is homologous to a human antibody or a non-5 homologous region.

For introducing this substitution, in one embodiment, an index showing hydrophobicity or hydrophilicity of an amino acid (hydropathic index) may be considered. The index profile of a protein (hydropathic profile) is calculated by designating the index for each amino acid, and then repeatedly averaging these values. The indexes of each 10 amino acid is designated on the basis of hydrophobicity and charge property as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

For giving an interactional biological function to a protein, the importance of index profile is known in the art (Kyte et al., 1982, *J. Mol. Biol.* 157:105-131). It is known that a specific amino acid may be substituted with other amino acid having a similar numerical value index or score, and the similar biological activity may be maintained. In one embodiment, for performing a change based on the index, the substitution in which the index is in ±2, in ±1, or in ±0.5 is included.

In addition, substitution between similar amino acids, in particular, when a protein produced by substitution is a protein having activity immunologically as described herein, may be performed on the basis of hydrophilicity. In one embodiment, the maximum local average hydrophilicity value of a protein, which is determined by hydrophilicity of a close amino acid, is related to biological properties of a protein such as immunogenicity and antigen-binding property.

The hydrophilicity values of amino acid residues are as follows: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In case of substitution based on similar hydrophilicity values, in one embodiment, substitution of amino acids of which hydrophilicity values are in ±2, in ±1, or in ±0.5 is included. In addition, an epitope may be identified from the primary amino acid sequence on the basis of hydrophilicity. In addition, these regions are called "epitope core regions".

Those skilled in the art will determine an appropriate variant of the polypeptide disclosed herein using a known technique. Those skilled in the art will find a site which can change a protein without destroying the activity, by targeting a region that is not considered important for activity in the polypeptide. Those skilled in the art will also identify a residue or part to be conserved between similar polypeptides. In addition, in other embodiment, for a part considered as important for biological activity or structure, the conservative amino acid substitution may be performed, without destroying biological activity, or negatively affecting a polypeptide structure.

Moreover, those skilled in the art may perform a structural-functional analysis to identify a residue important for activity or structure in a similar polypeptide. Through this analysis, an important amino acid residue in a targeting protein may be predicted by finding a residue corresponding to an important amino acid residue for activity or structure of a protein similar to it, in one protein. Those skilled in the art may substitute the important amino acid residue predicted on this wise to an amino acid chemically similar to it.

Those skilled in the art, in addition, may predict an amino acid residue related to a three-dimensional structure of an antibody based on the three-dimensional structure of a similar polypeptide and amino acid sequence analysis related to it. Those skilled in the art do not introduce a rapid change, since the amino acid residue predicted as present on a surface of a protein may be involved in an important interaction with another molecule. Moreover, those skilled in the art may produce test variants comprising substitution of a single amino acid in each targeting amino acid residue. These variants then, are screened by using the binding capacity to an antigen, thereby collecting information as to which amino acid substitution matches the purpose. Using this information, those skilled in the art may easily determine a position to be substituted or a position to be avoided.

In addition, a position to be substituted may be determined on the basis of secondary structure of a protein. For example, one method of predicting the secondary structure is based on homology modeling. For example, 2 polypeptides or proteins having more than 30% of sequence identity or more than 40% of similarity may have similar structural phases (Holm et al., 1999, *Nucl. Acid. Res.* 27:244-247). For additional methods of predicting the secondary structure, "threading" (Jones, 1977, *Curr. Opin. Struct. Biol.* 7:377-387; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (Holm, 1999, ibid; and Brenner, 1997, ibid) are included.

In some embodiments, amino acid substitution performs (1) reducing sensitivity to protein decomposition, (2) reducing sensitivity to oxidation, (3) modifying binding affinity for forming a protein complex, (4) modifying antigen binding affinity and/or (5) modifying so as to provide a protein with other physicochemical or functional properties. For example, substitution of single or multiple amino acids including conservative substitution may perform substitution in not a domain which is involved in an intermolecular contact, but other parts. In this embodiment, the conservative amino acid substitution that does not substantially change structural properties of a parent sequence, for example, substitution to one or more of amino acids which does not change the secondary structure of the antibody, may be used. Examples of secondary and tertiary structures of polypeptides known in the art may refer to Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et al., 1991, *Nature* 354:105).

In additional preferable antibody variants, a variant in which one or more of cysteine residues are deleted, or the cysteine residues are substituted to other amino acids such as serine, in a parent sequence is included. The cysteine variant is, in particular, a structure in which an antibody has biological activity, and it is useful when needed to be folded again. The cysteine variant may have small number of cysteine residues compared to a parent antibody, and commonly, may be comprised in an even number in order to minimize interaction due to cysteines without a pair.

The heavy chain and light chain, variable region domain and CDR disclosed herein may be used for preparing a polypeptide comprising an antigen-binding region which can specifically bind to ROR1. For example, one or more of CDRs disclosed in Table 1a to Table 1f may be non-covalently or covalently bound to a molecule like a polypeptide, and thereby they may be used as an immunogenic adhesion molecule. This immunogenic adhesion molecule may be that a CDR is integrated in a big polymer, or that a CDR is linked to another polypeptide. This immunogenic adhesion molecule allows specific binding to an antigen targeting a polypeptide linked thereto or other material, for example, ROR1 or an epitope.

A peptide mimetic based on the variable region and CDR disclosed herein is also provided. This mimetic may be a peptide, non-peptide or combination of peptide and non-peptide, and the followings may be referred: Fauchere, 1986, *Adv. Drug Res.* 15:29; Veber and Freidinger, 1985, *TINS* p. 392; and Evans et al., 1987, *J. Med. Chem.* 30:1229. A peptide mimetic structurally similar to one useful polypeptide has a similar effect to the original polypeptide. This compound may be developed by using a computerized molecular modeling. Commonly, the peptide mimetic is structurally similar to an antibody showing specifically binding capacity to ROR1 herein, but one or more of peptide bonds may be replaced with bonds selected from $-CH_2NH-$, $-CH_2S-$, $-CH_2-CH_2-$, $-CH-CH-$ (cis and trans), $-COCH_2-$, $-CH(OH)CH_2-$ and $CH_2SO-$, by a method widely known in the art. For production of a more stable protein, one or more of residues of a conservative sequence may be substituted to the same type of D-amino acid (for example, D-lysine instead of L-lysine). In addition, a molecule which can cyclize a peptide may introduce a crosslink forming cysteine residue on the inside, thereby producing a peptide structurally imposing restrictions to a conservative sequence (Rizo and Gierasch, 1992, *Ann. Rev. Biochem.* 61:387).

The present invention also provides a derivative of the antibody disclosed herein. The derivatized antibody may comprise any molecule or material providing targeting properties, for example, an increased half-life in certain uses to the antibody or its fragment. The derivatized antibody may comprise a detectable (or labeling) residue (e.g.: molecule binding to a radioactive, colorimetric, antigenic, or enzyme molecule, detectable bead (e.g.: magnetic or electron-dense (e.g.: gold) bead), or other molecules (e.g.: biotin or streptavidin)), a therapeutic or diagnostic residue (e.g.: radioactive, cytotoxic, or pharmaceutically active residue), or a molecule increasing suitability of the antibody for special uses (for example, administration to a subject, for example, a human subject, or other in vivo or in vitro uses). For examples of a molecule to be used for derivatizing an antibody, albumin (e.g.: human serum albumin) and polyethylene glycol (PEG) are included. The albumin-linked and pegylated derivatives of the antibody may be prepared by using techniques widely known in the art. In one embodiment, a pegylated single chain polypeptide is comprised. In another embodiment, the antibody may be conjugated or linked to transthyretin (TTR) or TTR variant. The TTR or TTR variant may be chemically modified by chemical materials selected from the group consisting of for example, dextran, poly(n-vinyl pyrrolidone), polyethylene glycol, propropylene glycol homopolymer, polypropylene oxide/ethylene oxide copolymer, polyoxyethylated polyol and polyvinyl alcohol.

Other derivatives include a covalent or agglomerating conjugate of an ROR1 binding protein and other protein or polypeptide, which can be prepared for example, by expression of a recombinant fusion protein comprising a heterogeneous polypeptide fused in N-terminal or C-terminal of ROR1 protein. For example, the conjugated peptide may be a heterogeneous signal (or reader) polypeptide, for example, a yeast alpha-factor reader, or a peptide, for example, an epitope tag. The ROR1 antibody-comprising fusion protein may comprise a peptide added to make purification or identification of ROR1 binding protein (e.g.: poly-His) easy. The ROR1 binding protein may be also linked to FLAG peptide as described in Hopp et al., 1988, *Bio/Technology* 6:1204; and U.S. Pat. No. 5,011,912. The FLAG peptide has excellent antigenity, and therefore acts as an epitope to be reversibly bound by a specific monoclonal antibody (mAb), thereby allowing rapid confirmation and easy purification of a recombinant protein.

In one embodiment, it relates to an oligomer comprising multiple ROR1-binding polypeptides to be bound through covalent or non-covalent interaction between peptide residues fused to the ROR1 binding protein. This peptide to be bound may be a peptide such as a peptide linker (spacer) or a leucine zipper having a property of facilitating oligomerization. In one embodiment, the oligomer comprises 2 or 4 of ROR1 binding proteins. The ROR1 binding protein residue of the oligomer may be aforementioned any form, for example, a variant or fragment. Preferably, the oligomer comprises an ROR1 binding protein having ROR1 binding activity.

In one embodiment, the oligomer is prepared by using a polypeptide derived form an immunoglobulin. The preparation of a fusion protein comprising heterogeneous polypeptides fused to various sites (including an Fc domain) of an antibody-derived polypeptide may refer to for example, Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in Current Protocols in Immunology, Suppl. 4, pages 10.19.1-10.19.11.

Other embodiment relates to a dimer comprising 2 fusion proteins in which the ROR1 binding protein is fused to a Fc region of an antibody. The dimer may be prepared by inserting a gene fusion encoding a fusion protein into an appropriate expression vector, expressing the gene fusion in a host cell transformed by a recombinant expression vector, and allowing the expressed fusion protein to combine similarly to an antibody molecule, and in this regard, a disulfide bond between chains is formed between Fc residues to collect the dimer.

The term "Fc polypeptide" used herein is a polypeptide derived from an Fc region of an antibody, and includes a wildtype or mutant form. A cut form of polypeptide comprising a hinge region which facilitates dimerization is also included. The fusion protein comprising an Fc residue or oligomer formed therefrom have an advantage of being separated easily with an affinity chromatography using a protein A or protein G column.

For examples of appropriate Fc polypeptides, there are those described in U.S. Pat. Nos. 5,426,048 and 5,262,522, 5,457,035 and Baum et al., 1994, *EMBO J.* 13:3992-4001. In the amino acid sequence of this mutant protein, the wildtype amino acid $19^{th}$ residue is substituted from Leu to Ala, and the amino acid $20^{th}$ residue is substituted from Leu to Glu, and the amino acid $22^{th}$ residue is substituted from Gly to Ala. In the mutant protein, the affinity to an Fc receptor is reduced.

In other embodiment, the variable region of heavy chain and/or light chain of ROR1 binding protein disclosed herein may be substituted and enter a variable region of heavy chain and/or light chain of another antibody.

Label and Effector Groups

In some embodiments, the antibody or antigen-binding fragment may comprise one or more of labels. "Label" means any detectable material. For examples of appropriate label groups, a radioactive isotope or radioactive nuclide (e.g.: $^{3}H$, $^{14}C$, $^{15}N$, $^{35}S$, $^{90}Y$, $^{99}Tc$, $^{111}In$, $^{125}I$, $^{131}I$), a fluorescent group (e.g.: FITC, rhodamine, lanthanoid fluorescent substance), an enzyme group (e.g.: horse radish peroxidase, β-galactosidase, luciferase, alkaline phosphatase), a chemiluminescent group, a biotinyl group, or certain polypeptide epitope recognized by a secondary reporter (for example, leucine zipper pair sequence, secondary antibody binding site, metal binding domain, epitope tag) is included, but not limited thereto. In some embodiments, the labeling group is coupled to an antibody through various length of space arms to reduce potential steric hindrance. Various methods to label a protein are known in the art, and those skilled in the art will select an appropriate label and a proper method for a specific purpose.

The term "effector group" is a material to be coupled or conjugated to an antibody or synthetic material. In one embodiment, the synthetic material means any material functioning for treatment. In one embodiment, examples of appropriate materials for treatment include radioactive materials for treatment such as a radioactive isotope or radioactive nuclide (e.g.: $^{3}H$, $^{14}C$, $^{15}N$, $^{35}S$, $^{90}Y$, $^{99}Tc$, $^{111}In$, $^{125}I$, $^{131}I$). As other proper examples, a cytotoxic agent or anti-cancer agent is included, and for example, paclitaxel, docetaxel, auristatin, geldanamycin, auristatin, geldanamycin, maytansine, anthracycline derivative, Calicheamicin, Duocarmycin, Camptothecin, amanitin, pyrrolobenzodiazepines (PBD) dimer, 1-(Chloromethyl)-2,3-dihydro-1H-benzo[e]indole (CBI) dimer and CBI-PBD heterogeneous dimer are included, but not limited thereto. In some embodiments, the effector group is coupled to an antibody through various length of spacer arms to reduce potential steric hindrance.

Commonly, labels may be classified according to detection methods: a) radioactive or isotope label; b) magnetic label (e.g.: magnetic particle); c) oxidation-reduction active residue; d) optical dye; enzyme group (for example, horse radish peroxidase, β-galactosidase, luciferase, alkaline phosphatase); e) biotinyl group; and f) certain polypeptide epitope recognized by a secondary reporter (e.g.: leucine zipper pair sequence, binding site for a secondary antibody, metal binding domain, epitope tag, etc.). In some embodiments, the labeling group is coupled to an antibody through various length of spacer arms to reduce potential steric hindrance. Various methods for labeling a protein are known in the art.

In one embodiment, the label comprises an optical dye comprising a chromophore, a phosphor and a fluorescent substance, but not limited thereto. The fluorescent substance may be a small-molecular fluorescent material or protein fluorescent material.

"Fluorescent label" means any molecule to be detected by fluorescent properties which a material has. For examples of the fluorescent label, fluorescein, rhodamine, tetramethyl-rhodamine, eosin, erythrosine, coumarin, methyl-coumarin, pyrene, malachite green, stilbene, lucifer yellow, cascade blue J, texas red, IAEDANS, EDANS, BODIPY FL, LC red 640, Cy 5, Cy 5.5, LC red 705, oregon green, alexa-fluor dye (alexa-fluor 350, alexa-fluor 430, alexa-fluor 488, alexa-fluor 546, alexa-fluor 568, alexa-fluor 594, alexa-fluor 633, alexa-fluor 647, alexa-fluor 660, alexa-fluor 680), cascade blue, cascade yellow and R-phycoerythrin (PE), FITC,), Cy5, Cy5.5, and Cy7 etc. are included, but not limited thereto. Various optical dyes may refer to Molecular Probes Handbook, Richard P. Haugland.

The protein fluorescent label substances include green fluorescent proteins including *Renilla, Ptilosarcus* or *Aequorea* species of GFP (Chalfie et al., 1994, *Science* 263:802-805), EGFP (Clontech Labs., Inc., Genbank Accession Number U55762), blue fluorescent proteins (BFP, Quantum Biotechnologies, Inc., Quebec, Canada; Stauber, 1998 *Biotechniques* 24:462-471; Heim et al., 1996, *Curr. Biol.* 6:178-182), enhanced yellow fluorescent proteins (EYFP, Clontech Labs., Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607), but not limited thereto.

Nucleic Acid

In one aspect, the present invention relates to a nucleic acid confused to the nucleic acid disclosed herein under a specific hybridization condition. The hybridization method of the nucleic acid is widely known in the art. For example, Current Protocols in Molecular Biology, John Wiley & Sons, N.Y. (1989), 6.3.1-6.3.6 may be referred. Herein, a strict hybridization condition uses pre-washing solution comprising 5× sodium chloride/sodium citrate (SSC), 0.5% SDS, 1.0 mM EDTA (pH 8.0); a hybridization buffer of about 50% formamide, 6×SSC, and a hybridization temperature of 55° C. (or other similar hybridization solution, for example, a solution comprising about 50% formamide, a hybridization temperature of 42° C., and a washing condition of 60° C. in 0.5×SSC, 0.1% SDS. The strict hybridization condition is hybridization by 6×SSC at 45° C., and then 0.1×SSC at 68° C., and one or more of washing in 0.2% SDS. Further, those skilled in the art will select proper hybridization conditions required so that a nucleic acid comprising at least 65%, 70%, 75%, 80%, 85%, 90%, 95%, 98% or 99% identical nucleotide sequences between sequences typically maintains a state hybridized each other.

Basic parameters affecting selection of hybridization conditions and appropriate conditions may refer to for example, Sambrook, Fritsch, and Maniatis, (2001, Molecular Cloning: A Laboratory Manual, Cold Spring Harbor Laboratory Press, Cold Spring Harbor, N.Y., above; and Current Protocols in Molecular Biology, 1995, Ausubel et al., eds., John Wiley & Sons, Inc., section 2.10 and 6.3-6.4. These conditions may be easily determined by those skilled in the art, based on for example, the length and/or base composition (configuration of A, G, C and T (U)) of the nucleic acid, etc.

The nucleic acid disclosed herein also includes a mutant variant. A change in an amino acid sequence of a polypeptide (antibody or antibody derivative) which the nucleic acid encodes may be induced by mutation in the nucleic acid. The mutant may be introduced by using any technique known in the art. For example, a site-directed mutagenesis method, a random mutagenesis method may be used. The nucleic acid mutant prepared likewise is sorted for a polypeptide having targeting properties.

Without significantly changing biological activity of a polypeptide encoded by the nucleic acid, the mutant may be introduced in the nucleic acid. For example, nucleotide substitution which causes amino acid substitution in a non-essential amino acid residue may be performed. Alternatively, one or more mutants which selectively change biological activity of a polypeptide encoded by the nucleic acid may be introduced in the nucleic acid. For example, the mutant may change biological activity quantitatively or qualitatively. The examples of quantitative changes include increase, decrease or removal of activity. The examples of qualitative changes include a change of specificity to an antigen of an antibody.

In addition, without changing an amino acid sequence of a polypeptide encoded by the nucleic acid, for example, variation for codon optimization for intracellular expression may be introduced in the nucleic acid. In this case, due to degeneracy of codon, numerous nucleic acids encoding the same polypeptide may be prepared.

The nucleic acid encoding any antibody or its fragment disclosed herein may be mutated so that the amino acid sequence is modified, by using a molecular biology technique widely known in the art.

In other aspect, in addition, the present invention relates to a nucleic acid molecule proper to be used as a primer or hybridization probe for detection of the nucleic acid sequence disclosed herein. This nucleic acid may comprise a part of full-length nucleic acid sequence, for example, a fragment of a nucleic acid encoding a full-length polypeptide, or fragment nucleic acid encoding an active part (ROR1 binding part) of a polypeptide, to be used as a probe or a primer.

The primer and probe prepared based on the nucleic acid sequence may be used for detecting a transcriptome encoding the nucleic acid disclosed herein or similar nucleic acid, or polypeptide. In one embodiment, this probe may be used for identifying a cell expressing the polypeptide. The primer or probe may be labeled by a label material such as a radioactive isotope, fluorescent compound, enzyme or enzyme cofactor.

In other aspect, in addition, the present invention provides a vector comprising a nucleic acid encoding the polypeptide or its part (for example, fragment comprising one or more of CDRs or one or more of variable region domains). The examples of the vector include a plasmid, virus vector, non-episome mammal vector and (recombinant) expression vector, etc., but not limited thereto. The recombinant expression vector may comprise a suitable form of nucleic acid for expression of nucleic acid in a host cell. The recombinant expression vector comprises one or more of regulatory sequences based on a host cell to be used for expression, and these regulatory sequences are operably connected to a nucleic acid sequence to be expressed. In the regulatory sequence, for example, SV40 initial gene enhancer, promoter such as Rous sarcoma virus promoter and cytomegalovirus promoter, which can control expression of a nucleotide sequence in various kinds of host cells; or for example, tissue-specific regulatory sequence, which controls expression of a nucleotide sequence only in a specific host cell (Voss et al., 1986, *Trends Biochem. Sci.* 11:287, Maniatis et al., 1987, *Science* 236:1237), and metallothionein promoter working in a mammal cell, and tet-reactive and/or streptomycin reactive promoter working in both prokaryote and eukaryote systems, which instructs inductive expression of a nucleotide sequence by responding to special treatment or conditions, are included. Those skilled in the art will select an appropriate vector and a regulatory sequence, considering factors such as kinds of a host cell to be transformed, expression degree of a targeting protein. The selected expression vector may be delivered in a host cell and may be used for production of a protein encoded by the nucleic acid disclosed herein.

In other aspect, the present invention provides a host cell in which a recombinant expression vector is introduced. The host cell may be any prokaryote (for example, *E. coli*) or eukaryote (for example, yeast, insect, or mammal cell). The vector DNA may be introduced in a prokaryotic or eukaryotic cell through a known transformation or transfection technique. It is known that in case of stable transfection in a mammal cell, depending on kinds of expression vector used and transformation techniques, only small number of cells can integrate DNA delivered by transfection in its genome. Thus, to identify and select a transfected cell, commonly a gene encoding a selectable marker such as an antibiotic resistant marker is introduced into a host cell together with a targeting gene. For preferable selectable markers, drugs, for example, those providing resistance to for example, G418, hygromycin and methotrexate are included. The sorting of a cell in which a targeting nucleic acid is stably introduced may be achieved by selecting a survived cell only through drug treatment.

Treatment Method, Pharmaceutical Formulation

A treatment method using an antibody is also provided. In one embodiment, the antibody is provided to a patient. The antibody binds to human ROR1 expressed on a cancer cell surface, thereby inhibiting metastasis of a cancer cell. In one embodiment, the antibody binds to human ROR1 expressed on a cancer cell surface in a combined form with a cytotoxic agent, thereby specifically delivering the cytotoxic agent combined to the antibody to the cancer cell, to induce the death of the cancer cell. In one embodiment, the antibody is expressed on a surface of a cytotherapeutic agent such as CAR-T, etc., and the antibody binds to human ROR1, thereby specifically delivering the cytotherapeutic agent to the cancer cell, to induce the death of the cancer cell.

A pharmaceutical composition comprising a therapeutically effective dose of the antibody and a pharmaceutically acceptable diluent, carrier, solubilizer, emulsifier, preservative and/or supplement is also provided. In addition, for example, a method for treating a cancer patient by administering such a pharmaceutical composition is included.

The term "patient" includes a human patient.

An acceptable formulation material is non-toxic to a recipient, in used capacity and concentration. In a specific embodiment, a pharmaceutical composition comprising a therapeutically effective dose of human ROR1 antibody is provided.

Hereinafter, desirable examples are presented to facilitate understanding of the present invention. However, the following examples are provided for a better understanding of the present invention, and the scope of the present invention is not limited by the following examples.

Example 1: Preparation of ROR1 Antibody

Example 1-1: Antigen

An ROR1-ECD-Fc form of protein, in which Fc was linked to a C-terminal of an extracellular domain (ECD) of human ROR1, was used as an antigen.

Specifically, a residue corresponding to the $1^{st}$ amino acid to $406^{th}$ amino acid of the ROR1 amino acid sequence represented by NCBI reference number NP_005003.2 as a protein comprising the extracellular domain of ROR1 was used for preparation of the antigen. The gene encoding the extracellular domain of ROR1 was used by purchasing cDNA of Origene company (Origene, RC214967). In addition, to purify the ROR1 extracellular domain later, a gene encoding Fc protein derived from a human IgG1 was synthesized and linked to the 3' terminal of the gene encoding the ROR1 extracellular domain (hereinafter, named as 'ROR1-Fc'). The gene was introduced to a pcDNA3.1 vector, and a vector encoding an ROR1-Fc nucleic acid in a mammal cell line was secured.

The ROR1-Fc was expressed by temporarily transfecting the expression vector to a HEK 293E cell and culturing it under the condition of 8% $CO_2$, 37° C. in a DMEM-F12 medium, and the medium was collected per 72 hours, and then mediums were combined and the Fc-ROR1 ECD protein was purified by using a protein A affinity chromatography.

Example 1-2: Antibody Sorting Through Phage Library Screening

Preparation of Library Phage

After culturing $2\times10^{10}$ *E. coli* having a human-derived scFv (single-chain variable fragment) library (Yang et. al., 2009 Mol. Cells 27:225) gene having the binding variety to various antigens in a medium comprising 2×YT (Amresco, J902-500G), carbenicillin (Duchefa, C0109.0025) 100 µg/ml, and 2% glucose (sigma, G7021) at 37° C. for 2 hours to 3 hours (OD600=0.5~0.7), a helper phage was infected and then it was cultured in a 2×YT [2×YT, carbenicillin, kanamycin (Duchfa, K0126) 70 µg/ml, 1 mM IPTG (Duchefa, 11401)] medium at 30° C. for 16 hours, and thereby phage packing was induced. Then, after centrifuging the cultured cells (6000 rpm, 15 min, 4° C.), 4% PEG8000 (sigma, P2139) and 3% NaCl (Samchun, S2097) were added to a supernatant and it was melted well, and then it was reacted on ice for 1 hour. After centrifuging (8000 rpm, 20 min, 4° C.) again, PBS (Phosphate buffered saline, Gibco 10010-023) was added to a pellet and it was suspended, and then centrifuged (12000 rpm, 10 min, 4° C.), and the supernatant comprising the library phage was put into a new tube and it was stored at 4° C. before use.

Panning Through Phage Display

To sort antibodies binding to a human ROR1 protein, using the ROR1-Fc protein prepared in Example 1-1, panning was progressed 3 times in total as follows.

Specifically, after adsorbing a protein on a surface of test tube at 4° C. overnight, by adding 10 µg/ml concentration of ROR1-Fc and a negative control group-Fc (BMCA-Fc) in PBS into an immunotube (maxisorp 444202), bovine serum albumin (BSA) 3% solution was added to the test tube and the surface in which the ROR1-Fc was not adsorbed was protected. After emptying the test tube, the antibody phage library of $10^{12}$ CFU dispersed in BSA 3% solution was put into the immunotube in which the control group Fc protein was adsorbed and it was reacted for 1 hour (negative selection). Then, phages which were not bound to the negative control group Fc were recovered and were combined to the immunotube in which the ROR1-Fc was adsorbed. Phages which were bound non-specifically were washed with a PBS-T (Phosphate buffered saline-0.05% Tween 20) solution 5 times~30 times to remove, and the remained antigen-specific phage antibodies were recovered by using 100 mM triethylamine solution. After neutralizing the recovered phages with IM Tris buffer (pH 7.4), they were infected by ER2537 *E. coli* at 37° C. for 1 hour, and the infected *E. coli* was painted out on a 2×YT agar medium and cultured at 37° C. overnight. Next day, the cultured *E. coli* was suspended in a 4 ml of 2×YT carbenicillin culture solution and 15% glycerol was added, and a part was stored at −80° C. and the rest was used for preparing phages for next experiments. By repeating this process 3 rounds in total, an ROR1 antigen-specific phage pool was amplified and concentrated.

Single Clone Screening

To sort monoclonal antibodies specifically binding to ROR1 from the phage pool obtained through the panning, the experiment as follows was performed.

To isolate monoclones from the concentrated pool, after smearing the phage pool on a LB-tetracycline/carbenicillin agar medium and culturing, a single colony was secured. Then, after inoculating monoclones on a 96-deep well plate in which 400 μl of 2×YT-tetracycline/carbenicillin medium was put per well and cultivating overnight, 10 μl culture solution was put on a new 96-deep well plate in which 390 μl of 2×YT-tetracycline/carbenicillin medium was put and it was cultured at 37° C. for 4 hours. 1 mM IPTG was put into the culture solution and it was cultured at 30° C. overnight. The culture solution cultured overnight was centrifuged to take a supernatant.

Then, clones expressing a soluble monoclonal scFv which binds to a human ROR1-Fc antigen were selected by using the ELISA method as follows (Steinberger. Rader and Barbas III. 2000. Phage display vectors. In: Phage Display Laboratory Manual. 1st ed. Cold Spring Harbor Laboratory Press. NY. USA. pp. 11.9-11.12). Specifically, the recombinant human ROR1-Fc or BCMA-Fc prepared in Example 1-1 of 100 ng per well was put on a 96-well microtiter plate (Nunc-Immuno Plates, NUNC, USA) and it was coated at 4° C. overnight. The BCMA-Fc, used as a negative control group, is a recombinant protein in which the extracellular domain region of the human BCMA protein was linked to human Fc. 3% BSA of 200 μL per well was put and blocking was performed at 37° C. for 2 hours. The monoclonal phage supernatant was mixed with 3% BSA at the ratio of 1:1, and this mixed solution was loaded on the well 100 μL each, and then it was reacted at 37° C. for 2 hours. After washing with PBST 300 μL 5 times, the anti-HA HRP binding antibody was put and it was reacted at 37° C. for 1 hour, and then it was washed with PBST 5 times. After color development by putting TMB (Tetramethylbenzidine, Sigma, T0440) 100 μL, 1N $H_2SO_4$ 50 μL was put and the reaction was stopped, and then the absorbances at 450 nm and 650 nm were measured, and clones of having absorbance value (450 nm-650 nm) of 1.0 or more when coated with ROR1 1 μg/mL were selected (FIG. 1).

Figure 2:
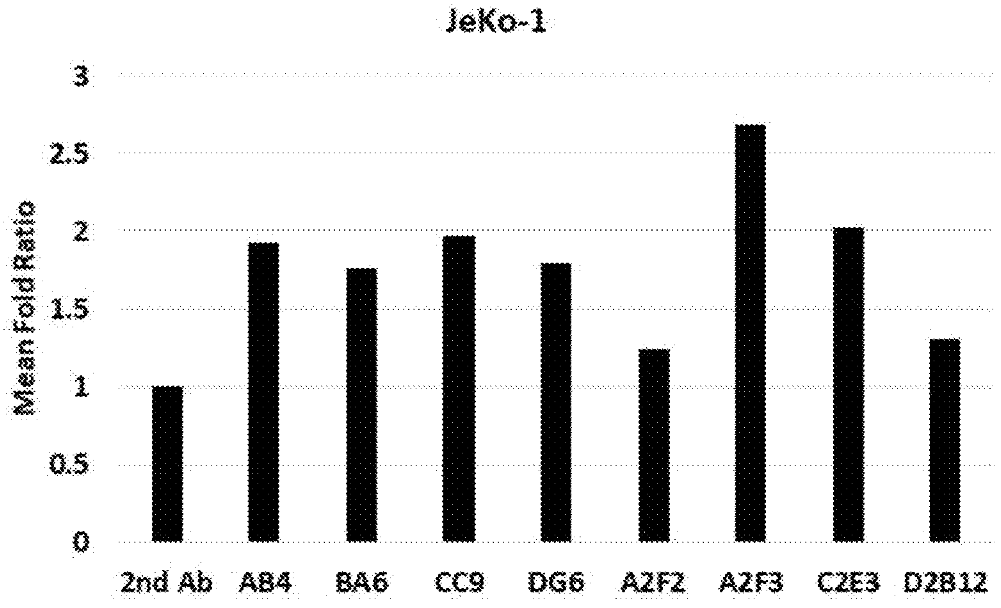
FIG. 2 is the result of measurement (FACS) of the binding capacity to the ROR1 antigen of the anti-ROR1 monoclonal phage antibody prepared according to one embodiment of the present invention, and JeKo-1 cell line was used as a cell expressing ROR1 on a cell surface. It shows that each anti-ROR1 monoclonal antibody specifically binds to the ROR1 expressed on the cell surface.
Figure 3A:
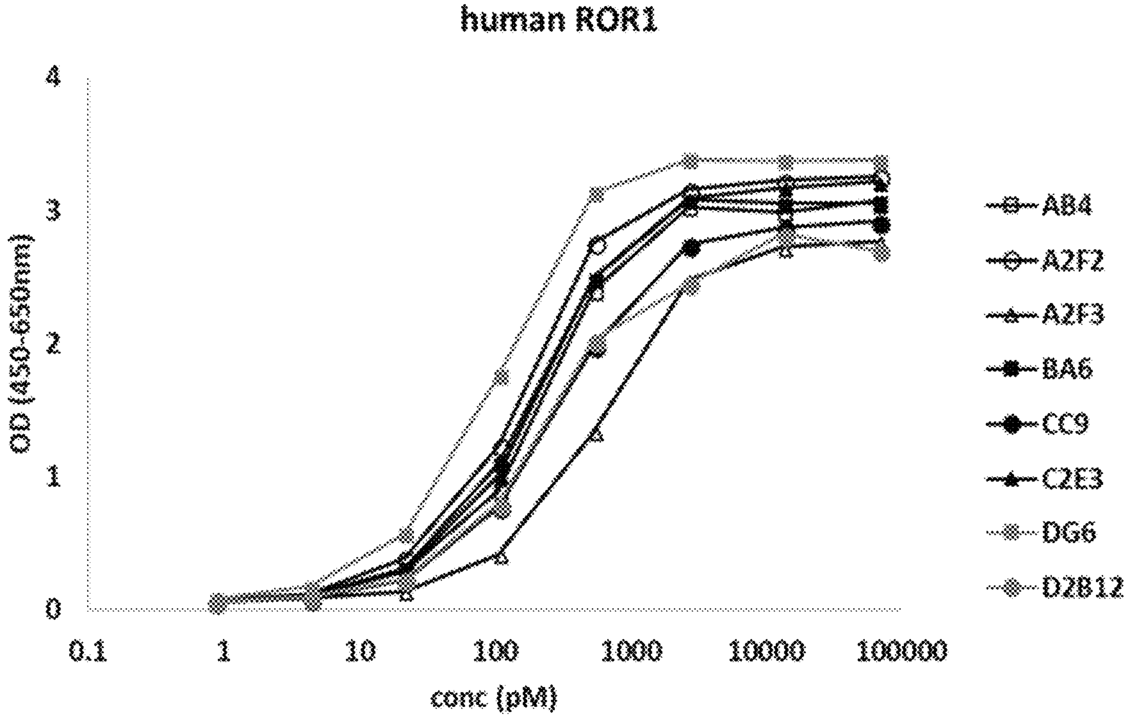
FIGS. 3*a* and 3*b* are the results of analysis (ELISA) of the binding capacity to the human ROR1 antigen of the anti-ROR1 IgG antibody prepared according to one embodiment of the present invention. It shows that each antibody binds to the human ROR1 antigen concentration-dependently. The result shows that the binding capacity to ROR1 is maintained, even after modifying the monoclonal phage antibody to an IgG form.
Figure 3B:
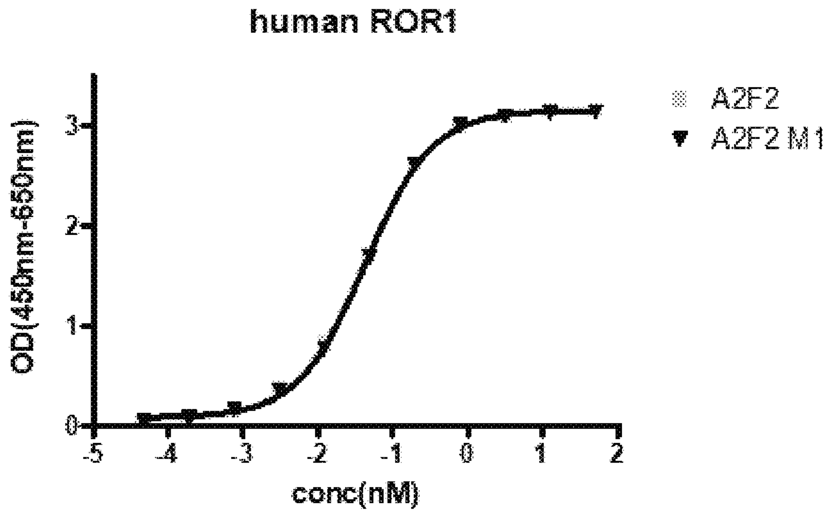
Figure 3B:
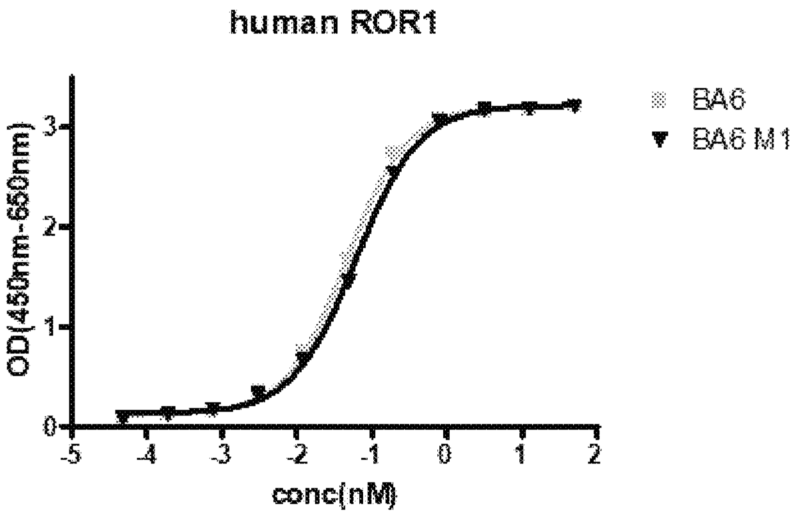

Then, clones binding to a cell line expressing ROR1 were screened by flow cytometry. Specifically, the monoclonal scFv supernatant 100 μl was reacted with a cancer cell line overexpressing ROR1 (JeKo-1), and then it was washed with PBS twice. After reacting with the anti-HA-FITC antibody (Sigma, H7411) at 4° C. for 30 min and washing with PBS twice, it was suspended with PBS 200 μl, and clones binding to Jeko-1 cell line were sorted by using FACSCalibur flow cytometer (FIG. 2).

From them, 10 antibody clones binding to the recombinant human ROR1 protein and ROR1 expressing cell line (AB4, A2F2, A2F3, BA6, CC9, C2E3, DG6 D2B12, A2F2 M1, and BA6 M1) were sorted, and the amino acid sequence of heavy chain variable and light chain variable regions and CDR sequence of each antibody are as the following tables.

TABLE 4

| | CDR Sequences of Heavy Chain Variable (VH) | | | | | | |
|---|---|---|---|---|---|---|---|
| | CDR1 | | CDR2 | | CDR3 | | VH |
| Clone | Sequence | SEQ ID NO | Sequence | SEQ ID NO | Sequence | SEQ ID NO | SEQ ID NO |
| AB4 | SYDMS | 1 | WISPDSGSIYYADS VKG | 6 | PTGRFDY | 14 | 43 |
| A2F2 | DYYMS | 2 | SISPDGSNTYYADS VKG | 7 | NLRAFDY | 15 | 44 |
| A2F3 | SYDMS | 1 | WISPGGGSKYYAD SVKG | 8 | VNGRFDY | 16 | 45 |
| BA6 | NYDMS | 3 | AIYHSGSSKYYAD SVKG | 9 | GGNGAWDTGFDY | 17 | 46 |
| CC9 | SYDMS | 1 | GISHGSGNKYYAD SVKG | 10 | RLSLRRRPSYYSD NAMDV | 18 | 47 |
| C2E3 | NYAMS | 4 | SISHNSGSTYYADS VKG | 11 | FISARKSLGRSYSN GMDV | 19 | 48 |
| DG6 | DYDMS | 5 | VISPDGGSIYYADS VKG | 12 | DVVECNMNPCSY DNAMDV | 20 | 49 |
| D2B12 | NYDMS | 3 | SISPSSGSSIYYADS VKG | 13 | APGWCQAPSCYY DNAMDV | 21 | 50 |
| A2F2 M1 | DYYMS | 2 | SISPDASNTYYADS VKG | 96 | NLRAFDY | 15 | 98 |
| BA6 M1 | NYDMS | 3 | AIYHSGSSKYYAD SVKG | 9 | GGNAAWDTGFDY | 97 | 99 |

TABLE 5

| CDR Sequences of Light Chain Variable (VL) | | | | | | | |
|---|---|---|---|---|---|---|---|
| | CDR1 | | CDR2 | | CDR3 | | VL |
| Clone | Sequence | SEQ ID NO | Sequence | SEQ ID NO | Sequence | SEQ ID NO | SEQ ID NO |
| AB4 | SGSSSNIGNNNVN | 22 | YDNKRPS | 30 | GTWDASLSGYV | 38 | 51 |
| A2F2 | SGSSSNIGSNTVY | 23 | ANSQRPS | 31 | GSWDYSLSGYV | 39 | 52 |
| A2F3 | SGSSSNIGNNNVS | 24 | ADSHRPS | 32 | ATWDYSLSGYV | 40 | 53 |
| BA6 | SGSSSNIGSNDVS | 25 | YDNNRPS | 33 | GAWDDSLSGYV | 41 | 54 |
| CC9 | TGSSSNIGNNAVN | 26 | YDSNRPS | 34 | GAWDDSLSGYV | 41 | 55 |
| C2E3 | TGSSSNIGSNDVT | 27 | ADSKRPS | 35 | GTWDYSLSGYV | 42 | 56 |
| DG6 | SGSSSNIGSNYVS | 28 | DDSHRPS | 36 | GAWDDSLSGYV | 41 | 57 |
| D2B12 | SGSSSNIGNNDVS | 29 | DDSQRPS | 37 | GAWDDSLSGYV | 41 | 58 |
| A2F2 M1 | SGSSSNIGSNTVY | 23 | ANSQRPS | 31 | GSWDYSLSGYV | 39 | 52 |
| BA6 M1 | SGSSSNIGSNDVS | 25 | YDNNRPS | 33 | GAWDDSLSGYV | 41 | 54 |

The nucleic acid sequences encoding the variable regions and CDR sequences are comprised as part of nucleic acid sequences encoding the following heavy chain and light chain full-lengths in order of AB4, A2F2, A2F3, BA6, CC9, C2E3, DG6, D2B12, A2F2 M1, and BA6 M1: SEQ ID NO: 75 (heavy chain) and 83 (light chain); SEQ ID NO: 76 (heavy chain) and 84 (light chain); SEQ ID NO: 77 (heavy chain) and 85 (light chain); SEQ ID NO: 78 (heavy chain) and 86 (light chain); SEQ ID NO: 79 (heavy chain) and 87 (light chain); SEQ ID NO: 80 (heavy chain) and 88 (light chain); SEQ ID NO: 81 (heavy chain) and 89 (light chain); SEQ ID NO: 82 (heavy chain) and 90 (light chain); SEQ ID NO: 102 (heavy chain) and 84 (light chain); and SEQ ID NO: 103 (heavy chain) and 86 (light chain), respectively. The nucleic acid sequences encoding constant regions in the nucleic acid sequence are SEQ ID NO: 92 (heavy chain), SEQ ID NO: 94 (light chain) and 95 (light chain).

Example 2: Conversion of Anti-ROR1 scFv into Total IgG Form and Production Thereof

Example 2-1: Cloning of Anti-ROR1 scFv into Full IgG Form

To convert the sequence of each ROR1-specific monoclonal phage antibody, secured in Example 1, into a full IgG form, a nucleic acid encoding heavy chain and light chain variable regions of each clone secured in Example 1 was synthesized (Genotech, Korea). A gene encoding a human IgG1 subtype of heavy chain and light chain constant regions (SEQ ID NO: 91 and 93, respectively) protein was synthesized and was linked to the nucleic acid encoding each heavy chain and light chain variable region. each of the nucleic acid encoding light chain and heavy chain of each antibody was cloned into a pcDNA3.1-based expression vector, and a vector encoding the nucleic acid for the antibody in a CHO-S mammal cell line was secured.

A chimera antibody in which a human IgG1 was linked to the variable region of 2A2 (U.S. Pat. No. 9,316,646) that was the conventional anti-ROR1 antibody was used as a comparison group antibody.

The IgG form of antibodies were disclosed as the following heavy chain and light chain full-lengths in order of AB4, A2F2, A2F3, BA6, CC9, C2E3, DG6, and D2B12, A2F2 M1, and BA6 M1: SEQ ID NO: 59 (heavy chain) and 67 (light chain); SEQ ID NO: 60 (heavy chain) and 68 (light chain); SEQ ID NO: 61 (heavy chain) and 69 (light chain); SEQ ID NO: 62 (heavy chain) and 70 (light chain); SEQ ID NO: 63 (heavy chain) and 71 (light chain); SEQ ID NO: 64 (heavy chain) and 72 (light chain); SEQ ID NO: 65 (heavy chain) and 73 (light chain); SEQ ID NO: 66 (heavy chain) and 74 (light chain); SEQ ID NO: 100 (heavy chain) and 68 (light chain); and SEQ ID NO: 101 (heavy chain) and 70 (light chain), respectively.

Example 2-2: Expression of Anti-ROR1 IgG Antibody

CHO-S cells were cultured at 8% $CO_2$, 37° C. for 1 day in a CD-CHO (Gibco, 10743) medium at a concentration of $1.5\times10^6$ cells/ml. After preparing cells grown as $2.5\sim3\times10^6$ cells/ml at a concentration of $2.1\times10^6$ cells/ml using the CD-CHO medium comprising 1% DMSO on the day of DNA transfection, they were cultured at 8% $CO_2$, 37° C. for 3 hours. After centrifuging at 3000 rpm for 15 min and having the supernatant removed, it was resuspended in a RPMI 1640 medium comprising 2.5% FBS. Then, each vector expressing a heavy chain and a light chain as obtained from Example 2-1 was diluted in Opti-MEM medium, in 1 μg per medium ml, and 8 μg per culture medium ml of PEI (Polysciences, 23966, stock concentration: 1 mg/ml) was diluted. After the vector and PEI mixture were mixed and stood at a room temperature for 10 min, it was put into a flask comprising the cell prepared as above, and then it was cultured at 5% $CO_2$, 37° C., 100 rpm for 4 hours, and the same volume of CD-CHO medium as the culturing volume was put, and then it was cultured at 8% $CO_2$, 37° C., 110 rpm for 4 days.

Example 2-3: Separate Purification of Anti-ROR1 IgG Antibody

After passing an equilibrium buffer solution (50 mM Tris-HCl, pH7.5, 100 mM NaCl) through into Mab selectsure (GE healthcare, 5 mL) and thereby equilibrating, the culture solution of Example 3-2 was passed through into a column (Mab selectsure (GE healthcare, 5 mL)) in order to allow the expressed antibody to bind to the column. Then, after eluting it with 50 mM Na-citrate (pH 3.4), 100 mM NaCl solution, it was neutralized by using 1M Tris-HCl (pH 9.0) so that the final pH was 7.2. The buffer solution was exchanged to PBS (phosphate buffered saline, pH 7.4).

Example 3: Analysis of Binding Specificity to ROR1 of Anti-ROR1 IgG Antibody

Example 3-1: Analysis of Binding Capacity to ROR1 Antigen (Extracellular Domain) of Anti-ROR1 IgG Antibody (ELISA)

The specific binding capacity to the antigen of IgG antibody of each clone selected and prepared in Examples 1 and 2 was analyzed as follows.

The anti-ROR1 antibody-antigen binding affinity was estimated by using an ELISA-based solution binding test. Specifically, a 96-well microtiter plate (Nunc-Immuno Plates, NUNC) was coated with the ROR1 protein at a concentration of 1 μg/ml in a PBS solution as described below at 4° C. for 16 hours, and non-specific binding sites were blocked with 3% BSA (bovine serum albumin) for 2 hours. For this, as the ROR1 protein, in case of human ROR1, ROR1-Fc of Example 1 or recombinant ROR1-His (Sino Biological, 13968-H08H) was used. The ROR1-His used for ELISA was a protein of sino biological company (13968-H08H) as described in the above sentence, and ROR1-His of Example 1 or recombinant mouse ROR1 protein was used (Acrobiosystems, RO1-M5221-100 μg).

Then, after adding the anti-ROR1 antibody prepared in Example 3 at the concentration described in FIG. 2 into the microtiter plate on a 96-well microtiter plate, the binding capacity was analyzed with ELISA as follows. Specifically, after constant temperature treatment for 2 hours, the plate was washed with PBS comprising 0.05% tween 20 5 times, and then a HRP-conjugated Fab multiclonal antibody reagent (Pierce, 31414) was diluted at 1:10,000 ratio, and was put into the washed microtiter plate, and it was incubated at 37° C. for 1 hour, and the ROR1 antibody bound to the plate was detected. After reaction, it was color-developed by using TMB (Tetramethylbenzidine, Sigma, T0440). The enzymatic reaction was stopped by 0.5 mol/L of sulfuric acid, and the absorbances at 450 nm and 650 nm were measured by using a micro plate reader device (molecular device) (450 nm-650 nm).

Figure 4:
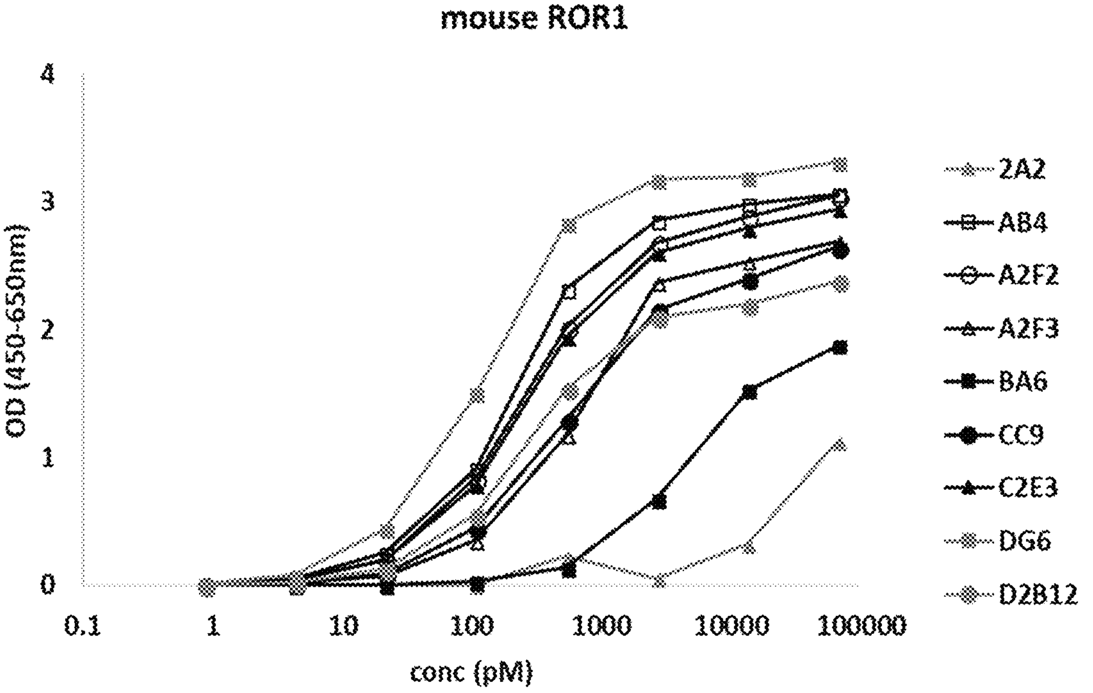
FIG. 4 is the result of analysis (ELISA) of the binding capacity to the mouse ROR1 antigen of the anti-ROR1 IgG antibody prepared according to one embodiment of the present invention. It shows that each antibody binds to mouse ROR1 antigen concentration-dependently. Through the present experiment, it was confirmed that the anti-ROR1 antibody of the present invention had cross-reactivity to mouse ROR1. It was shown that the 2A2 antibody used as a comparison group had cross-reactivity to the mouse ROR1, but the degree of binding was relatively weak compared to the anti-ROR1 antibody of the present invention.

The result was disclosed in FIGS. **3*a* and 3*b*, and FIG. 4**, and it was confirmed that the anti-ROR1 antibody of the present invention bind to the human ROR1 and mouse ROR1 in a concentration dependent manner. In addition, when comparing the cross-reactivity to the mouse ROR1 protein, it was shown that the ROR1 antibody of the present invention had excellent binding capacity as compared to 2A2 comparison antibody used as the comparison group.

Example 3-2: Measurement of Specific Binding Capacity to Cell Surface-Expressed ROR1 Antigen of Anti-ROR1 IgG Antibody (FACS)

Binding to a cell surface-expressed antigen is a necessary requisite for an antibody against a specific antigen to be used in a living body as an antibody for treatment, etc. In case of some antibodies, they bind to purified antigens but do not bind to a cell surface-expressed antigen. In such case, binding to an antigen doesn't occur when the antibody is administered to a living body, the antibody cannot bind to a cell expressing the antigen, and therefore, it cannot show the activity in a living body such as an antibody for treatment.

Accordingly, whether the anti-ROR1 antibody of the present invention binds to a cell surface-expressed ROR1 was confirmed by FACS analysis.

Figure 5:
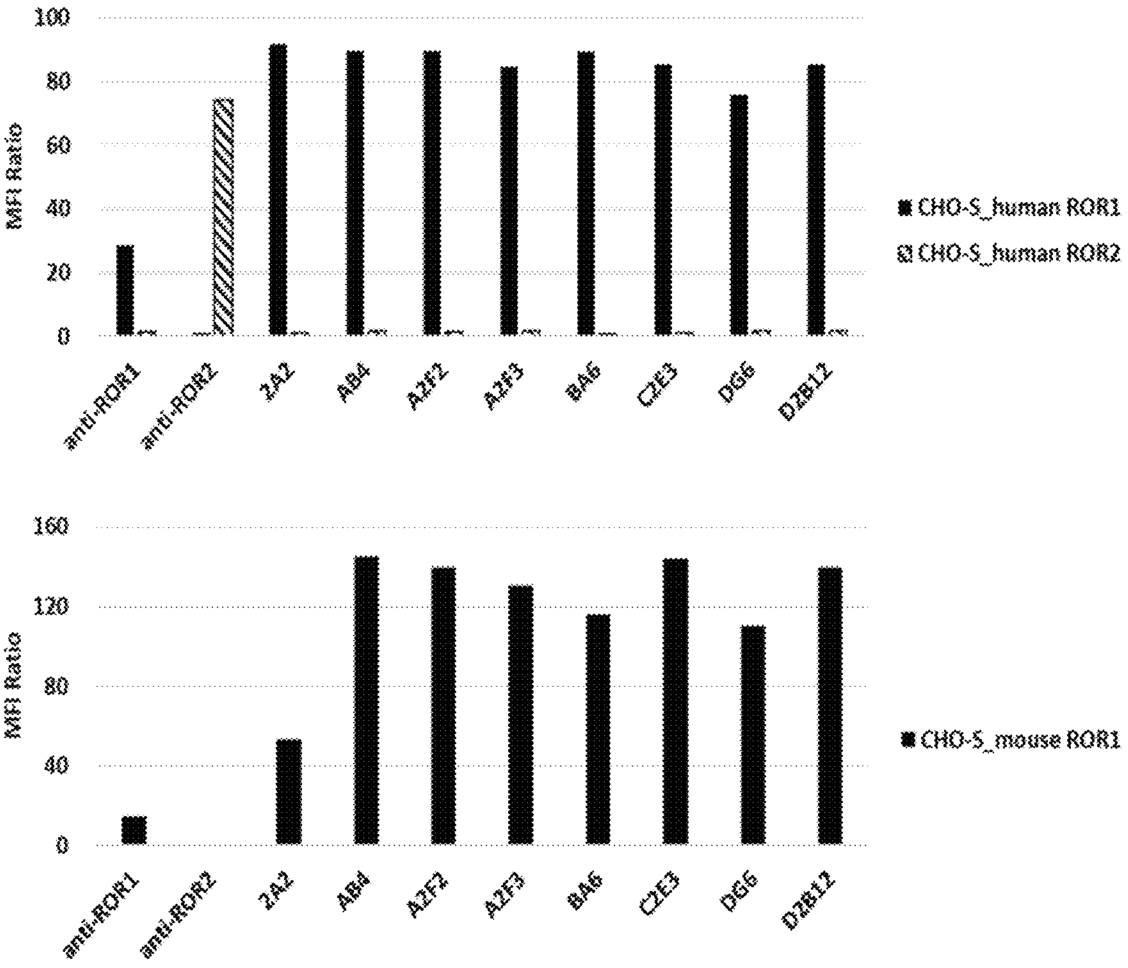
FIG. 5 is the result of measurement (FACS) of the binding capacity to the ROR1 antigen expressed on the cell surface of the anti-ROR1 antibody prepared according to one embodiment of the present invention, and the CHO-human ROR1 cell line, the CHO-human ROR2 and the CHO-mouse ROR1 are cell lines artificially overexpressing human ROR1, human ROR2 and mouse ROR1, respectively. It was shown that each antibody specifically bound to human ROR1 expressed on the cell surface and did not bind to human ROR2 that was a family protein. In addition, it was confirmed that the anti-ROR1 antibody of the present invention had intraspecific cross-reactivity to the mouse ROR1, by confirming that it bound to a cell line artificially overexpressing the mouse ROR1. It was shown that the 2A2 antibody used as a comparison group had cross-reactivity to the mouse ROR1, but the degree of binding was relatively weak compared to the anti-ROR1 antibody of the present invention.
Figure 6:
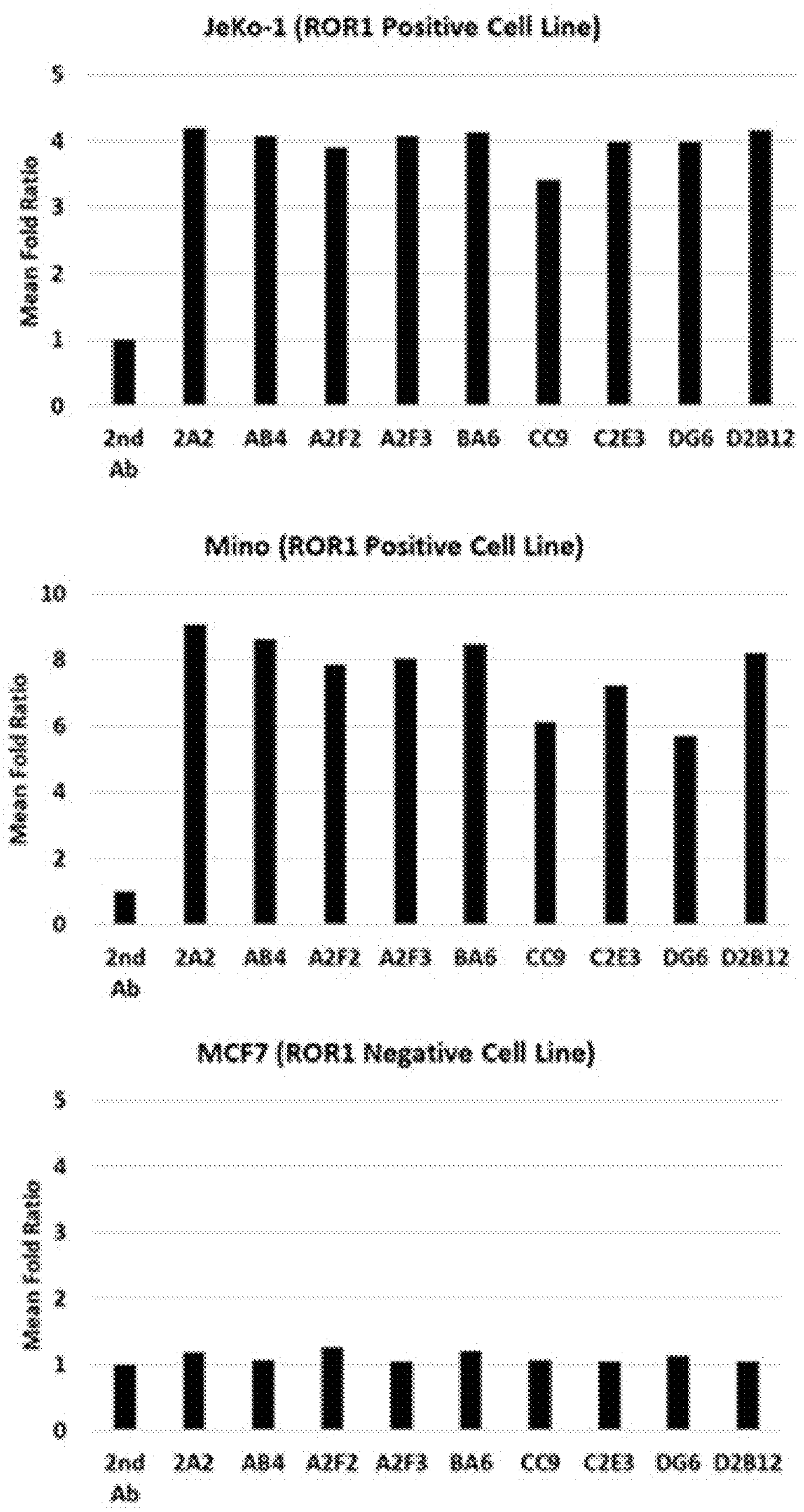
FIG. 6 is the result of measurement (FACS) of the binding capacity to the ROR1 antigen expressed on the cell surface of the anti-ROR1 antibody prepared according to one embodiment of the present invention, and JeKo-1 and Mino cell line, and MCF7 cell line were used as an ROR1 expression positive cell line and an ROR1 negative cell line, respectively. It was shown that each antibody specifically bound to ROR1 expressed on the cell surface and did not bind in the MCF7 that is a cell line which does not express ROR1.

For this experiment, the degree of binding of the anti-ROR1 antibody and ROR1 was measured by using FACSCalibur (BD Biosciences) device with the cell lines as follows, the cell lines artificially overexpressing the ROR1 protein by transfecting an ROR1 gene temporarily (CHO-human ROR1, CHO-human ROR2, CHO-mouse ROR1) or stably (MC38-human ROR1) (FIG. 5 and FIG. 7, respectively) or the cell lines expressing ROR1 (JeKo-1, Mino) (FIG. 6) or a cell line not expressing ROR1 (MCF7) (FIG. 6). MCF7 is a negative control group which does not express ROR1, and CHO-human ROR2 is a negative control group expressing human ROR2. JeKo-1, Mino, CHO-human ROR1, CHO-mouse ROR1 and MC38-human ROR1 are all cell lines expressing human ROR1 or mouse ROR1.

Specifically, after disassociating each cell line and washing in PBS, the number of cells was counted and set as $2\times10^5$ cells/200 μl PBS, and then each ROR1 monoclonal antibody in Example 3 was prepared in 10 μg/mL or as 5 fold-diluted from 10 μg/mL, and was reacted at 4° C. for 1 hour. After reaction, cells were washed in PBS and then the FITC-labeled constant region (Fc)-specific antibody (Goat anti-human IgG FITC conjugate, Fc specific, Sigma, F9512, concentration: 2.0 mg/ml) was suspended in 2 μl/1×105 cells/200 μl PBS, and it was reacted at 4° C. for 1 hours. The confirmation of expression degree of human ROR1, human ROR2 and mouse ROR1 that were temporarily overexpressed was analyzed by using a commercially available antibody for FACS analysis (anti-ROR1: R&D Systems, FAB2000G, anti-ROR2: R&D, FAB20641P). After reaction, cells were washed in PBS and decoded by using a FACSCalibur device. The negative control group (2nd Ab) was treated only with the FITC-labeled constant region (Fc)-specific antibody. The result for the peak shift in the experimental group treated with each ROR1 monoclonal antibody was compared to the result for the shift in the control group (Mean Fluorescence Intensity Ratio, MFI Ratio: MFI of anti-ROR1/MFI of 2nd Ab).

Figure 7:
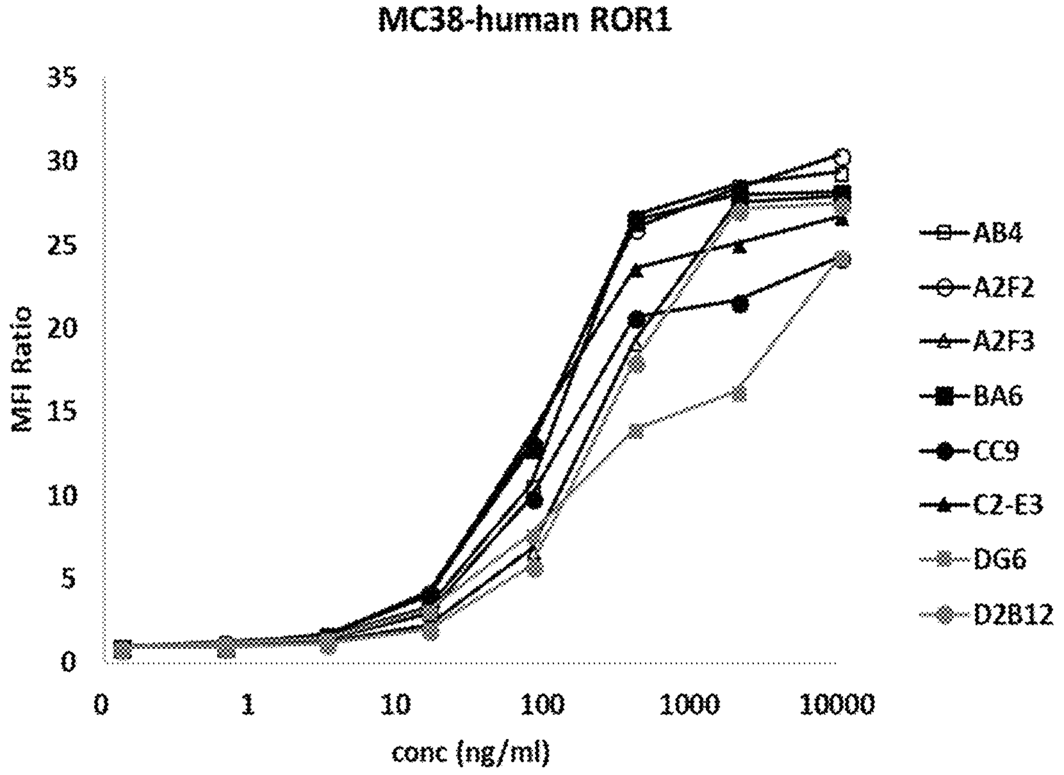
FIG. 7 is the result of measurement (FACS) of the binding capacity to the ROR1 antigen expressed on the cell surface of the anti-ROR1 antibody prepared according to one embodiment of the present invention. MC38 human ROR1 cell line in which human ROR1 was artificially overexpressed in MC38 that is a mouse colorectal cancer cell line was used. It was shown that each antibody bound to a cell line overexpressing human ROR1 concentration-dependently.

The result was disclosed in FIG. 5, FIG. 6 and FIG. 7. As a result, it was confirmed that the anti-ROR1 antibody of the present invention specifically binds to the extracellular domain of human ROR1 as originally expressed in cells (FIG. 6) and human ROR1 as artificially overexpressed in cells (FIG. 5, FIG. 7), in a concentration-dependent pattern. In addition, it was confirmed that it does not bind to a family protein, human ROR2, and it has cross-reactivity to mouse ROR1 (FIG. 5). Comparing the cross-reactivity to mouse ROR1 expressed on a cell surface, it was confirmed that the degree of binding of the ROR1 antibody of the present invention was more excellent as compared to the antibody used as the comparison group, 2A2 (FIG. 5).

Example 3-3: Measurement of Binding Capacity to Cell Surface-Expressed ROR1 Antigen of Anti-ROR1 IgG Antibody in Various Cancer Forms Subsequently, whether the anti-ROR1 antibody of the present invention binds to a cell surface-expressed ROR1 in various kinds of cancer cell lines was confirmed through FACS analysis. ROR1 is expressed in various cancer cells, and it has been reported that it is overexpressed in various solid cancers such as breast cancer, renal cancer, ovarian cancer, gastric cancer, liver cancer, lung cancer, colorectal cancer, pancreatic cancer, skin cancer, bladder cancer, testicular cancer, uterine cancer, prostate cancer, non-small cell lung cancer (NSCLC), neuroblastoma, brain cancer, colon cancer, squamous cell carcinoma, melanoma, myeloma, cervical cancer, thyroid cancer, head and neck cancer and adrenal cancer, etc. as well as hematologic malignancy such as chronic lymphocytic leukemia (CLL), B-cell leukemia, lymphoma, acute myeloid leukemia (AML), Burkitt lymphoma, mantle cell lymphoma (MCL), acute lymphoblastic leukemia (ALL), Diffuse large B-cell lymphoma (DLBCL), follicular lymphoma (FL) and marginal zone lymphoma (MZL), etc.

For this experiment, various kinds of cancer cell lines were used as follows: AGS (ATCC® CRL-1739™, human gastric adenocarcinoma), NCI-N87 (ATCC® CRL-5822™, human gastric carcinoma), MKN-28 (KCLB 80102, human gastic adenocarcinoma), SNU-1750 (KCLB 01750, human gastric adenocarcinoma), SNU-16 (ATCC® CRL-5974™, human gastric carcinoma), HCC1187 (ATCC® CRL-2322™, human breast cancer TNM stage IIA grade 3), MDA-MB-231 ATCC® HTB-26™, human breast cancer), MDA-MB-468 (ATCC® HTB-132™, human breast cancer), HCC70 (ATCC® CRL2315™, human breast cancer TNM stage IIIA, grade 3), HCC1143 (ATCC® CRL-2321™, TNM stage IIA, grade3, primary ductal carcinoma), BT20 (ATCC® HTB-19™ human breast cancer), HCC1806 (ATCC® CRL-2335™, human breast cancer TNM stage IIB grade 2), HCC1937 (ATCC® CRL2336™, TNM stage IIB, grade 3, primary ductal carcinoma), BT474 (ATCC® HTB-20™, ductal carcinoma), MCF7 (ATCC® HTB-22™, breast cancer metastatic site), H460 (ATCC® HTB-177™, large cell lung cancer), A549 (ATCC® CCL-185™, lung carcinoma), NCI-H1975 (ATCC® CRL-5908™, non-small cell lung H1437 cancer), (ATCC® CRL5872™, stage 1, adenocarcinoma non small cell lung cancer), Calu-6 (ATCC® HTB-56™, anaplastic lung carcinoma), HCT116 (ATCC® CCL-247™, colorectal carcinoma), DLD-1 (ATCC® CCL-221™, Dukes'type C, colorectal adenocarcinoma), HT29 (ATCC® HTB-38™, colorectal adenocarcinoma), 697 (DSMZ ACC 42, acute myeloblastic leukemia), Kasumi-2 (ATCC® CRL-2724™, acute myeloblastic leukemia), Mino (ATCC® CRL-3000™, MantleCellLymphoma), JeKo-1 (ATCC® CRL3006™, MantleCellLymphoma), Jurkat (ATCC® TIB-152™, acute T cell leukemia). For the cell lines, the binding to ROR1 was analyzed with FACS (FACSCalibur, BD Biosciences) by using the anti-ROR1 antibody of the present invention.

Specifically, after disassociating each cell line and washing in PBS, the number of cells was counted and set as $2\times10^5$ cells/200 µl PBS, and then the clone C2E3 among ROR1 monoclonal antibodies prepared in Example 3 was treated in 10 µg/mL, and it was reacted at 4° C. for 1 hour. After reaction, cells were washed in PBS, and then the FITC-labeled constant region (Fc)-specific antibody (Goat anti-human IgG FITC conjugate, Fc specific, Sigma, F9512, concentration: 2.0 mg/ml) was suspended in 2 µl/$1\times10^5$ cells/200 µl PBS, and it was reacted at 4° C. for 1 hour. After reaction, cells were washed in PBS, it was analyzed using a FACSCalibur device. The negative control group was treated only with the FITC-labeled constant region (Fc)-specific antibody. To compare the expression degrees of ROR1 among the cancer cell lines, the value of the result for the peak shift in the experimental group treated with the ROR1 monoclonal antibody (C2E3) of the present invention was divided by the result for the peak shift in the control group (Mean Fluorescence Intensity Ratio MFI Ratio: MFI of anti-ROR1/MFI of 2nd Ab).

The result was described in FIG. 8. As a result, it was confirmed that the anti-ROR1 antibody of the present invention binds to ROR1 expressed in various cancer cell lines derived from gastric cancer, breast cancer, lung cancer, colorectal cancer, acute lymphoblastic leukemia (ALL) and mantle cell lymphoma (MCL).

Example 4: Measurement of Affinity to ROR1 of Anti-ROR1 IgG Antibody

A 96 well black microplate (greiner bio one) in a biosensor tray case was installed, and 200 µl of 10×KB or D.W was put in 8 wells each. 8 sensors, Anti Penta His biosensors or AR2G biosensors (ForteBio, USA), were placed for 10 min for hydration. 600 µl of Analytic samples were diluted 2 folds or 3 folds to desired concentrations. It was diluted using 1×KB or 10×KB to reach a concentration of 30~0.021 nM. For antigen fixation, 1 µg/mL of a recombinant ROR1-His (Sino Biological, 13968-H08H) was diluted with 10×KB or Sodium Acetate pH5 buffer. For fixation, threshold was set to be 0.3 nmat the loading step. The experiment was performed for 3 min~10 min of association and for 20 min of dissociation. The prepared buffer was put into a new 96 well black microplate in accordance with octet program template in order. 10×KB or D.W 200 µl used as Baseline1 was put. 200 µl of the antigen ROR1-His protein (1 µg/mL) was loaded. 10×KB or D.W 200 µl used as Baseline2 was put. 200 µl of 10×KB buffer or 1×KB corresponding the diluted antibody in 30~0.021 nM, Reference blank was put into each well. The temperature of the experimental plate was fixed at 30° C. After placing all samples, the device was activated. After the experiment was finished, the result was uploaded on Octet Analysis 9.0 software, and then KD value was calculated using 1:1 fitting, and the result was described in the following Table 6. By the KD values from Octet analysis method, it was confirmed that the anti-ROR1 antibody had strong binding capacity to the ROR1 antigen.

TABLE 6

Measurement of affinity to ROR1 of anti-ROR1 IgG antibody

| NO | Clone | KD (M) | kon(1/Msec) | koff(1/sec) | Chi | R^2 |
|---|---|---|---|---|---|---|
| 1 | AB4 | 6.39E−11 | 1.81E+06 | 1.16E−04 | 0.016 | 0.996 |
| 2 | A2F2 | 7.73E−11 | 1.53E+06 | 1.19E−04 | 0.106 | 0.997 |
| 3 | A2F3 | 2.40E−11 | 1.38E+06 | 3.31E−05 | 0.131 | 0.992 |
| 4 | BA6 | 9.37E−11 | 2.47E+06 | 2.31E−04 | 0.138 | 0.993 |
| 5 | C2E3 | 4.24E−10 | 5.46E+06 | 2.31E−03 | 0.176 | 0.966 |
| 6 | CC9 | 7.54E−10 | 7.31E+05 | 5.51E−04 | 0.200 | 0.992 |
| 7 | DG6 | 1.52E−10 | 2.23E+06 | 3.38E−04 | 0.506 | 0.964 |
| 8 | D2B12 | 8.03E−10 | 4.50E+05 | 3.61E−04 | 0.341 | 0.952 |

Example 5: Analysis of Efficacy of Inhibiting Growth of Cancer of Anti-ROR1 IgG Antibody in Mouse Tumor Xenograft Model JeKo-1 cell line, a human mantle cell lymphoma which expresses ROR-1, of $1\times10^7$ cells/head was grafted into the severe combined immunodeficiency mouse (SCID), in order to construct a human cancer graft tumor mouse. After the graft, when the size of tumor reached the average 170 $mm^3$ (Day 1), group separation was conducted, and the 5 kinds of anti-ROR-1 antibodies were administered at 10 mg/kg twice a week, 5 times in total, by using a 1 ml syringe into a mouse intraperitoneally (Day 1, 4, 7, 10 and 14). For the negative control group, a human IgG1 having the similar structure to the anti-ROR-1 antibody (InVivoPlus human IgG1 isotype control, BioXCell, BP0297) was administered at 10 mg/kg twice a week, 5 times in total, intraperitoneally. The size and weight of tumor grafted into the mouse were measured just before the initial administration (Day 1), then measured just before the administration on each administration day, and measured 2 days after the final administration (Day 16).

Figure 9A:
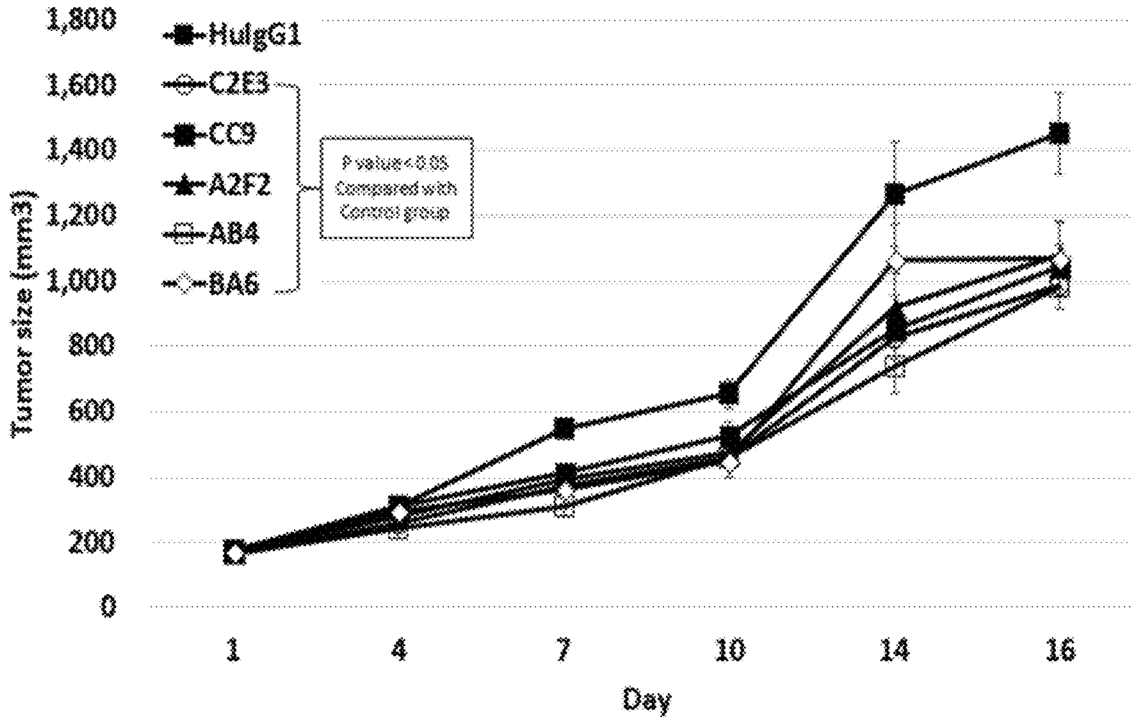
FIG. 9 is the result of analyzing a cancer-inhibiting efficacy of the anti-ROR1 antibody in a mouse tumor xenograft model. It was shown that each anti-ROR1 antibody effectively inhibited the growth of cancer in a severe combined immune deficiency mouse (SCID mouse) in which a mantle cell lymphoma cell line, Jeko-1 cell line was grafted. It was shown that administered all the 5 kinds of anti-ROR1 antibodies of the present invention inhibited the growth of cancer at a statistically significant level, and the degree of cancer inhibition of each antibody clone was shown as similar. As the result of measuring weights, the weight increase pattern was observed as similar in the group administering the anti-ROR1 antibody as compared to the negative control group, human IgG1 antibody (HuIgG1). This result means that the ROR1 antibody of the present invention effectively binds to a cancer cell overexpressing ROR1, thereby inhibiting the growth of cancer, and being usefully used as a cancer therapeutic agent.
Figure 9B:
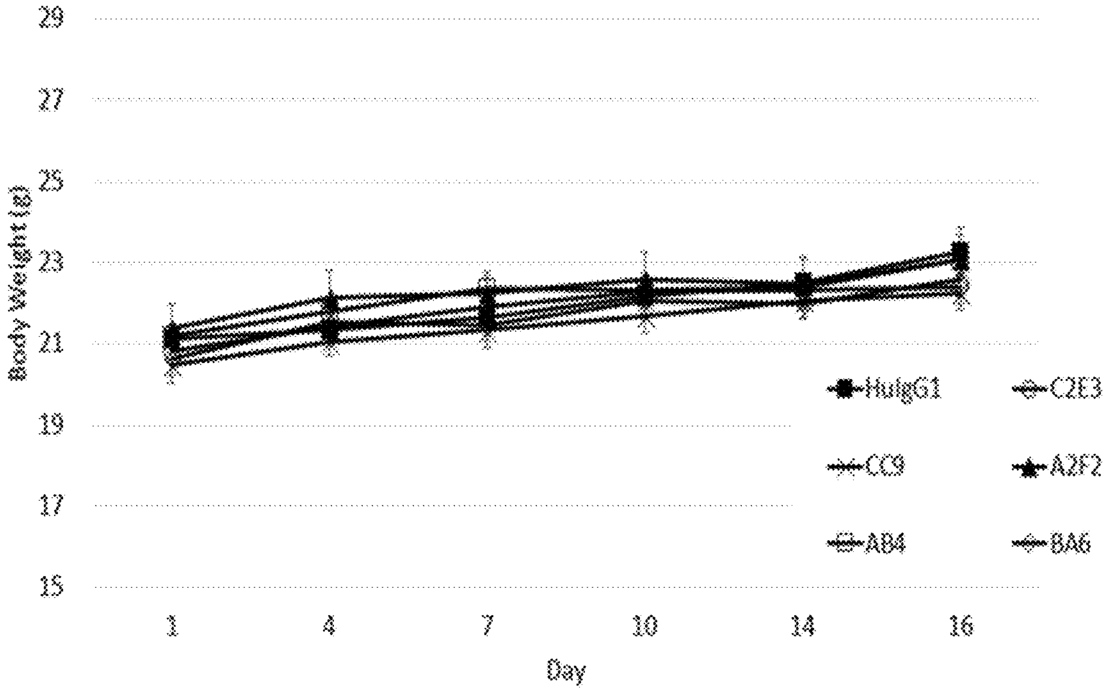

The result was described in FIG. 9*a* and FIG. 9*b*. It was shown that the anti-ROR-1 antibody inhibited the growth of cancer. The effect of growth inhibition of cancer (% Tumor Growth Inhibition, % TGI) compared to the negative control group, human IgG1 antibody (HuIgG1) was C2E3 36.0%, A2F2 28.9%, AB4 36.1%, BA6 31.7% and CC9 29.4%, on the experiment termination date (Day 16). It was shown that the anti-ROR1 antibody had a statistically significant difference compared to the HuIgG administration group (one-way layout analysis of variance, P value<0.05) (FIG. 9*a*). The measurement of weight showed no significant differences among administration groups (FIG. 9*b*). As described in Examples 3-1 and 3-2, the anti-ROR1 antibody of the present invention had the cross-reactivity to the mouse ROR1 antigen. Therefore, the administered anti-ROR1 antibody of the present invention can bind to the mouse ROR1 which the mouse expresses by itself in addition to the human ROR1 which the xenografted human mantle cell lymphoma, JeKo-1 cell line expresses. The patterns in which weight increase between the negative control group (HuIgG1) and the anti-ROR1 antibody of the present invention were similar each other. This means that the toxicity was not induced by the anti-ROR1 antibody of the present invention. The result shows that the antibody can be usefully used as a cancer therapeutic agent.

It was shown that all the 5 kinds of ROR1 antibodies of the present invention inhibited the growth of cancer in the mouse tumor xenograft model. It was shown that some antibodies (C2E3, AB4) could induce apoptosis of the ROR1 overexpressing cancer call line, through multimerization by the anti-human Fc antibody, as described in the following Example 6 and FIG. 10. Since the inhibition mechanism of cancer can be possible through various mechanisms such as apoptosis induction, cancer cell division and growth inhibition, cancer angiogenesis inhibition, immunocyte activation, etc., the result of FIG. 10 described later means that the anti-ROR1 antibodies can inhibit the growth of cancer in a living body by different mechanisms for each antibody.

Example 6: Analysis of Apoptosis-Inducing Capacity of Anti-ROR1 IgG Antibody

To analyze a possible mechanism of the antibody showing the tumor-inhibiting capacity as Example 5, the apoptosis-inducing capacity was analyzed.

For this, a ROR1 high expressing cell line, JeKo-1 was centrifuged, and the medium comprising serum was removed. It was washed once using PBS, and then $5\times10^6$ cells per well were seeded on a 6 well plate using RPMI1640 medium having no serum. After putting 100 μg/mL of the anti-ROR1 antibody of the present invention and 300 μg/ml of the anti-human Fc antibody (Thermo Fisher, 31125) in a equivalent tube at a ratio of 1:1, it was reacted at a room temperature for 10 mins, so that the cross-linked anti-ROR1 antibody forms through the anti-human Fc antibody. When 150 μl of the mixture was put into each well in which 1.5 ml of medium was included, so that the final amount of the antibody treated was to be 10 μg/mL for the anti-ROR1 antibody and 30 μg/mL for the anti-human Fc antibody. Then it was cultured under the condition of 5% $CO_2$, 37° C. for 24 hours and was reacted.

Then, to confirm whether the treatment of anti-ROR1 antibody and the cross-linked anti-ROR1 antibody have apoptosis capacity, cells from each well were collected and washed once with PBS. Afterward, Annexin V, a label of apoptosis, and PI, a label of cell death, were reacted on each group and the dyed degree was confirmed through FACS analysis.

Figure 10:
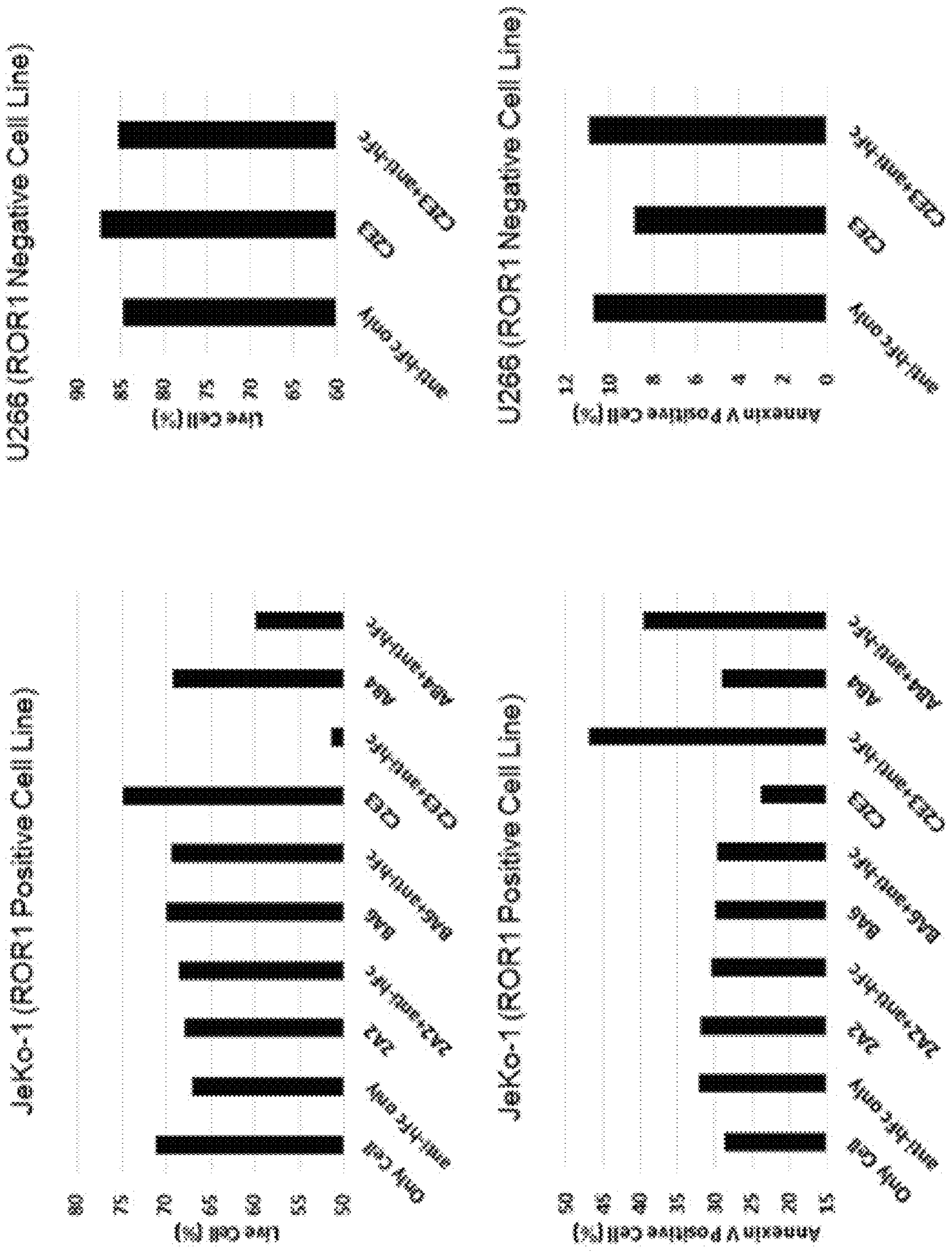
FIG. 10 is the result of analyzing the mechanism of the anti-ROR1 antibody prepared according to one embodiment of the present invention. The inhibition of the growth of cancer by the antibody may be shown by various mechanisms, for example, apoptosis induction, cancer cell division inhibition, cancer angiogenesis inhibition, and/or immunocyte activation, etc., and may show the same or different mechanism for each antibody.

The result was described in FIG. 10. It was confirmed that the apoptosis was not observed for the anti-ROR1 antibody treatment alone, but in case of some cross-linked anti-ROR1 antibody clones (C2E3, AB4) forming through the anti-human Fc antibody, the dyed degree of Annexin V and PI was increased as compared to the control group. In particular, it was confirmed that the dyed degree of the apoptosis capacity label, Annexin V, 23% and 10% were increased for C2E3 clone and AB4 clone, compared to the control group. To confirm if such an apoptosis capacity is a specific reaction induced by ROR1, the Annexin V and PI dyed degree was confirmed by the same method on non-ROR1-expressing cell lines, U266 using C2E3 clone, and it was confirmed that the apoptosis capacity was not induced for the ROR1 non-expressing cell line, U266. This demonstrates that the apoptosis capacity by the cross-linked anti-ROR1 antibody was a specific reaction associated with ROR1. As the cross-linked antibody can be formed by binding to an Fc gamma receptor through an Fc region in a living body, the cross-linked anti-ROR1 antibody with the anti-human Fc antibody can be considered to be a similar condition to in vivo phenomena. The result of analysis is one mechanism, and it means that the apoptosis can be induced in a cancer cell line overexpressing ROR1 by the anti-ROR1 antibody.

For reference, the apoptosis induction of the cancer cell line by cross-linked ROR1 antibody is not a phenomenon shown in all the kinds of ROR1 antibodies. For example, BA6 clone among the ROR1 antibodies of the present invention and 2A2 that was the antibody used as the comparison group did not induce apoptosis of the ROR1 overexpressing cancer cell line. This means that the ROR1 antibodies had the inhibiting capacity of cancer cell by different mechanisms each other. Such a difference is not limited to this theory, but may result from the dissimilarity of epitopes to which each ROR1 antibody binds.

The invention claimed is:

1. An isolated antibody specifically recognizing an extracellular domain of ROR1 or its antigen-binding fragment, wherein the antibody or antigen-binding fragment comprises (i) heavy chain complementarity determining regions of CDRH1, CDRH2 and CDRH3, and (ii) light chain complementarity determining regions of CDRL1, CDRL2 and CDRL3, and, wherein
(a) the CDRH1, CDRH2 and CDRH3 are SEQ ID NOs: 1, 6, and 14, respectively, and the CDRL1, CDRL2, and CDRL3 are SEQ ID NOs: 22, 30 and 38, respectively;
(b) the CDRH1, CDRH2 and CDRH3 are SEQ ID NOs: 2, 7, and 15, respectively, and the CDRL1, CDRL2, and CDRL3 are SEQ ID NOs: 23, 31 and 39, respectively;
(c) the CDRH1, CDRH2 and CDRH3 are SEQ ID NOs: 1, 8, and 16, respectively, and the CDRL1, CDRL2, and CDRL3 are SEQ ID NOs: 24, 32 and 40, respectively;
(d) the CDRH1, CDRH2 and CDRH3 are SEQ ID NOs: 3, 9, and 17, respectively, and the CDRL1, CDRL2, and CDRL3 are SEQ ID NOs: 25, 33 and 41, respectively;
(e) the CDRH1, CDRH2 and CDRH3 are SEQ ID NOs: 1, 10, and 18, respectively, and the CDRL1, CDRL2, and CDRL3 are SEQ ID NOs: 26, 34 and 41, respectively;
(f) the CDRH1, CDRH2 and CDRH3 are SEQ ID NOs: 4, 11, and 19, respectively, and the CDRL1, CDRL2, and CDRL3 are SEQ ID NOs: 27, 35 and 42, respectively;
(g) the CDRH1, CDRH2 and CDRH3 are SEQ ID NOs: 5, 12, and 20, respectively, and the CDRL1, CDRL2, and CDRL3 are SEQ ID NOs: 28, 36 and 41, respectively;
(h) the CDRH1, CDRH2 and CDRH3 are SEQ ID NOs: 3, 13, and 21, respectively, and the CDRL1, CDRL2, and CDRL3 are SEQ ID NOs: 29, 37 and 41, respectively;
(i) the CDRH1, CDRH2 and CDRH3 are SEQ ID NOs: 2, 96, and 15, respectively, and the CDRL1, CDRL2, and CDRL3 are SEQ ID NOs: 23, 31 and 39, respectively; or
(j) the CDRH1, CDRH2 and CDRH3 are SEQ ID NOs: 3, 9, and 97, respectively, and the CDRL1, CDRL2, and CDRL3 are SEQ ID NOs: 25, 33 and 41.

2. The isolated antibody specifically recognizing an extracellular domain of ROR1 or its antigen-binding fragment according to claim 1, comprising a combination of a heavy chain variable region and a light chain variable region, represented by the following sequence:
SEQ ID NOs: 43 and 51; SEQ ID NOs: 44 and 52; SEQ ID NOs: 45 and 53; SEQ ID NOs: 46 and 54; SEQ ID NOs: 47 and 55; SEQ ID NOs: 48 and 56; SEQ ID NO: 49 and 57; SEQ ID NOs: 50 and 58; SEQ ID NOs: 98 and 52; or SEQ ID NOs: 99 and 54.

3. The isolated antibody specifically recognizing an extracellular domain of ROR1 or its antigen-binding fragment according to claim 1, wherein the antibody or antigen-binding fragment is a monoclonal antibody.

4. The isolated antibody specifically recognizing an extracellular domain of ROR1 or its antigen-binding fragment according to claim 1, wherein the antibody is an IgG1, IgG2, IgG3 or IgG4 type.

5. The isolated antibody specifically recognizing an extracellular domain of ROR1 or its antigen-binding fragment according to claim 1, wherein the ROR1 is a human, monkey or mouse ROR1.

6. The isolated antibody specifically recognizing an extracellular domain of ROR1 or its antigen-binding fragment according to claim 1, wherein the antibody or antigen-binding fragment is Fab, Fab', F(ab')$_2$, scFab, Fv, dsFv, scFV, scFV-Fc, minibody, diabody, scAb, dAb, bivalent antibody or multivalent antibody.

7. An isolated polynucleotide encoding the antibody or its antigen-binding fragment according to claim 1.

8. A vector comprising the polynucleotide encoding the antibody or its antigen-binding fragment according to claim 1.

9. A cell line transformed with the vector comprising the polynucleotide encoding the antibody or its antigen-binding fragment according to claim 1.

10. A pharmaceutical composition, comprising the antibody or its antigen-binding fragment according to claim 1 and a pharmaceutically acceptable excipient.

11. A pharmaceutical composition for treatment or prevention of a disease related to overexpression of ROR1, comprising the antibody or its antigen-binding fragment according to claim 1 and a pharmaceutically acceptable excipient.

12. A pharmaceutical composition for treatment or prevention of a disease related to overexpression of ROR1, comprising the antibody or its antigen-binding fragment according to claim 1 and a pharmaceutically acceptable excipient, wherein the disease related to overexpression of ROR1 is cancer.

13. A method of detection of ROR1 in a biological sample comprising a step of contacting the antibody or its antigen-binding fragment according to claim 1 with a biological sample requiring detection of ROR1.

14. A method for diagnosing a disease related to overexpression of ROR1, comprising
a step of contacting the antibody or its antigen-binding fragment according to claim 1 with a biological sample, and
a step of determining the biological sample or a patient from who the biological sample is obtained as a disease related to overexpression of ROR1, when ROR1 is present or the concentration of ROR1 is increased in the biological sample as compared to a control group contacted with the antibody or its antigen-binding fragment, wherein the disease related to overexpression of ROR1 is cancer.

15. A method of treatment or prevention of a disease related to overexpression of ROR1, comprising a step of administering a therapeutically effective amount of the antibody or its antigen-binding fragment according to claim 1 to a subject in need of treatment or prevention of the disease.

16. The method of treatment or prevention of a disease related to overexpression of ROR1 according to claim 15, wherein the disease related to overexpression of ROR1 is cancer.

* * * * *

SEQUENCE LISTING

```
<160> NUMBER OF SEQ ID NOS: 103

<210> SEQ ID NO 1
<211> LENGTH: 5
<212> TYPE: PRT
```

-continued

<213> ORGANISM: Artificial Sequence
<220> FEATURE:
<223> OTHER INFORMATION: Synthetic: Heavy chain CDR1

<400> SEQUENCE: 1

Ser Tyr Asp Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic: Heavy chain CDR1

<400> SEQUENCE: 2

Asp Tyr Tyr Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic: Heavy chain CDR1

<400> SEQUENCE: 3

Asn Tyr Asp Met Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic: Heavy chain CDR1

<400> SEQUENCE: 4

Asn Tyr Ala Met Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic: Heavy chain CDR1

<400> SEQUENCE: 5

Asp Tyr Asp Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic: Heavy chain CDR2

<400> SEQUENCE: 6

Trp Ile Ser Pro Asp Ser Gly Ser Ile Tyr Tyr Ala Asp Ser Val Lys
1               5                   10                  15

Gly

<210> SEQ ID NO 7
<211> LENGTH: 17

-continued

<212> TYPE: PRT
<213> ORGANISM: Artificial Sequence
<220> FEATURE:
<223> OTHER INFORMATION: Synthetic: Heavy chain CDR2

<400> SEQUENCE: 7

Ser Ile Ser Pro Asp Gly Ser Asn Thr Tyr Tyr Ala Asp Ser Val Lys
1 5 10 15

Gly

<210> SEQ ID NO 8
<211> LENGTH: 17
<212> TYPE: PRT
<213> ORGANISM: Artificial Sequence
<220> FEATURE:
<223> OTHER INFORMATION: Synthetic: Heavy chain CDR2

<400> SEQUENCE: 8

Trp Ile Ser Pro Gly Gly Gly Ser Lys Tyr Tyr Ala Asp Ser Val Lys
1 5 10 15

Gly

<210> SEQ ID NO 9
<211> LENGTH: 17
<212> TYPE: PRT
<213> ORGANISM: Artificial Sequence
<220> FEATURE:
<223> OTHER INFORMATION: Synthetic: Heavy chain CDR2

<400> SEQUENCE: 9

Ala Ile Tyr His Ser Gly Ser Ser Lys Tyr Tyr Ala Asp Ser Val Lys
1 5 10 15

Gly

<210> SEQ ID NO 10
<211> LENGTH: 17
<212> TYPE: PRT
<213> ORGANISM: Artificial Sequence
<220> FEATURE:
<223> OTHER INFORMATION: Synthetic: Heavy chain CDR2

<400> SEQUENCE: 10

Gly Ile Ser His Gly Ser Gly Asn Lys Tyr Tyr Ala Asp Ser Val Lys
1 5 10 15

Gly

<210> SEQ ID NO 11
<211> LENGTH: 17
<212> TYPE: PRT
<213> ORGANISM: Artificial Sequence
<220> FEATURE:
<223> OTHER INFORMATION: Synthetic: Heavy chain CDR2

<400> SEQUENCE: 11

Ser Ile Ser His Asn Ser Gly Ser Thr Tyr Tyr Ala Asp Ser Val Lys
1 5 10 15

Gly

<210> SEQ ID NO 12
<211> LENGTH: 17
<212> TYPE: PRT
<213> ORGANISM: Artificial Sequence
<220> FEATURE:
<223> OTHER INFORMATION: Synthetic: Heavy chain CDR2

<400> SEQUENCE: 12

Val Ile Ser Pro Asp Gly Gly Ser Ile Tyr Tyr Ala Asp Ser Val Lys
1 5 10 15

Gly

<210> SEQ ID NO 13
<211> LENGTH: 18
<212> TYPE: PRT
<213> ORGANISM: Artificial Sequence
<220> FEATURE:
<223> OTHER INFORMATION: Synthetic: Heavy chain CDR2

<400> SEQUENCE: 13

Ser Ile Ser Pro Ser Ser Gly Ser Ser Ile Tyr Tyr Ala Asp Ser Val
1 5 10 15

Lys Gly

<210> SEQ ID NO 14
<211> LENGTH: 7
<212> TYPE: PRT
<213> ORGANISM: Artificial Sequence
<220> FEATURE:
<223> OTHER INFORMATION: Synthetic: Heavy chain CDR3

<400> SEQUENCE: 14

Pro Thr Gly Arg Phe Asp Tyr
1 5

<210> SEQ ID NO 15
<211> LENGTH: 7
<212> TYPE: PRT
<213> ORGANISM: Artificial Sequence
<220> FEATURE:
<223> OTHER INFORMATION: Synthetic: Heavy chain CDR3

<400> SEQUENCE: 15

Asn Leu Arg Ala Phe Asp Tyr
1 5

<210> SEQ ID NO 16
<211> LENGTH: 7
<212> TYPE: PRT
<213> ORGANISM: Artificial Sequence
<220> FEATURE:
<223> OTHER INFORMATION: Synthetic: Heavy chain CDR3

<400> SEQUENCE: 16

Val Asn Gly Arg Phe Asp Tyr
1 5

<210> SEQ ID NO 17
<211> LENGTH: 12
<212> TYPE: PRT
<213> ORGANISM: Artificial Sequence
<220> FEATURE:
<223> OTHER INFORMATION: Synthetic: Heavy chain CDR3

<400> SEQUENCE: 17

Gly Gly Asn Gly Ala Trp Asp Thr Gly Phe Asp Tyr
1 5 10

<210> SEQ ID NO 18
<211> LENGTH: 18
<212> TYPE: PRT

```
<213> ORGANISM: Artificial Sequence
<220> FEATURE:
<223> OTHER INFORMATION: Synthetic: Heavy chain CDR3

<400> SEQUENCE: 18

Arg Leu Ser Leu Arg Arg Arg Pro Ser Tyr Tyr Ser Asp Asn Ala Met
1               5                   10                  15

Asp Val


<210> SEQ ID NO 19
<211> LENGTH: 18
<212> TYPE: PRT
<213> ORGANISM: Artificial Sequence
<220> FEATURE:
<223> OTHER INFORMATION: Synthetic: Heavy chain CDR3

<400> SEQUENCE: 19

Phe Ile Ser Ala Arg Lys Ser Leu Gly Arg Ser Tyr Ser Asn Gly Met
1               5                   10                  15

Asp Val


<210> SEQ ID NO 20
<211> LENGTH: 18
<212> TYPE: PRT
<213> ORGANISM: Artificial Sequence
<220> FEATURE:
<223> OTHER INFORMATION: Synthetic: Heavy chain CDR3

<400> SEQUENCE: 20

Asp Val Val Glu Cys Asn Met Asn Pro Cys Ser Tyr Asp Asn Ala Met
1               5                   10                  15

Asp Val


<210> SEQ ID NO 21
<211> LENGTH: 18
<212> TYPE: PRT
<213> ORGANISM: Artificial Sequence
<220> FEATURE:
<223> OTHER INFORMATION: Synthetic: Heavy chain CDR3

<400> SEQUENCE: 21

Ala Pro Gly Trp Cys Gln Ala Pro Ser Cys Tyr Tyr Asp Asn Ala Met
1               5                   10                  15

Asp Val


<210> SEQ ID NO 22
<211> LENGTH: 13
<212> TYPE: PRT
<213> ORGANISM: Artificial Sequence
<220> FEATURE:
<223> OTHER INFORMATION: Synthetic: Light chain CDR1

<400> SEQUENCE: 22

Ser Gly Ser Ser Ser Asn Ile Gly Asn Asn Asn Val Asn
1               5                   10


<210> SEQ ID NO 23
<211> LENGTH: 13
<212> TYPE: PRT
<213> ORGANISM: Artificial Sequence
<220> FEATURE:
<223> OTHER INFORMATION: Synthetic: Light chain CDR1

<400> SEQUENCE: 23
```

Ser Gly Ser Ser Ser Asn Ile Gly Ser Asn Thr Val Tyr
1 5 10

<210> SEQ ID NO 24
<211> LENGTH: 13
<212> TYPE: PRT
<213> ORGANISM: Artificial Sequence
<220> FEATURE:
<223> OTHER INFORMATION: Synthetic: Light chain CDR1

<400> SEQUENCE: 24

Ser Gly Ser Ser Ser Asn Ile Gly Asn Asn Asn Val Ser
1 5 10

<210> SEQ ID NO 25
<211> LENGTH: 13
<212> TYPE: PRT
<213> ORGANISM: Artificial Sequence
<220> FEATURE:
<223> OTHER INFORMATION: Synthetic: Light chain CDR1

<400> SEQUENCE: 25

Ser Gly Ser Ser Ser Asn Ile Gly Ser Asn Asp Val Ser
1 5 10

<210> SEQ ID NO 26
<211> LENGTH: 13
<212> TYPE: PRT
<213> ORGANISM: Artificial Sequence
<220> FEATURE:
<223> OTHER INFORMATION: Synthetic: Light chain CDR1

<400> SEQUENCE: 26

Thr Gly Ser Ser Ser Asn Ile Gly Asn Asn Ala Val Asn
1 5 10

<210> SEQ ID NO 27
<211> LENGTH: 13
<212> TYPE: PRT
<213> ORGANISM: Artificial Sequence
<220> FEATURE:
<223> OTHER INFORMATION: Synthetic: Light chain CDR1

<400> SEQUENCE: 27

Thr Gly Ser Ser Ser Asn Ile Gly Ser Asn Asp Val Thr
1 5 10

<210> SEQ ID NO 28
<211> LENGTH: 13
<212> TYPE: PRT
<213> ORGANISM: Artificial Sequence
<220> FEATURE:
<223> OTHER INFORMATION: Synthetic: Light chain CDR1

<400> SEQUENCE: 28

Ser Gly Ser Ser Ser Asn Ile Gly Ser Asn Tyr Val Ser
1 5 10

<210> SEQ ID NO 29
<211> LENGTH: 13
<212> TYPE: PRT
<213> ORGANISM: Artificial Sequence
<220> FEATURE:
<223> OTHER INFORMATION: Synthetic: Light chain CDR1

<400> SEQUENCE: 29

Ser Gly Ser Ser Ser Asn Ile Gly Asn Asn Asp Val Ser 1 5 10

<210> SEQ ID NO 30
<211> LENGTH: 7
<212> TYPE: PRT
<213> ORGANISM: Artificial Sequence
<220> FEATURE:
<223> OTHER INFORMATION: Synthetic: Light chain CDR2

<400> SEQUENCE: 30

Tyr Asp Asn Lys Arg Pro Ser
1 5

<210> SEQ ID NO 31
<211> LENGTH: 7
<212> TYPE: PRT
<213> ORGANISM: Artificial Sequence
<220> FEATURE:
<223> OTHER INFORMATION: Synthetic: Light chain CDR2

<400> SEQUENCE: 31

Ala Asn Ser Gln Arg Pro Ser
1 5

<210> SEQ ID NO 32
<211> LENGTH: 7
<212> TYPE: PRT
<213> ORGANISM: Artificial Sequence
<220> FEATURE:
<223> OTHER INFORMATION: Synthetic: Light chain CDR2

<400> SEQUENCE: 32

Ala Asp Ser His Arg Pro Ser
1 5

<210> SEQ ID NO 33
<211> LENGTH: 7
<212> TYPE: PRT
<213> ORGANISM: Artificial Sequence
<220> FEATURE:
<223> OTHER INFORMATION: Synthetic: Light chain CDR2

<400> SEQUENCE: 33

Tyr Asp Asn Asn Arg Pro Ser
1 5

<210> SEQ ID NO 34
<211> LENGTH: 7
<212> TYPE: PRT
<213> ORGANISM: Artificial Sequence
<220> FEATURE:
<223> OTHER INFORMATION: Synthetic: Light chain CDR2

<400> SEQUENCE: 34

Tyr Asp Ser Asn Arg Pro Ser
1 5

<210> SEQ ID NO 35
<211> LENGTH: 7
<212> TYPE: PRT
<213> ORGANISM: Artificial Sequence
<220> FEATURE:
<223> OTHER INFORMATION: Synthetic: Light chain CDR2

<400> SEQUENCE: 35

Ala Asp Ser Lys Arg Pro Ser
1 5

<210> SEQ ID NO 36
<211> LENGTH: 7
<212> TYPE: PRT
<213> ORGANISM: Artificial Sequence
<220> FEATURE:
<223> OTHER INFORMATION: Synthetic: Light chain CDR2

<400> SEQUENCE: 36

Asp Asp Ser His Arg Pro Ser
1 5

<210> SEQ ID NO 37
<211> LENGTH: 7
<212> TYPE: PRT
<213> ORGANISM: Artificial Sequence
<220> FEATURE:
<223> OTHER INFORMATION: Synthetic: Light chain CDR2

<400> SEQUENCE: 37

Asp Asp Ser Gln Arg Pro Ser
1 5

<210> SEQ ID NO 38
<211> LENGTH: 11
<212> TYPE: PRT
<213> ORGANISM: Artificial Sequence
<220> FEATURE:
<223> OTHER INFORMATION: Synthetic: Light chain CDR3

<400> SEQUENCE: 38

Gly Thr Trp Asp Ala Ser Leu Ser Gly Tyr Val
1 5 10

<210> SEQ ID NO 39
<211> LENGTH: 11
<212> TYPE: PRT
<213> ORGANISM: Artificial Sequence
<220> FEATURE:
<223> OTHER INFORMATION: Synthetic: Light chain CDR3

<400> SEQUENCE: 39

Gly Ser Trp Asp Tyr Ser Leu Ser Gly Tyr Val
1 5 10

<210> SEQ ID NO 40
<211> LENGTH: 11
<212> TYPE: PRT
<213> ORGANISM: Artificial Sequence
<220> FEATURE:
<223> OTHER INFORMATION: Synthetic: Light chain CDR3

<400> SEQUENCE: 40

Ala Thr Trp Asp Tyr Ser Leu Ser Gly Tyr Val
1 5 10

<210> SEQ ID NO 41
<211> LENGTH: 11
<212> TYPE: PRT
<213> ORGANISM: Artificial Sequence
<220> FEATURE:
<223> OTHER INFORMATION: Synthetic: Light chain CDR3

<400> SEQUENCE: 41

Gly Ala Trp Asp Asp Ser Leu Ser Gly Tyr Val
1 5 10

```
<210> SEQ ID NO 42
<211> LENGTH: 11
<212> TYPE: PRT
<213> ORGANISM: Artificial Sequence
<220> FEATURE:
<223> OTHER INFORMATION: Synthetic: Light chain CDR3

<400> SEQUENCE: 42

Gly Thr Trp Asp Tyr Ser Leu Ser Gly Tyr Val
1               5                   10


<210> SEQ ID NO 43
<211> LENGTH: 116
<212> TYPE: PRT
<213> ORGANISM: Artificial Sequence
<220> FEATURE:
<223> OTHER INFORMATION: Synthetic: Heavy chain variable region

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Pro Asp Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Thr Gly Arg Phe Asp Tyr Trp Gly Gln Gly Thr Leu Val
            100                 105                 110

Thr Val Ser Ser
        115


<210> SEQ ID NO 44
<211> LENGTH: 116
<212> TYPE: PRT
<213> ORGANISM: Artificial Sequence
<220> FEATURE:
<223> OTHER INFORMATION: Synthetic: Heavy chain variable region

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ser Ile Ser Pro Asp Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Arg Ala Phe Asp Tyr Trp Gly Gln Gly Thr Leu Val
            100                 105                 110

Thr Val Ser Ser
```

115

<210> SEQ ID NO 45
<211> LENGTH: 116
<212> TYPE: PRT
<213> ORGANISM: Artificial Sequence
<220> FEATURE:
<223> OTHER INFORMATION: Synthetic: Heavy chain variable region

<400> SEQUENCE: 45

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Pro Gly Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Gly Arg Phe Asp Tyr Trp Gly Gln Gly Thr Leu Val
            100                 105                 110

Thr Val Ser Ser
        115
```

<210> SEQ ID NO 46
<211> LENGTH: 121
<212> TYPE: PRT
<213> ORGANISM: Artificial Sequence
<220> FEATURE:
<223> OTHER INFORMATION: Synthetic: Heavy chain variable region

<400> SEQUENCE: 46

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Ala Ile Tyr His Ser Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Gly Ala Trp Asp Thr Gly Phe Asp Tyr Trp Gly
            100                 105                 110

Gln Gly Thr Leu Val Thr Val Ser Ser
        115                 120
```

<210> SEQ ID NO 47
<211> LENGTH: 127
<212> TYPE: PRT
<213> ORGANISM: Artificial Sequence
<220> FEATURE:
<223> OTHER INFORMATION: Synthetic: Heavy chain variable region

<400> SEQUENCE: 47

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Gly Ile Ser His Gly Ser Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Leu Ser Leu Arg Arg Arg Pro Ser Tyr Tyr Ser Asp Asn
            100                 105                 110

Ala Met Asp Val Trp Gly Gln Gly Thr Leu Val Thr Val Ser Ser
        115                 120                 125

<210> SEQ ID NO 48
<211> LENGTH: 127
<212> TYPE: PRT
<213> ORGANISM: Artificial Sequence
<220> FEATURE:
<223> OTHER INFORMATION: Synthetic: Heavy chain variable region

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser His Asn Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ile Ser Ala Arg Lys Ser Leu Gly Arg Ser Tyr Ser Asn
            100                 105                 110

Gly Met Asp Val Trp Gly Gln Gly Thr Leu Val Thr Val Ser Ser
        115                 120                 125

<210> SEQ ID NO 49
<211> LENGTH: 127
<212> TYPE: PRT
<213> ORGANISM: Artificial Sequence
<220> FEATURE:
<223> OTHER INFORMATION: Synthetic: Heavy chain variable region

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Val Ile Ser Pro Asp Gly Gly Ser Ile Tyr Tyr Ala Asp Ser Val

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Val Val Glu Cys Asn Met Asn Pro Cys Ser Tyr Asp Asn
            100                 105                 110

Ala Met Asp Val Trp Gly Gln Gly Thr Leu Val Thr Val Ser Ser
        115                 120                 125


<210> SEQ ID NO 50
<211> LENGTH: 128
<212> TYPE: PRT
<213> ORGANISM: Artificial Sequence
<220> FEATURE:
<223> OTHER INFORMATION: Synthetic: Heavy chain variable region

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Ser Ile Ser Pro Ser Ser Gly Ser Ser Ile Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Ala Pro Gly Trp Cys Gln Ala Pro Ser Cys Tyr Tyr Asp
            100                 105                 110

Asn Ala Met Asp Val Trp Gly Gln Gly Thr Leu Val Thr Val Ser Ser
        115                 120                 125


<210> SEQ ID NO 51
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 51

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Asn Val Asn Trp Tyr Gln Gln Leu Pro Gly Thr Ala Pro Lys Leu Leu
        35                  40                  45

Ile Tyr Tyr Asp Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ala Ser Leu
                85                  90                  95

Ser Gly Tyr Val Phe Gly Gly Gly Thr Lys Leu Thr Val Leu Gly
            100                 105                 110
```

<210> SEQ ID NO 52
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 52

```
Gln Ser Val Leu Thr Gln Pro Pro Pro Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Tyr Trp Tyr Gln Gln Leu Pro Gly Thr Ala Pro Lys Leu Leu
        35                  40                  45

Ile Tyr Ala Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110
```

<210> SEQ ID NO 53
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 53

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Asn Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly
            100                 105                 110
```

<210> SEQ ID NO 54
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 54

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
```

```
        35                  40                  45

Ile Tyr Tyr Asp Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly
            100                 105                 110


<210> SEQ ID NO 55
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 55

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Tyr Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly
            100                 105                 110


<210> SEQ ID NO 56
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 56

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Asp Val Thr Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Phe Gly Gly Gly Thr Lys Leu Thr Val Leu Gly
            100                 105                 110


<210> SEQ ID NO 57
<211> LENGTH: 111
```

-continued

<212> TYPE: PRT
<213> ORGANISM: Artificial Sequence
<220> FEATURE:
<223> OTHER INFORMATION: Synthetic: Light chain variable region

<400> SEQUENCE: 57

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly
            100                 105                 110
```

<210> SEQ ID NO 58
<211> LENGTH: 111
<212> TYPE: PRT
<213> ORGANISM: Artificial Sequence
<220> FEATURE:
<223> OTHER INFORMATION: Synthetic: Light chain variable region

<400> SEQUENCE: 58

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly
            100                 105                 110
```

<210> SEQ ID NO 59
<211> LENGTH: 446
<212> TYPE: PRT
<213> ORGANISM: Artificial Sequence
<220> FEATURE:
<223> OTHER INFORMATION: Synthetic: Heavy chain

<400> SEQUENCE: 59

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Pro Asp Ser Gly Ser Ile Tyr Tyr Ala Asp Ser Val
```

-continued

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Thr Gly Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 60
<211> LENGTH: 446
<212> TYPE: PRT
<213> ORGANISM: Artificial Sequence -continued
<220> FEATURE:
<223> OTHER INFORMATION: Synthetic: Heavy chain

<400> SEQUENCE: 60

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ser Ile Ser Pro Asp Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Arg Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

-continued

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 61
<211> LENGTH: 446
<212> TYPE: PRT
<213> ORGANISM: Artificial Sequence
<220> FEATURE:
<223> OTHER INFORMATION: Synthetic: Heavy chain

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Pro Gly Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Gly Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 62
<211> LENGTH: 451
<212> TYPE: PRT
<213> ORGANISM: Artificial Sequence
<220> FEATURE:
<223> OTHER INFORMATION: Synthetic: Heavy chain

<400> SEQUENCE: 62

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Asp Met Ser Trp Val Arg Gln Ala Pro Gly Lys Gly Leu Glu Trp Val
35 40 45

Ser Ala Ile Tyr His Ser Gly Ser Ser Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Asn Gly Ala Trp Asp Thr Gly Phe Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Glu Glu Met Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 63
<211> LENGTH: 457
<212> TYPE: PRT
<213> ORGANISM: Artificial Sequence
<220> FEATURE:
<223> OTHER INFORMATION: Synthetic: Heavy chain

<400> SEQUENCE: 63

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Asp Met Ser Trp Val Arg Gln Ala Pro Gly Lys Gly Leu Glu Trp Val
35 40 45

Ser Gly Ile Ser His Gly Ser Gly Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Arg Leu Ser Leu Arg Arg Arg Pro Ser Tyr Tyr Ser Asp Asn
100 105 110

Ala Met Asp Val Trp Gly Gln Gly Thr Leu Val Thr Val Ser Ser Ala
115 120 125

Ser Thr Lys Gly Pro Ser Val Phe Pro Leu Ala Pro Ser Ser Lys Ser
130 135 140

-continued

Thr Ser Gly Gly Thr Ala Ala Leu Gly Cys Leu Val Lys Asp Tyr Phe
145 150 155 160

Pro Glu Pro Val Thr Val Ser Trp Asn Ser Gly Ala Leu Thr Ser Gly
165 170 175

Val His Thr Phe Pro Ala Val Leu Gln Ser Ser Gly Leu Tyr Ser Leu
180 185 190

Ser Ser Val Val Thr Val Pro Ser Ser Ser Leu Gly Thr Gln Thr Tyr
195 200 205

Ile Cys Asn Val Asn His Lys Pro Ser Asn Thr Lys Val Asp Lys Lys
210 215 220

Val Glu Pro Lys Ser Cys Asp Lys Thr His Thr Cys Pro Pro Cys Pro
225 230 235 240

Ala Pro Glu Leu Leu Gly Gly Pro Ser Val Phe Leu Phe Pro Pro Lys
245 250 255

Pro Lys Asp Thr Leu Met Ile Ser Arg Thr Pro Glu Val Thr Cys Val
260 265 270

Val Val Asp Val Ser His Glu Asp Pro Glu Val Lys Phe Asn Trp Tyr
275 280 285

Val Asp Gly Val Glu Val His Asn Ala Lys Thr Lys Pro Arg Glu Glu
290 295 300

Gln Tyr Asn Ser Thr Tyr Arg Val Val Ser Val Leu Thr Val Leu His
305 310 315 320

Gln Asp Trp Leu Asn Gly Lys Glu Tyr Lys Cys Lys Val Ser Asn Lys
325 330 335

Ala Leu Pro Ala Pro Ile Glu Lys Thr Ile Ser Lys Ala Lys Gly Gln
340 345 350

Pro Arg Glu Pro Gln Val Tyr Thr Leu Pro Pro Ser Arg Glu Glu Met
355 360 365

Thr Lys Asn Gln Val Ser Leu Thr Cys Leu Val Lys Gly Phe Tyr Pro
370 375 380

Ser Asp Ile Ala Val Glu Trp Glu Ser Asn Gly Gln Pro Glu Asn Asn
385 390 395 400

Tyr Lys Thr Thr Pro Pro Val Leu Asp Ser Asp Gly Ser Phe Phe Leu
405 410 415

Tyr Ser Lys Leu Thr Val Asp Lys Ser Arg Trp Gln Gln Gly Asn Val
420 425 430

Phe Ser Cys Ser Val Met His Glu Ala Leu His Asn His Tyr Thr Gln
435 440 445

Lys Ser Leu Ser Leu Ser Pro Gly Lys
450 455

<210> SEQ ID NO 64
<211> LENGTH: 457
<212> TYPE: PRT
<213> ORGANISM: Artificial Sequence
<220> FEATURE:
<223> OTHER INFORMATION: Synthetic: Heavy chain

<400> SEQUENCE: 64

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Ser Trp Val Arg Gln Ala Pro Gly Lys Gly Leu Glu Trp Val
35 40 45

```
Ser Ser Ile Ser His Asn Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ile Ser Ala Arg Lys Ser Leu Gly Arg Ser Tyr Ser Asn
            100                 105                 110

Gly Met Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455
```

<210> SEQ ID NO 65
<211> LENGTH: 457
<212> TYPE: PRT
<213> ORGANISM: Artificial Sequence
<220> FEATURE:
<223> OTHER INFORMATION: Synthetic: Heavy chain

<400> SEQUENCE: 65

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Val Ile Ser Pro Asp Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Val Val Glu Cys Asn Met Asn Pro Cys Ser Tyr Asp Asn
            100                 105                 110

Ala Met Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365
```

-continued

```
Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455


<210> SEQ ID NO 66
<211> LENGTH: 458
<212> TYPE: PRT
<213> ORGANISM: Artificial Sequence
<220> FEATURE:
<223> OTHER INFORMATION: Synthetic: Heavy chain

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Ser Ile Ser Pro Ser Ser Gly Ser Ser Ile Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Ala Pro Gly Trp Cys Gln Ala Pro Ser Cys Tyr Tyr Asp
            100                 105                 110

Asn Ala Met Asp Val Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270
```

-continued

```
Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455


<210> SEQ ID NO 67
<211> LENGTH: 216
<212> TYPE: PRT
<213> ORGANISM: Artificial Sequence
<220> FEATURE:
<223> OTHER INFORMATION: Synthetic: Light chain

<400> SEQUENCE: 67

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Asn Val Asn Trp Tyr Gln Gln Leu Pro Gly Thr Ala Pro Lys Leu Leu
        35                  40                  45

Ile Tyr Tyr Asp Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ala Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175
```

```
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215


<210> SEQ ID NO 68
<211> LENGTH: 216
<212> TYPE: PRT
<213> ORGANISM: Artificial Sequence
<220> FEATURE:
<223> OTHER INFORMATION: Synthetic: Light chain

<400> SEQUENCE: 68

Gln Ser Val Leu Thr Gln Pro Pro Pro Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Tyr Trp Tyr Gln Gln Leu Pro Gly Thr Ala Pro Lys Leu Leu
        35                  40                  45

Ile Tyr Ala Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215


<210> SEQ ID NO 69
<211> LENGTH: 216
<212> TYPE: PRT
<213> ORGANISM: Artificial Sequence
<220> FEATURE:
<223> OTHER INFORMATION: Synthetic: Light chain

<400> SEQUENCE: 69

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Asn Val Ser Trp Tyr Gln Gln Leu Pro Gly Thr Ala Pro Lys Leu Leu
        35                  40                  45
```

```
Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215


<210> SEQ ID NO 70
<211> LENGTH: 216
<212> TYPE: PRT
<213> ORGANISM: Artificial Sequence
<220> FEATURE:
<223> OTHER INFORMATION: Synthetic: Light chain

<400> SEQUENCE: 70

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Tyr Asp Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190
```

```
Arg Ser Tyr Ser Cys Gln Val Thr His Glu Gly Ser Thr Val Glu Lys
        195                 200                 205

Thr Val Ala Pro Ala Glu Cys Ser
    210                 215


<210> SEQ ID NO 71
<211> LENGTH: 216
<212> TYPE: PRT
<213> ORGANISM: Artificial Sequence
<220> FEATURE:
<223> OTHER INFORMATION: Synthetic: Light chain

<400> SEQUENCE: 71

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Tyr Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215


<210> SEQ ID NO 72
<211> LENGTH: 216
<212> TYPE: PRT
<213> ORGANISM: Artificial Sequence
<220> FEATURE:
<223> OTHER INFORMATION: Synthetic: Light chain

<400> SEQUENCE: 72

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Asp Val Thr Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
```

```
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215


<210> SEQ ID NO 73
<211> LENGTH: 216
<212> TYPE: PRT
<213> ORGANISM: Artificial Sequence
<220> FEATURE:
<223> OTHER INFORMATION: Synthetic: Light chain

<400> SEQUENCE: 73

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
```

```
        195                 200                 205

Thr Val Ala Pro Ala Glu Cys Ser
    210                 215


<210> SEQ ID NO 74
<211> LENGTH: 216
<212> TYPE: PRT
<213> ORGANISM: Artificial Sequence
<220> FEATURE:
<223> OTHER INFORMATION: Synthetic: Light chain

<400> SEQUENCE: 74

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215


<210> SEQ ID NO 75
<211> LENGTH: 1338
<212> TYPE: DNA
<213> ORGANISM: Artificial Sequence
<220> FEATURE:
<223> OTHER INFORMATION: Synthetic: Heavy chain coding gene

<400> SEQUENCE: 75

gaagtacaac ttctggagtc aggtggagga cttgttcagc ccggcgggtc cctgaggctg      60

agttgcgcag caagcgggtt cacattctcc tcttatgata tgtcttgggt aagacaggct     120

cctggtaagg gtctggaatg ggtatcctgg ataagtcctg actccggttc aatatactac     180

gccgatagtg tgaagggacg tttcaccatc agccgggaca acagcaaaaa taccttgtat     240

ctccaaatga atagcctccg ggctgaagac actgccgtat attactgcgc cagacctact     300

ggtcgttttg actattgggg gcaaggaaca ctggtaaccg tttcaagcgc ctccaccaag     360
```

-continued

```
ggcccctccg tgttccccct ggcccctcc tccaagtcca cctccggcgg caccgccgcc    420
ctgggctgcc tggtgaagga ctacttcccc gagcccgtga ccgtgtcctg gaactccggc    480
gccctgacct ccggcgtgca caccttcccc gccgtgctgc agtcctccgg cctgtactcc    540
ctgtcctccg tcgtgaccgt gccctcctcc tccctgggca cccagaccta catctgcaac    600
gtgaaccaca agccctccaa caccaaggtg gacaagaagg tggagcccaa gtcctgcgac    660
aagacccaca cctgccctcc ctgccccgcc cccgagctgc tgggcggccc ctccgtgttc    720
ctgttccctc ctaagcccaa ggacaccctg atgatctccc ggacccccga ggtgacttgc    780
gtggtggtgg acgtgtccca cgaggacccc gaggtgaagt tcaactggta cgtggacggc    840
gtggaggtgc acaacgccaa gaccaagccc cgggaggagc agtacaactc cacctaccgg    900
gtggtgtccg tgctgaccgt gctgcaccag gactggctga acggcaagga gtacaagtgc    960
aaggtgtcca acaaggccct gcccgccccc atcgagaaga ccatctccaa ggccaagggc   1020
cagccccggg agccccaggt gtacaccctg ccccctccc gggaggagat gaccaagaac   1080
caggtgtccc tgacctgcct ggtgaagggc ttctacccct ccgacatcgc cgtggagtgg   1140
gagtccaacg gccagcccga gaacaactac aagaccaccc cccccgtgct ggactccgac   1200
ggctccttct tcctgtactc caagctgacc gtggacaagt cccggtggca gcagggcaac   1260
gtgttctcct gctccgtgat gcacgaggcc ctgcacaacc actacaccca gaagtccctg   1320
tccctgtccc ccggcaag                                                 1338
```

<210> SEQ ID NO 76
<211> LENGTH: 1338
<212> TYPE: DNA
<213> ORGANISM: Artificial Sequence
<220> FEATURE:
<223> OTHER INFORMATION: Synthetic: Heavy chain coding gene

<400> SEQUENCE: 76

```
gaagtgcagc tgctggaatc cggcggaggc ctggtgcagc ctggcggctc tctgagactg     60
tcttgcgccg cctccggctt caccttctcc gactactaca tgtcctgggt gcgacaggcc    120
cctggcaagg gcctggaatg ggtgtcctcc atctcccccg acggctccaa cacctactac    180
gccgactccg tgaagggccg gttcaccatc tcccgggaca actccaagaa caccctgtac    240
ctgcagatga actccctgcg ggccgaggac accgccgtgt actactgcgc caagaacctg    300
cgggccttcg actactgggg ccagggcaca ctggtgaccg tgtcctccgc ctccaccaag    360
ggcccctccg tgttccccct ggcccctcc tccaagtcca cctccggcgg caccgccgcc    420
ctgggctgcc tggtgaagga ctacttcccc gagcccgtga ccgtgtcctg gaactccggc    480
gccctgacct ccggcgtgca caccttcccc gccgtgctgc agtcctccgg cctgtactcc    540
ctgtcctccg tcgtgaccgt gccctcctcc tccctgggca cccagaccta catctgcaac    600
gtgaaccaca agccctccaa caccaaggtg gacaagaagg tggagcccaa gtcctgcgac    660
aagacccaca cctgccctcc ctgccccgcc cccgagctgc tgggcggccc ctccgtgttc    720
ctgttccctc ctaagcccaa ggacaccctg atgatctccc ggacccccga ggtgacttgc    780
gtggtggtgg acgtgtccca cgaggacccc gaggtgaagt tcaactggta cgtggacggc    840
gtggaggtgc acaacgccaa gaccaagccc cgggaggagc agtacaactc cacctaccgg    900
gtggtgtccg tgctgaccgt gctgcaccag gactggctga acggcaagga gtacaagtgc    960
aaggtgtcca acaaggccct gcccgccccc atcgagaaga ccatctccaa ggccaagggc   1020
cagccccggg agccccaggt gtacaccctg ccccctccc gggaggagat gaccaagaac   1080
```

caggtgtccc tgacctgcct ggtgaagggc ttctacccct ccgacatcgc cgtggagtgg 1140
gagtccaacg gccagcccga gaacaactac aagaccaccc cccccgtgct ggactccgac 1200
ggctccttct tcctgtactc caagctgacc gtggacaagt cccggtggca gcagggcaac 1260
gtgttctcct gctccgtgat gcacgaggcc ctgcacaacc actacaccca gaagtccctg 1320
tccctgtccc ccggcaag 1338

<210> SEQ ID NO 77
<211> LENGTH: 1341
<212> TYPE: DNA
<213> ORGANISM: Artificial Sequence
<220> FEATURE:
<223> OTHER INFORMATION: Synthetic: Heavy chain coding gene

<400> SEQUENCE: 77
gaagtgcaac ttcttgagag tggtggagga ttggtacaac ctggggggtag tttgcgtctc 60 tcctgtgctg cttctggttt cacattttcc tcctatgaca tgagctgggt acggcaagct 120
ccaggaaaag ggcttgagtg ggtctcctgg atctctcccg gtggaggcag caagtattat 180
gcagactctg taaagggtag gtttactata tcacgcgata atagtaagaa tactttgtat 240
ttgcaaatga actccctccg agctgaggac acagcagtct attattgcgc ccgagttaac 300
ggtcgcttcg attactgggg ccaaggcaca ctggttacag tgtcctcagc ctccaccaag 360
ggcccctccg tgttccccct ggccccctcc tccaagtcca cctccggcgg caccgccgcc 420
ctgggctgcc tggtgaagga ctacttcccc gagcccgtga ccgtgtcctg gaactccggc 480
gccctgacct ccggcgtgca caccttcccc gccgtgctgc agtcctccgg cctgtactcc 540
ctgtcctccg tcgtgaccgt gccctcctcc tccctgggca cccagaccta catctgcaac 600
gtgaaccaca agccctccaa caccaaggtg gacaagaagg tggagcccaa gtcctgcgac 660
aagacccaca cctgccctcc ctgccccgcc cccgagctgc tgggcggccc ctccgtgttc 720
ctgttccctc ctaagcccaa ggacaccctg atgatctccc ggacccccga ggtgacttgc 780
gtggtggtgg acgtgtccca cgaggacccc gaggtgaagt tcaactggta cgtggacggc 840
gtggaggtgc acaacgccaa gaccaagccc cgggaggagc agtacaactc cacctaccgg 900
gtggtgtccg tgctgaccgt gctgcaccag gactggctga acggcaagga gtacaagtgc 960
aaggtgtcca acaaggccct gcccgccccc atcgagaaga ccatctccaa ggccaagggc 1020
cagccccggg agccccaggt gtacaccctg ccccccctccc gggaggagat gaccaagaac 1080
caggtgtccc tgacctgcct ggtgaagggc ttctacccct ccgacatcgc cgtggagtgg 1140
gagtccaacg gccagcccga gaacaactac aagaccaccc cccccgtgct ggactccgac 1200
ggctccttct tcctgtactc caagctgacc gtggacaagt cccggtggca gcagggcaac 1260
gtgttctcct gctccgtgat gcacgaggcc ctgcacaacc actacaccca gaagtccctg 1320
tccctgtccc ccggcaagtg a 1341

<210> SEQ ID NO 78
<211> LENGTH: 1353
<212> TYPE: DNA
<213> ORGANISM: Artificial Sequence
<220> FEATURE:
<223> OTHER INFORMATION: Synthetic: Heavy chain coding gene

<400> SEQUENCE: 78
gaggtgcagc tgctggagtc cggcggcggc ctggtgcagc ccggcggctc cctgcggctg 60

```
tcctgcgccg cctccggctt caccttctcc aactacgaca tgtcctgggt gcggcaggcc    120

cccggcaagg gcctggagtg ggtgtccgcc atctaccact ccggctcctc caagtactac    180

gccgactccg tgaagggccg gttcaccatc tcccgggaca actccaagaa caccctgtac    240

ctgcagatga actccctgcg ggccgaggac accgccgtgt actactgcgc ccggggcggc    300

aacggcgcct gggacaccgg cttcgactac tggggccagg gcaccctggt gaccgtgtcc    360

tccgcctcca ccaagggccc ctccgtgttc cccctggccc cctcctccaa gtccacctcc    420

ggcggcaccg ccgccctggg ctgcctggtg aaggactact tccccgagcc cgtgaccgtg    480

tcctggaact ccggcgccct gacctccggc gtgcacacct tccccgccgt gctgcagtcc    540

tccggcctgt actccctgtc ctccgtcgtg accgtgccct cctcctccct gggcacccag    600

acctacatct gcaacgtgaa ccacaagccc tccaacacca aggtggacaa gaaggtggag    660

cccaagtcct gcgacaagac ccacacctgc cctccctgcc ccgcccccga gctgctgggc    720

ggcccctccg tgttcctgtt ccctcctaag cccaaggaca ccctgatgat ctcccggacc    780

cccgaggtga cttgcgtggt ggtggacgtg tcccacgagg accccgaggt gaagttcaac    840

tggtacgtgg acggcgtgga ggtgcacaac gccaagacca agccccggga ggagcagtac    900

aactccacct accgggtggt gtccgtgctg accgtgctgc accaggactg gctgaacggc    960

aaggagtaca agtgcaaggt gtccaacaag gccctgcccg cccccatcga gaagaccatc   1020

tccaaggcca agggccagcc ccgggagccc caggtgtaca ccctgccccc ctcccgggag   1080

gagatgacca agaaccaggt gtccctgacc tgcctggtga agggcttcta cccctccgac   1140

atcgccgtgg agtgggagtc caacggccag cccgagaaca actacaagac caccccccc   1200

gtgctggact ccgacggctc cttcttcctg tactccaagc tgaccgtgga caagtcccgg   1260

tggcagcagg gcaacgtgtt ctcctgctcc gtgatgcacg aggccctgca caaccactac   1320

acccagaagt ccctgtccct gtcccccggc aag                                1353
```

<210> SEQ ID NO 79
<211> LENGTH: 1374
<212> TYPE: DNA
<213> ORGANISM: Artificial Sequence
<220> FEATURE:
<223> OTHER INFORMATION: Synthetic: Heavy chain coding gene

<400> SEQUENCE: 79

```
gaagttcaac tgttggaatc cgggggtggt ctggtccaac ctggagggtc tcttagactg     60

agttgtgctg cttcaggctt cacatttagc tcatatgata tgtcctgggt cagacaggcc    120

cccggcaaag gtcttgaatg ggtatctggt attagtcatg gatctggcaa caagtactac    180

gctgatagtg tcaaaggacg attcaccata tctcgtgaca actctaaaaa cactttgtac    240

ttgcagatga actcactgcg tgccgaagac acagccgtgt attattgcgc taagcgtctc    300

tcactccgca ggcgaccttc ctattacagc gacaacgcta tggatgtctg gggcagggt     360

acactcgtca ccgtgtcatc agcctccacc aagggcccct ccgtgttccc cctggccccc    420

tcctccaagt ccacctccgg cggcaccgcc gccctgggct gcctggtgaa ggactacttc    480

cccgagcccg tgaccgtgtc ctggaactcc ggcgccctga cctccggcgt gcacaccttc    540

cccgccgtgc tgcagtcctc cggcctgtac tccctgtcct ccgtcgtgac cgtgccctcc    600

tcctccctgg gcacccagac ctacatctgc aacgtgaacc acaagccctc caacaccaag    660

gtggacaaga aggtggagcc caagtcctgc gacaagaccc acacctgccc tccctgcccc    720

gcccccgagc tgctgggcgg cccctccgtg ttcctgttcc ctcctaagcc caaggacacc    780
```

```
ctgatgatct cccggacccc cgaggtgact tgcgtggtgg tggacgtgtc ccacgaggac    840

cccgaggtga agttcaactg gtacgtggac ggcgtggagg tgcacaacgc caagaccaag    900

ccccgggagg agcagtacaa ctccacctac cgggtggtgt ccgtgctgac cgtgctgcac    960

caggactggc tgaacggcaa ggagtacaag tgcaaggtgt ccaacaaggc cctgcccgcc   1020

cccatcgaga agaccatctc caaggccaag ggccagcccc gggagcccca ggtgtacacc   1080

ctgccccccct cccgggagga gatgaccaag aaccaggtgt ccctgacctg cctggtgaag   1140

ggcttctacc cctccgacat cgccgtggag tgggagtcca acggccagcc cgagaacaac   1200

tacaagacca ccccccccgt gctggactcc gacggctcct tcttcctgta ctccaagctg   1260

accgtggaca agtcccggtg gcagcagggc aacgtgttct cctgctccgt gatgcacgag   1320

gccctgcaca accactacac ccagaagtcc ctgtccctgt cccccggcaa gtga         1374
```

<210> SEQ ID NO 80
<211> LENGTH: 1371
<212> TYPE: DNA
<213> ORGANISM: Artificial Sequence
<220> FEATURE:
<223> OTHER INFORMATION: Synthetic: Heavy chain coding gene

<400> SEQUENCE: 80

```
gaggtgcagc tgctggagtc cggcggcggc ctggtgcagc ccggcggctc cctgcggctg     60

tcctgcgccg cctccggctt caccttctcc aactacgcca tgtcctgggt gcggcaggcc    120

cccggcaagg gcctggagtg ggtgtcctcc atctcccaca actccggctc cacctactac    180

gccgactccg tgaagggccg gttcaccatc tcccgggaca actccaagaa caccctgtac    240

ctgcagatga actccctgcg ggccgaggac accgccgtgt actactgcgc caagttcatc    300

tccgcccgga agtccctggg ccggtcctac tccaacggca tggacgtgtg gggccagggc    360

accctggtga ccgtgtcctc cgcctccacc aagggcccct ccgtgttccc cctggccccc    420

tcctccaagt ccacctccgg cggcaccgcc gccctgggct gcctggtgaa ggactacttc    480

cccgagcccg tgaccgtgtc ctggaactcc ggcgccctga cctccggcgt gcacaccttc    540

cccgccgtgc tgcagtcctc cggcctgtac tccctgtcct ccgtcgtgac cgtgccctcc    600

tcctccctgg gcacccagac ctacatctgc aacgtgaacc acaagccctc caacaccaag    660

gtggacaaga aggtggagcc caagtcctgc gacaagaccc acacctgccc tccctgcccc    720

gcccccgagc tgctgggcgg cccctccgtg ttcctgttcc ctcctaagcc caaggacacc    780

ctgatgatct cccggacccc cgaggtgact tgcgtggtgg tggacgtgtc ccacgaggac    840

cccgaggtga agttcaactg gtacgtggac ggcgtggagg tgcacaacgc caagaccaag    900

ccccgggagg agcagtacaa ctccacctac cgggtggtgt ccgtgctgac cgtgctgcac    960

caggactggc tgaacggcaa ggagtacaag tgcaaggtgt ccaacaaggc cctgcccgcc   1020

cccatcgaga agaccatctc caaggccaag ggccagcccc gggagcccca ggtgtacacc   1080

ctgccccccct cccgggagga gatgaccaag aaccaggtgt ccctgacctg cctggtgaag   1140

ggcttctacc cctccgacat cgccgtggag tgggagtcca acggccagcc cgagaacaac   1200

tacaagacca ccccccccgt gctggactcc gacggctcct tcttcctgta ctccaagctg   1260

accgtggaca agtcccggtg gcagcagggc aacgtgttct cctgctccgt gatgcacgag   1320

gccctgcaca accactacac ccagaagtcc ctgtccctgt cccccggcaa g            1371
```

<210> SEQ ID NO 81

<211> LENGTH: 1371
<212> TYPE: DNA
<213> ORGANISM: Artificial Sequence
<220> FEATURE:
<223> OTHER INFORMATION: Synthetic: Heavy chain coding gene

<400> SEQUENCE: 81
gaagtacagt tgcttgaaag tggcggtggt cttgtccagc caggcggttc ccttcggctg 60
tcttgcgccg caagtggctt cactttcagc gactatgata tgtcttgggt ccgccaagca 120
ccaggaaagg gacttgaatg ggtgagtgta atcagtcctg acggagggtc aatttattat 180
gcagattcag tcaagggtcg attcactata tcccgagaca actccaaaaa tactctttat 240
cttcagatga actctttgag agctgaagac accgcagttt attactgtgc tcgggatgta 300
gtggagtgca atatgaatcc ctgctcatac gacaacgcaa tggatgtttg gggcagggg 360 actctggtga cagtcagctc tgcctccacc aagggcccct ccgtgttccc cctggccccc 420
tcctccaagt ccacctccgg cggcaccgcc gccctgggct gcctggtgaa ggactacttc 480
cccgagcccg tgaccgtgtc ctggaactcc ggcgccctga cctccggcgt gcacaccttc 540
cccgccgtgc tgcagtcctc cggcctgtac tccctgtcct ccgtcgtgac cgtgccctcc 600
tcctccctgg gcacccagac ctacatctgc aacgtgaacc acaagccctc caacaccaag 660
gtggacaaga aggtggagcc caagtcctgc gacaagaccc acacctgccc tccctgcccc 720
gcccccgagc tgctgggcgg cccctccgtg ttcctgttcc ctcctaagcc caaggacacc 780
ctgatgatct cccggacccc cgaggtgact tgcgtggtgg tggacgtgtc ccacgaggac 840
cccgaggtga agttcaactg gtacgtggac ggcgtggagg tgcacaacgc caagaccaag 900
ccccgggagg agcagtacaa ctccacctac cgggtggtgt ccgtgctgac cgtgctgcac 960
caggactggc tgaacggcaa ggagtacaag tgcaaggtgt ccaacaaggc cctgcccgcc 1020
cccatcgaga agaccatctc caaggccaag ggccagcccc gggagcccca ggtgtacacc 1080 ctgccccct cccgggagga gatgaccaag aaccaggtgt ccctgacctg cctggtgaag 1140
ggcttctacc cctccgacat cgccgtggag tgggagtcca acggccagcc cgagaacaac 1200
tacaagacca cccccccgt gctggactcc gacggctcct tcttcctgta ctccaagctg 1260
accgtggaca agtcccggtg gcagcagggc aacgtgttct cctgctccgt gatgcacgag 1320
gccctgcaca accactacac ccagaagtcc ctgtccctgt cccccggcaa g 1371

<210> SEQ ID NO 82
<211> LENGTH: 1374
<212> TYPE: DNA
<213> ORGANISM: Artificial Sequence
<220> FEATURE:
<223> OTHER INFORMATION: Synthetic: Heavy chain coding gene

<400> SEQUENCE: 82
gaagtgcagc tgcttgaatc aggaggcggc ctcgtacaac caggggggatc tctcagactg 60 tcctgcgctg ccagtggctt cactttcagc aactacgata tgtcatgggt gaggcaggca 120
cctggcaagg gtctggagtg ggtctcaagc ataagtccca gtagtggaag ctcaatttat 180
tacgccgaca gtgtaaaggg ccggttcacc attagtagag acaattctaa gaataccttg 240
taccttcaaa tgaatagtct gagagccgaa gataccgcag tttattattg cgctaaggcc 300
ccagggtggt gtcaggcccc ttcatgctat tatgataatg caatggacgt gtggggtcag 360
ggtactctgg tcacagtcag tagtgcctcc accaagggcc cctccgtgtt ccccctggcc 420
ccctcctcca agtccacctc cggcggcacc gccgccctgg gctgcctggt gaaggactac 480

```
ttccccgagc ccgtgaccgt gtcctggaac tccggcgccc tgacctccgg cgtgcacacc    540

ttccccgccg tgctgcagtc ctccggcctg tactccctgt cctccgtcgt gaccgtgccc    600

tcctcctccc tgggcaccca gacctacatc tgcaacgtga accacaagcc ctccaacacc    660

aaggtggaca agaaggtgga gcccaagtcc tgcgacaaga cccacacctg ccctccctgc    720

cccgcccccg agctgctggg cggcccctcc gtgttcctgt tccctcctaa gcccaaggac    780

accctgatga tctcccggac ccccgaggtg acttgcgtgg tggtggacgt gtcccacgag    840

gaccccgagg tgaagttcaa ctggtacgtg gacggcgtgg aggtgcacaa cgccaagacc    900

aagccccggg aggagcagta caactccacc taccgggtgg tgtccgtgct gaccgtgctg    960

caccaggact ggctgaacgg caaggagtac aagtgcaagg tgtccaacaa ggccctgccc   1020

gcccccatcg agaagaccat ctccaaggcc aagggccagc ccgggagcc ccaggtgtac   1080

accctgcccc cctcccggga ggagatgacc aagaaccagg tgtccctgac ctgcctggtg   1140

aagggcttct accccctccga catcgccgtg gagtgggagt ccaacggcca gcccgagaac   1200

aactacaaga ccaccccccc cgtgctggac tccgacggct ccttcttcct gtactccaag   1260

ctgaccgtgg acaagtcccg gtggcagcag ggcaacgtgt tctcctgctc cgtgatgcac   1320

gaggccctgc acaaccacta cacccagaag tccctgtccc tgtcccccgg caag         1374
```

<210> SEQ ID NO 83
<211> LENGTH: 648
<212> TYPE: DNA
<213> ORGANISM: Artificial Sequence
<220> FEATURE:
<223> OTHER INFORMATION: Synthetic: Light chain coding gene

<400> SEQUENCE: 83

```
cagtctgtgc tgacacaacc accttctgcc tctgggactc caggccagcg ggttaccatt     60

agctgttctg gtagttctag taatatcggt aacaacaatg tgaattggta tcaacaactg    120

ccaggaaccg cccctaagtt gctcatatat tatgataaca agcggccttc aggcgttcct    180

gatcgtttct ccggctctaa aagtggcaca tccgccagtc ttgctatcag cggtctcaga    240

tccgaggacg aggccgacta ttattgtggt acatgggacg cttccctgtc aggttacgtc    300

tttggcggcg gcacaaaact gacagttctt ggccagccca aggccgcccc ctccgtgacc    360

ctgttccccc cctcctccga ggagctgcag gccaacaagg ccaccctggt gtgcctgatc    420

tccgacttct accccggcgc cgtgaccgtg gcctggaagg ccgactcctc ccccgtgaag    480

gccggcgtgg agaccaccac cccctccaag cagtccaaca acaagtacgc cgcctcctcc    540

tacctgtccc tgacccccga gcagtggaag tcccaccggt cctactcctg ccaggtgacc    600

cacgagggct ccaccgtgga gaagaccgtg gcccccgccg agtgctcc                 648
```

<210> SEQ ID NO 84
<211> LENGTH: 648
<212> TYPE: DNA
<213> ORGANISM: Artificial Sequence
<220> FEATURE:
<223> OTHER INFORMATION: Synthetic: Light chain coding gene

<400> SEQUENCE: 84

```
cagtctgtgc tgacccagcc tccccctgct tctggcaccc ctggccagag agtgaccatc     60

tcctgctccg gctcctcctc caacatcggc tccaacaccg tgtactggta tcagcagctg    120

cccggcaccg cccccaagct gctgatctac gccaactccc agcggccctc cggcgtgccc    180
```

gacagattct ccggctccaa gtccggcacc tccgcctccc tggccatctc cggcctgaga 240
tctgaggacg aggccgacta ctactgcggc tcctgggact actccctgtc cggctacgtg 300
ttcggcggag gcaccaagct gaccgtgctg ggccagccta aggccgctcc ctccgtgacc 360
ctgttccccc catcctccga ggaactgcag gccaacaagg ccaccctggt ctgcctgatc 420
tccgacttct accctggcgc cgtgaccgtg gcctggaagg ccgacagctc tcctgtgaag 480
gccggcgtgg aaaccaccac cccctccaag cagtccaaca acaaatacgc cgcctcctcc 540
tacctgtccc tgacccccga gcagtggaag tcccaccggt cctacagctg ccaggtcaca 600
cacgagggct ccaccgtgga aaagaccgtg gcccctgccg agtgctcc 648

<210> SEQ ID NO 85
<211> LENGTH: 648
<212> TYPE: DNA
<213> ORGANISM: Artificial Sequence
<220> FEATURE:
<223> OTHER INFORMATION: Synthetic: Light chain coding gene

<400> SEQUENCE: 85
cagagtgttt tgacccagcc tccttccgcc agcggcaccc ctgggcaacg ggttacaatc 60
agctgttccg ggagcagcag taacattggt aataataacg tctcttggta tcagcagttg 120
cctggcacag cacctaagct cctgatttac gctgactccc accggccttc cggcgtccct 180
gatcgtttct ccgggtcaaa aagtggaacc tcagcaagcc ttgcaatcag cggactgcgg 240
tccgaagatg aagctgacta ctactgcgct acctgggatt actcattgtc cggctacgtc 300
tttggggggg gaaccaaatt gacagtcttg ggtcagccca aggccgcccc ctccgtgacc 360
ctgttccccc cctcctccga ggagctgcag gccaacaagg ccaccctggt gtgcctgatc 420
tccgacttct accccggcgc cgtgaccgtg gcctggaagg ccgactcctc ccccgtgaag 480
gccggcgtgg agaccaccac cccctccaag cagtccaaca acaagtacgc cgcctcctcc 540
tacctgtccc tgacccccga gcagtggaag tcccaccggt cctactcctg ccaggtgacc 600
cacgagggct ccaccgtgga gaagaccgtg gcccccgccg agtgctcc 648

<210> SEQ ID NO 86
<211> LENGTH: 648
<212> TYPE: DNA
<213> ORGANISM: Artificial Sequence
<220> FEATURE:
<223> OTHER INFORMATION: Synthetic: Light chain coding gene

<400> SEQUENCE: 86
cagtccgtgc tgacccagcc cccctccgcc tccggcaccc ccggccagcg ggtgaccatc 60
tcctgctccg gctcctcctc caacatcggc tccaacgacg tgtcctggta ccagcagctg 120
cccggcaccg cccccaagct gctgatctac tacgacaaca accggccctc cggcgtgccc 180
gaccggttct ccggctccaa gtccggcacc tccgcctccc tggccatctc cggcctgcgg 240
tccgaggacg aggccgacta ctactgcggc gcctgggacg actccctgtc cggctacgtg 300
ttcggcggcg gcaccaagct gaccgtgctg ggccagccca aggccgcccc ctccgtgacc 360
ctgttccccc cctcctccga ggagctgcag gccaacaagg ccaccctggt gtgcctgatc 420
tccgacttct accccggcgc cgtgaccgtg gcctggaagg ccgactcctc ccccgtgaag 480
gccggcgtgg agaccaccac cccctccaag cagtccaaca acaagtacgc cgcctcctcc 540
tacctgtccc tgacccccga gcagtggaag tcccaccggt cctactcctg ccaggtgacc 600
cacgagggct ccaccgtgga gaagaccgtg gcccccgccg agtgctcc 648

<210> SEQ ID NO 87
<211> LENGTH: 651
<212> TYPE: DNA
<213> ORGANISM: Artificial Sequence
<220> FEATURE:
<223> OTHER INFORMATION: Synthetic: Light chain coding gene

<400> SEQUENCE: 87
caaagcgtac tcacccagcc cccatccgca tctggcactc ctggtcaacg ggttacaatc 60
tcttgtactg ggtcaagttc caatattgga aataacgcag tgaactggta tcagcagctc 120
cctggcaccg cccctaaact cttgatatac tatgactcta atcggccaag tggagtcccc 180
gataggttct caggttctaa gagtggcaca agtgccagcc tggcaatctc agggctcagg 240
tccgaagatg aggctgatta ttactgcgga gcttgggatg atagcctgag tggctacgtc 300
ttcgggggag gaacaaaatt gaccgtactt ggccagccca aggccgcccc ctccgtgacc 360
ctgttccccc cctcctccga ggagctgcag gccaacaagg ccaccctggt gtgcctgatc 420
tccgacttct accccggcgc cgtgaccgtg gcctggaagg ccgactcctc ccccgtgaag 480
gccggcgtgg agaccaccac cccctccaag cagtccaaca acaagtacgc cgcctcctcc 540
tacctgtccc tgacccccga gcagtggaag tcccaccggt cctactcctg ccaggtgacc 600
cacgagggct ccaccgtgga gaagaccgtg gcccccgccg agtgctcctg a 651

<210> SEQ ID NO 88
<211> LENGTH: 648
<212> TYPE: DNA
<213> ORGANISM: Artificial Sequence
<220> FEATURE:
<223> OTHER INFORMATION: Synthetic: Light chain coding gene

<400> SEQUENCE: 88
cagtccgtgc tgacccagcc cccctccgcc tccggcaccc ccggccagcg ggtgaccatc 60
tcctgcaccg gctcctcctc caacatcggc tccaacgacg tgacctggta ccagcagctg 120
cccggcaccg cccccaagct gctgatctac gccgactcca agcggccctc cggcgtgccc 180
gaccggttct ccggctccaa gtccggcacc tccgcctccc tggccatctc cggcctgcgg 240
tccgaggacg aggccgacta ctactgcggc acctgggact actccctgtc cggctacgtg 300
ttcggcggcg gcaccaagct gaccgtgctg ggccagccca aggccgcccc ctccgtgacc 360
ctgttccccc cctcctccga ggagctgcag gccaacaagg ccaccctggt gtgcctgatc 420
tccgacttct accccggcgc cgtgaccgtg gcctggaagg ccgactcctc ccccgtgaag 480
gccggcgtgg agaccaccac cccctccaag cagtccaaca acaagtacgc cgcctcctcc 540
tacctgtccc tgacccccga gcagtggaag tcccaccggt cctactcctg ccaggtgacc 600
cacgagggct ccaccgtgga gaagaccgtg gcccccgccg agtgctcc 648

<210> SEQ ID NO 89
<211> LENGTH: 648
<212> TYPE: DNA
<213> ORGANISM: Artificial Sequence
<220> FEATURE:
<223> OTHER INFORMATION: Synthetic: Light chain coding gene

<400> SEQUENCE: 89
caaagtgtat tgactcaacc tccctccgct tccggtacac cagggcagcg agtaaccatc 60
agttgcagtg gcagcagctc caatatcgga agcaattatg taagttggta tcaacagttg 120

```
ccagggaccg ctccaaaact gttgatctat gacgacagtc accgtccttc aggtgtgccc    180

gaccgatttt caggcagcaa gagcggcaca tccgcctccc tcgctatctc cggcctccga    240

tccgaagatg aggccgacta ctattgtgga gcctgggacg actcccttag tggctatgtg    300

tttgggggag ggacaaagtt gaccgtactt ggccagccca aggccgcccc ctccgtgacc    360

ctgttccccc cctcctccga ggagctgcag gccaacaagg ccaccctggt gtgcctgatc    420

tccgacttct accccggcgc cgtgaccgtg gcctggaagg ccgactcctc ccccgtgaag    480

gccggcgtgg agaccaccac cccctccaag cagtccaaca acaagtacgc cgcctcctcc    540

tacctgtccc tgacccccga gcagtggaag tcccaccggt cctactcctg ccaggtgacc    600

cacgagggct ccaccgtgga gaagaccgtg gcccccgccg agtgctcc                648
```

<210> SEQ ID NO 90
<211> LENGTH: 648
<212> TYPE: DNA
<213> ORGANISM: Artificial Sequence
<220> FEATURE:
<223> OTHER INFORMATION: Synthetic: Light chain coding gene

<400> SEQUENCE: 90

```
cagtcagttc ttacacaacc cccatccgct tctggcactc ccggccagcg cgtaactata     60

tcttgctctg ggagtagtag caatatcggt aataatgatg tctcatggta ccaacagctg    120

cctggaacag cccccaaact cctcatttat gatgactctc aaaggccaag tggtgtgcca    180

gacagatttt ccggtagcaa gagtggaaca tcagcaagtc ttgctataag tggcttgcgt    240

tccgaggacg aggccgacta ttattgtggc gcatgggatg actcactgag cggctacgtt    300

ttcgggggcg gtactaagtt gaccgttttg ggacagccca aggccgcccc ctccgtgacc    360

ctgttccccc cctcctccga ggagctgcag gccaacaagg ccaccctggt gtgcctgatc    420

tccgacttct accccggcgc cgtgaccgtg gcctggaagg ccgactcctc ccccgtgaag    480

gccggcgtgg agaccaccac cccctccaag cagtccaaca acaagtacgc cgcctcctcc    540

tacctgtccc tgacccccga gcagtggaag tcccaccggt cctactcctg ccaggtgacc    600

cacgagggct ccaccgtgga gaagaccgtg gcccccgccg agtgctcc                648
```

<210> SEQ ID NO 91
<211> LENGTH: 330
<212> TYPE: PRT
<213> ORGANISM: Artificial Sequence
<220> FEATURE:
<223> OTHER INFORMATION: Synthetic: Heavy chain constant region

<400> SEQUENCE: 91

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
```

```
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 92
<211> LENGTH: 993
<212> TYPE: DNA
<213> ORGANISM: Artificial Sequence
<220> FEATURE:
<223> OTHER INFORMATION: Synthetic: Heavy chain constant region coding gene

<400> SEQUENCE: 92

```
gcctccacca agggcccctc cgtgttcccc ctggccccct cctccaagtc cacctccggc     60

ggcaccgccg ccctgggctg cctggtgaag gactacttcc ccgagcccgt gaccgtgtcc    120

tggaactccg gcgccctgac ctccggcgtg cacaccttcc ccgccgtgct gcagtcctcc    180

ggcctgtact ccctgtcctc cgtcgtgacc gtgccctcct cctccctggg cacccagacc    240

tacatctgca acgtgaacca caagccctcc aacaccaagg tggacaagaa ggtggagccc    300

aagtcctgcg acaagaccca cacctgccct ccctgccccg cccccgagct gctgggcggc    360

ccctccgtgt tcctgttccc tcctaagccc aaggacaccc tgatgatctc ccggaccccc    420

gaggtgactt gcgtggtggt ggacgtgtcc cacgaggacc ccgaggtgaa gttcaactgg    480

tacgtggacg gcgtggaggt gcacaacgcc aagaccaagc cccgggagga gcagtacaac    540

tccacctacc gggtggtgtc cgtgctgacc gtgctgcacc aggactggct gaacggcaag    600

gagtacaagt gcaaggtgtc caacaaggcc ctgcccgccc ccatcgagaa gaccatctcc    660

aaggccaagg gccagccccg ggagccccag gtgtacaccc tgcccccctc ccgggaggag    720
```

-continued atgaccaaga accaggtgtc cctgacctgc ctggtgaagg gcttctaccc ctccgacatc 780
gccgtggagt gggagtccaa cggccagccc gagaacaact acaagaccac cccccccgtg 840
ctggactccg acggctcctt cttcctgtac tccaagctga ccgtggacaa gtcccggtgg 900
cagcagggca acgtgttctc ctgctccgtg atgcacgagg ccctgcacaa ccactacacc 960
cagaagtccc tgtccctgtc ccccggcaag tga 993

<210> SEQ ID NO 93
<211> LENGTH: 105
<212> TYPE: PRT
<213> ORGANISM: Artificial Sequence
<220> FEATURE:
<223> OTHER INFORMATION: Synthetic: Light chain constant region

<400> SEQUENCE: 93

Gln Pro Lys Ala Ala Pro Ser Val Thr Leu Phe Pro Pro Ser Ser Glu
1 5 10 15

Glu Leu Gln Ala Asn Lys Ala Thr Leu Val Cys Leu Ile Ser Asp Phe
20 25 30

Tyr Pro Gly Ala Val Thr Val Ala Trp Lys Ala Asp Ser Ser Pro Val
35 40 45

Lys Ala Gly Val Glu Thr Thr Thr Pro Ser Lys Gln Ser Asn Asn Lys
50 55 60

Tyr Ala Ala Ser Ser Tyr Leu Ser Leu Thr Pro Glu Gln Trp Lys Ser
65 70 75 80

His Arg Ser Tyr Ser Cys Gln Val Thr His Glu Gly Ser Thr Val Glu
85 90 95

Lys Thr Val Ala Pro Ala Glu Cys Ser
100 105

<210> SEQ ID NO 94
<211> LENGTH: 318
<212> TYPE: DNA
<213> ORGANISM: Artificial Sequence
<220> FEATURE:
<223> OTHER INFORMATION: Synthetic: Light chain constant region coding gene

<400> SEQUENCE: 94
cagcccaagg ccgccccctc cgtgaccctg ttcccccct cctccgagga gctgcaggcc 60
aacaaggcca ccctggtgtg cctgatctcc gacttctacc ccggcgccgt gaccgtggcc 120
tggaaggccg actcctcccc cgtgaaggcc ggcgtggaga ccaccacccc ctccaagcag 180
tccaacaaca agtacgccgc ctcctcctac ctgtccctga cccccgagca gtggaagtcc 240
caccggtcct actcctgcca ggtgacccac gagggctcca ccgtggagaa gaccgtggcc 300
cccgccgagt gctcctga 318

<210> SEQ ID NO 95
<211> LENGTH: 318
<212> TYPE: DNA
<213> ORGANISM: Artificial Sequence
<220> FEATURE:
<223> OTHER INFORMATION: Synthetic: Light chain constant region coding gene

<400> SEQUENCE: 95
cagcctaagg ccgctccctc cgtgaccctg ttcccccat cctccgagga actgcaggcc 60
aacaaggcca ccctggtctg cctgatctcc gacttctacc ctggcgccgt gaccgtggcc 120

-continued

```
tggaaggccg acagctctcc tgtgaaggcc ggcgtggaaa ccaccacccc ctccaagcag    180

tccaacaaca aatacgccgc ctcctcctac ctgtccctga cccccgagca gtggaagtcc    240

caccggtcct acagctgcca ggtcacacac gagggctcca ccgtggaaaa gaccgtggcc    300

cctgccgagt gctcctga                                                  318
```

```
<210> SEQ ID NO 96
<211> LENGTH: 17
<212> TYPE: PRT
<213> ORGANISM: Artificial Sequence
<220> FEATURE:
<223> OTHER INFORMATION: Synthetic: Heavy chain CDR2

<400> SEQUENCE: 96

Ser Ile Ser Pro Asp Ala Ser Asn Thr Tyr Tyr Ala Asp Ser Val Lys
1               5                   10                  15

Gly


<210> SEQ ID NO 97
<211> LENGTH: 12
<212> TYPE: PRT
<213> ORGANISM: Artificial Sequence
<220> FEATURE:
<223> OTHER INFORMATION: Synthetic: Heavy chain CDR3

<400> SEQUENCE: 97

Gly Gly Asn Ala Ala Trp Asp Thr Gly Phe Asp Tyr
1               5                   10


<210> SEQ ID NO 98
<211> LENGTH: 116
<212> TYPE: PRT
<213> ORGANISM: Artificial Sequence
<220> FEATURE:
<223> OTHER INFORMATION: Synthetic: Heavy chain variable region

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ser Ile Ser Pro Asp Ala Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Arg Ala Phe Asp Tyr Trp Gly Gln Gly Thr Leu Val
            100                 105                 110

Thr Val Ser Ser
        115


<210> SEQ ID NO 99
<211> LENGTH: 121
<212> TYPE: PRT
<213> ORGANISM: Artificial Sequence
<220> FEATURE:
<223> OTHER INFORMATION: Synthetic: Heavy chain variable region

<400> SEQUENCE: 99
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Ala Ile Tyr His Ser Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Ala Ala Trp Asp Thr Gly Phe Asp Tyr Trp Gly
            100                 105                 110

Gln Gly Thr Leu Val Thr Val Ser Ser
        115                 120
```

<210> SEQ ID NO 100
<211> LENGTH: 446
<212> TYPE: PRT
<213> ORGANISM: Artificial Sequence
<220> FEATURE:
<223> OTHER INFORMATION: Synthetic: Heavy chain

<400> SEQUENCE: 100

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ser Ile Ser Pro Asp Ala Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Arg Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240
```

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 101
<211> LENGTH: 451
<212> TYPE: PRT
<213> ORGANISM: Artificial Sequence
<220> FEATURE:
<223> OTHER INFORMATION: Synthetic: Heavy chain

<400> SEQUENCE: 101

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Asp Met Ser Trp Val Arg Gln Ala Pro Gly Lys Gly Leu Glu Trp Val
35 40 45

Ser Ala Ile Tyr His Ser Gly Ser Ser Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Asn Ala Ala Trp Asp Thr Gly Phe Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 102
<211> LENGTH: 1338
<212> TYPE: DNA
<213> ORGANISM: Artificial Sequence
<220> FEATURE:
<223> OTHER INFORMATION: Synthetic: Heavy chain coding gene

<400> SEQUENCE: 102

gaagtgcagc tgctggaatc cggcggaggc ctggtgcagc ctggcggctc tctgagactg      60

tcttgcgccg cctccggctt caccttctcc gactactaca tgtcctgggt gcgacaggcc     120

cctggcaagg gcctggaatg ggtgtcctcc atctcccccg acgcctccaa cacctactac     180

gccgactccg tgaagggccg gttcaccatc tcccgggaca actccaagaa caccctgtac     240

ctgcagatga actccctgcg ggccgaggac accgccgtgt actactgcgc caagaacctg     300

cgggccttcg actactgggg ccagggcaca ctggtgaccg tgtcctccgc ctccaccaag     360
```

```
ggcccctccg tgttccccct ggcccctcc tccaagtcca cctccggcgg caccgccgcc    420
ctgggctgcc tggtgaagga ctacttcccc gagcccgtga ccgtgtcctg gaactccggc    480
gccctgacct ccggcgtgca caccttcccc gccgtgctgc agtcctccgg cctgtactcc    540
ctgtcctccg tcgtgaccgt gccctcctcc tccctgggca cccagaccta catctgcaac    600
gtgaaccaca agccctccaa caccaaggtg gacaagaagg tggagcccaa gtcctgcgac    660
aagacccaca cctgccctcc ctgccccgcc cccgagctgc tgggcggccc ctccgtgttc    720
ctgttccctc ctaagcccaa ggacaccctg atgatctccc ggacccccga ggtgacttgc    780
gtggtggtgg acgtgtccca cgaggacccc gaggtgaagt tcaactggta cgtggacggc    840
gtggaggtgc acaacgccaa gaccaagccc cgggaggagc agtacaactc cacctaccgg    900
gtggtgtccg tgctgaccgt gctgcaccag gactggctga acggcaagga gtacaagtgc    960
aaggtgtcca acaaggccct gcccgccccc atcgagaaga ccatctccaa ggccaagggc   1020
cagccccggg agccccaggt gtacaccctg ccccccctccc gggaggagat gaccaagaac   1080
caggtgtccc tgacctgcct ggtgaagggc ttctacccct ccgacatcgc cgtggagtgg   1140
gagtccaacg gccagcccga gaacaactac aagaccaccc cccccgtgct ggactccgac   1200
ggctccttct tcctgtactc caagctgacc gtggacaagt cccggtggca gcagggcaac   1260
gtgttctcct gctccgtgat gcacgaggcc ctgcacaacc actacaccca gaagtccctg   1320
tccctgtccc ccggcaag                                                 1338
```

<210> SEQ ID NO 103
<211> LENGTH: 1353
<212> TYPE: DNA
<213> ORGANISM: Artificial Sequence
<220> FEATURE:
<223> OTHER INFORMATION: Synthetic: Heavy chain coding gene

<400> SEQUENCE: 103

```
gaggtgcagc tgctggagtc cggcggcggc ctggtgcagc ccggcggctc cctgcggctg     60
tcctgcgccg cctccggctt caccttctcc aactacgaca tgtcctgggt gcggcaggcc    120
cccggcaagg gcctggagtg ggtgtccgcc atctaccact ccggctcctc caagtactac    180
gccgactccg tgaagggccg gttcaccatc tcccgggaca actccaagaa caccctgtac    240
ctgcagatga actccctgcg ggccgaggac accgccgtgt actactgcgc ccggggcggc    300
aacgccgcct gggacaccgg cttcgactac tggggccagg gcaccctggt gaccgtgtcc    360
tccgcctcca ccaagggccc ctccgtgttc cccctggccc cctcctccaa gtccacctcc    420
ggcggcaccg ccgccctggg ctgcctggtg aaggactact tccccgagcc cgtgaccgtg    480
tcctggaact ccggcgccct gacctccggc gtgcacacct tccccgccgt gctgcagtcc    540
tccggcctgt actccctgtc ctccgtcgtg accgtgccct cctcctccct gggcacccag    600
acctacatct gcaacgtgaa ccacaagccc tccaacacca aggtggacaa gaaggtggag    660
cccaagtcct gcgacaagac ccacacctgc cctccctgcc ccgcccccga gctgctgggc    720
ggcccctccg tgttcctgtt ccctcctaag cccaaggaca ccctgatgat ctcccggacc    780
cccgaggtga cttgcgtggt ggtggacgtg tcccacgagg accccgaggt gaagttcaac    840
tggtacgtgg acggcgtgga ggtgcacaac gccaagacca agccccggga ggagcagtac    900
aactccacct accgggtggt gtccgtgctg accgtgctgc accaggactg gctgaacggc    960
aaggagtaca agtgcaaggt gtccaacaag gccctgcccg cccccatcga gaagaccatc   1020
```

-continued

```
tccaaggcca agggccagcc ccgggagccc caggtgtaca ccctgccccc ctcccgggag    1080

gagatgacca agaaccaggt gtccctgacc tgcctggtga agggcttcta cccctccgac    1140

atcgccgtgg agtgggagtc caacggccag cccgagaaca actacaagac cacccccccc    1200

gtgctggact ccgacggctc cttcttcctg tactccaagc tgaccgtgga caagtcccgg    1260

tggcagcagg gcaacgtgtt ctcctgctcc gtgatgcacg aggccctgca caaccactac    1320

acccagaagt ccctgtccct gtcccccggc aag                                 1353
```